(12) United States Patent
Mi et al.

(10) Patent No.: US 7,846,438 B2
(45) Date of Patent: Dec. 7, 2010

(54) METHODS OF PROMOTING NEURITE OUTGROWTH WITH SOLUBLE TAJ POLYPEPTIDES

(75) Inventors: Sha Mi, Belmont, MA (US); Jeffrey L. Browning, Brookline, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 1029 days.

(21) Appl. No.: 11/195,851

(22) Filed: Aug. 3, 2005

(65) Prior Publication Data

US 2006/0058223 A1 Mar. 16, 2006

Related U.S. Application Data

(60) Provisional application No. 60/598,247, filed on Aug. 3, 2004.

(51) Int. Cl.
*A61K 38/16* (2006.01)
*A61K 39/00* (2006.01)
(52) U.S. Cl. .................................. 424/134.1; 514/12
(58) Field of Classification Search ............... None
See application file for complete search history.

(56) References Cited

U.S. PATENT DOCUMENTS

| 5,225,538 | A | 7/1993 | Capon et al. |
| 5,447,851 | A | 9/1995 | Beutler et al. |
| 2002/0068696 | A1 | 6/2002 | Wood et al. |
| 2003/0219860 | A1 | 11/2003 | Tschopp et al. |
| 2004/0142423 | A1 | 7/2004 | Tada et al. |
| 2007/0186296 | A1 | 8/2007 | Gao et al. |

FOREIGN PATENT DOCUMENTS

| EP | 0990703 A1 | 4/2000 |
| WO | WO 94/04679 | 3/1994 |
| WO | WO 98/01554 | 1/1998 |
| WO | WO 99/11791 | 3/1999 |
| WO | WO 99/13078 | 3/1999 |
| WO | WO 99/20644 | 4/1999 |
| WO | WO 99/33967 | 7/1999 |
| WO | WO 99/33980 | 7/1999 |
| WO | WO 99/37818 | 7/1999 |
| WO | WO 00/01817 | 1/2000 |
| WO | WO 2006/017673 A2 | 1/2000 |
| WO | WO 00/49149 | 8/2000 |
| WO | WO 00/53758 | 9/2000 |
| WO | WO 01/38526 | 5/2001 |
| WO | WO 01/58954 | 8/2001 |
| WO | WO 01/68848 | 9/2001 |
| WO | WO 01/93983 | 12/2001 |
| WO | WO 02/00690 | 1/2002 |
| WO | WO 02/08284 | 1/2002 |
| WO | WO 02/08288 | 1/2002 |
| WO | WO 03/013578 | 2/2003 |
| WO | WO 2005/058028 | 6/2005 |

OTHER PUBLICATIONS

Purves, Dale, et al (Eds.), Neuroscience, 2001, Sinauer Associates, Inc., 2nd Edition, pp. 75, 367, 400, 403, 554, 555 and 679.*
Vickers. A vaccine against Alzheimer's disease: developments to date. Drugs Aging 2002; 19(7):487-94.*
Stokes et al. (Experimental modeling of human spinal cord injury: a model that crosses the species barrier and mimic the spectrum of human cytopathology, Spinal Cord 40: 101-109, 2002.*
Talac et al. Animal models of spinal cord injury for evaluation of tissue engineering treatment strategies, Biomaterials 25: 1505-1510, 2004.*
Mills et al. Strain and model differences in behavioral outcomes after spinal cord injury in rat,J. Neurotrauma Aug;18(8):743-56, 2001.*
Mautes et al. Vascular events after spinal cord injury: contribution to secondary pathogenesis. Phys Ther. Jul. 2000;80(7):673-87.*
Helmuth. New therapies. New Alzheimer's treatments that may ease the mind. Science. Aug. 23, 2002;297(5585):1260-2.*
Rosenberg, L.J. and Warthall, J. R., "Time Course Studies on the Effectiveness of Tetrodotoxin in Reducing Consequences of Spinal Cord Contusion," *J. Neurosci. Res.* 66:191-202, Wiley-Liss, Inc. (2001).
International Search Report for International Patent Application No. PCT/US05/27773, United States Patent and Trademark Office, Alexandria, VA, mailed on Dec. 4, 2006.
Written Opinion of the International Search Authority for International Patent Application No. PCT/US05/27773, United States Patent and Trademark Office, Alexandria, VA, mailed on Dec. 4, 2006.
Aggarwal, B.B., and Natarajan, K., "Tumor Necrosis Factors: Developments During the Last Decade," *Eur. Cytokine Netw.* 7: 93-124, John Libbey Eurotext Ltd. (1996).
Banner, D.W., et al., "Crystal Structure of the Soluble Human 55 kd TNF Receptor-Human TNFβ Complex: Implications for TNF Receptor Activation," *Cell* 73:431-445, Cell Press (1993).
Bazzoni, F., and Beutler, B., "The Tumor Necrosis Factor Ligand and Receptor Families," *N. Engl. J. Med.* 334: 1717-1725, Massachusetts Medical Society (1996).
Bodmer, J.-L., et al., "The molecular architecture of the TNF superfamily," *Trends Biomed. Sci.* 27:19-26, Elsevier Science Ltd. (2002).
Bork, P., "Powers and Pitfalls in Sequence Analysis: The 70% Hurdle," *Genome Res.* 10:398-400, Cold Spring Harbor Laboratory Press (2000).
Copray, S., et al., Deficient p75 Low-affinity Neurotrophin Receptor Expression Exacerbates Experimental Allergic Encephalomyelitis in C57/BL6 Mice, *J. Neuroimmunol.* 148: 41-53, Elsevier/Holland (Mar. 2004).

(Continued)

*Primary Examiner*—Daniel Kolker
*Assistant Examiner*—Gregory S Emch
(74) *Attorney, Agent, or Firm*—Sterne, Kessler, Goldstein & Fox P.L.L.C.

(57) ABSTRACT

The invention provides methods of treating diseases, disorders, injuries, or conditions involving modulating neurite outgrowth and/or survival, including CNS disorders, stroke, or spinal injury, by administration of a TAJ antagonist.

16 Claims, 10 Drawing Sheets

OTHER PUBLICATIONS

Eason, J.D., et al., "Evaluation of Recombinant Human Soluble Dimeric Tumor Necrosis Factor Receptor for Prevention of OKT3-associated Acute Clinical Syndrome," *Transplantation* 61:224-228 (1996).

Eby, M.T., et al., "TAJ, a Novel Member of the Tumor Necrosis Factor Receptor Family, Activates the c-Jun N-terminal Kinase Pathway and Mediates Caspase-independent Cell Death," *J. Biol. Chem.* 275:15336-15342, The American Society for Biochemistry and Molecular Biology, Inc. (2000).

Eggermont, A.M., et al., "Isolated Limb Perfusion with High-Dose Tumor Necrosis Factor-Alpha in Combination With Interferon-Gamma and Melphalan for Nonresectable Extremity Soft Tissue Sarcomas: A Multicenter Trial," *J. Clin. Oncol* 14:2653-2665, Springer (1996).

Feldmann, M., et al., "Role of Cytokines in Rheumatoid Arthritis," *Annu. Rev. Immunol.* 14:397-440, Annual Reviews (1996).

Fournier, A.E., et al., "Identification of a Receptor Mediating Nogo-66 Inhibition of Axonal Regeneration," *Nature* 409:341-346, Nature Publishing Group (2001).

Giehl, K.M., et al., "Endogenous Brain-derived Neurotrophic Factor and Neurotrophin-3 Antagonistically Regulate Survival of Axotomized Corticospinal Neurons In Vivo," *J. Neurosci.* 21: 3492-3502, Society for Neuroscience (2001).

Green, D.R., and Ware, C.F., "Fas-Ligand: Privilege and Peril," *Proc. Natl. Acad. Sci. USA* 94:5986-5990, National Academy of Sciences (1997).

Hisaoka, T., et al., "Expression of a member of tumor necrosis factor receptor superfamily, TROY, in the developing mouse brain," *Develop. Brain Res.* 143:105-109, Elsevier Science B.V. (Jun. 2003).

Kojima, T., et al., "TROY, a Newly Identified Member of the Tumor Necrosis Factor Receptor Superfamily, Exhibits a Homology with Edar and Is Expressed in Embryonic Skin and Hair Follicles," *J. Biol. Chem.* 275:20742-20747, The American Society for Biochemistry and Molecular Biology, Inc. (2000).

Mandemakers, W.J. and Barres, B.A., "Axon Regeneration: It's Getting Crowded at the Gates of TROY," *Curr. Biol.* 15:R302-R305, Cell Press (Apr. 2005).

Mi, S., et al., "Lingo-1 is a Component of the Nogo-66 Receptor/p75 Signaling Complex," *Nat. Neurosci.* 7:221-228, Nature Publishing Group (Mar. 2004).

Mikayama, T., et al., "Molecular Cloning and Functional Expression of a cDNA Encoding Glycosylation-Inhibiting Factor," *Proc. Natl. Acad. Sci. USA* 90:10056-10060, National Academy of Sciences (1993).

Robertson, N.G., et al., "Isolation of Novel and Known Genes from a Human Fetal Cochlear cDNA Library Using Subtractive Hybridization and Differential Screening," *Genomics* 23:42-50, Academic Press, Inc. (1994).

Rutishauser, U., and Jessell, J.M., Cell Adhesion Molecules in Vertebrate Neural Development, *Physiol. Rev.* 68:819, American Physiological Society (1988).

Shao, Z., et al., "TAJ/TROY, an Orphan TNF Receptor Family Member, Binds Nogo-66 Receptor 1 and Regulates Axonal Regeneration," *Neuron* 45:353-359, Elsevier Inc. (Feb. 2004).

Skolnick, J., and Fetrow, J.S., "From Genes to Protein Structure and Function: Novel Applications of Computational Approaches in the Genomic Area," *Trends Biotechnol.* 18:34-39, Elsevier Science Publishers (2000).

Smith, C.A., et al., "CD30 Antigen, a Marker for Hodgkin's Lymphoma, is a Receptor Whose Ligand Defines an Emerging Family of Cytokines with Homology to TNF," *Cell* 73:1349-1360, Cell Press (1993).

Smith, C.A., et al., "The TNF Receptor Superfamily of Cellular and Viral Proteins: Activation, Costimulation, and Death," *Cell* 76:959-962, Cell Press (1994).

Smith, G.L., "Virus Strategies for Evasion of the Host Response to Infection," *Trends Microbiol.* 2:81-88, Elsevier Trends Journals (1994).

Song, X.Y., et al.,"Suppression of p75NTR Does Not Promote Regeneration of Injured Spinal Cord in Mice," *J. Neurosci.* 24:542-546, Society for Neuroscience (Jan. 2004).

van Dullemen, H.M., et al., "Treatment of Crohn's Disease with Anti-Tumor Necrosis Factor Chimeric Monoclonal Antibody (cA2)," *Gastroenterology* 109:129-135, W.B. Saunders (1995).

Wang, K.C., et al., "P75 Interacts With the Nogo Receptor as a Co-receptor for Nogo, MAG and OMgp," *Nature* 420:74-78, Nature Publishing Group (2002).

Wang, Y., et al., "An alternative form of paraptosis-like cell death, triggered by TAJ/TROY and enhanced by PDCD5 overexpression," *J. Cell Sci.* 117:1525-1532, The Company of Biologists (Mar. 2004).

Wilson, C.A. and Browning, J.L., "Death of HT29 adenocarcinoma cells induced by TNF family receptor activation is caspase-independent and displays features of both apoptosis and necrosis," *Cell Death Diff.* 9:1321-1333, Nature Publishing Group (2002).

NCBI Entrez, Accession No. AAF71828, Eby, M.T., et al. (May 25, 2000).

NCBI Entrez, Accession No. NP_061117, Clark, H.F., et al. (Jul. 5, 2000).

NCBI Entrez, Accession No. AB040434, Kojima, T., et al. (Jul. 22, 2000).

NCBI Entrez, Accession No. BAB03269, Kojima, T., et al. (Jul. 22, 2000).

NCBI Entrez, Accession No. AAK28396, Chaudhary, D., and Long, A.J. (Apr. 2, 2001).

NCBI Entrez, Accession No. AAK28397, Chaudhary, D., and Long, A.J. (Apr. 2, 2001).

NCBI Entrez, Accession No. AF246999, Chaudhary, D., and Long, A.J. (Apr. 2, 2001).

NCBI Entrez, Accession No. AF247000, Chaudhary, D., and Long, A.J. (Apr. 2, 2001).

NCBI Entrez, Accession No. Q9NS68, Eby, M.T., et al. (May 30, 2002).

NCBI Entrez, Accession No. NM_148957, Clark, H.F., et al. (Sep. 20, 2002).

NCBI Entrez, Accession No. BC047321, Strausberg, R.L., et al. (Mar. 3, 2003).

NCBI Entrez, Accession No. AY358888, Clark, H.F., et al. (Oct. 1, 2003).

NCBI Entrez, Accession No. CAH70838, Pearce, A. (Nov. 9, 2004).

NCBI Entrez, Accession No. AAH47321, Strausberg, R.L., et al. (Jul. 15, 2006).

U.S. Appl. No. 11/396,907, inventors Tschopp et al., filed Apr. 4, 2006 (unpublished).

Mi, Sha, "Troy/Taj and its role in CNS axon regeneration," *Cytokine Growth Factor Rev.* 19:245-251, Elsevier Ltd. (Jun. 2008).

Supplementary European Search Report for European Application No. EP 05 78 3641, European Patent Office, Munich, Germany, completed on Jul. 14, 2008.

\* cited by examiner

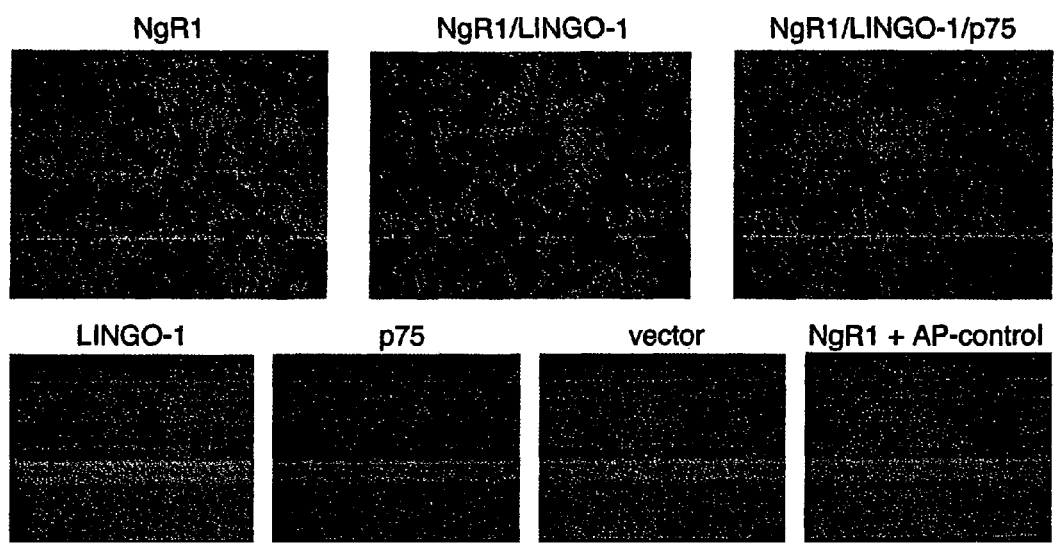
Figure 1B Binding of AP-Taj to NgR1-expressing CHO cells wildtype neurons control Fc +myelin Taj Fc +myelin Taj KO neurons − myelin + myelin AP-Nogo66 +control-Fc AP-Nogo66 +Taj-Fc

SEQUENCE LISTING

<160> NUMBER OF SEQ ID NOS: 25

<210> SEQ ID NO 1
<211> LENGTH: 1489
<212> TYPE: DNA
<213> ORGANISM: Homo sapiens

<400> SEQUENCE: 1

```
ggacctgcag cctcccaggt ggctgggaag aactctccaa caataaatac atttgataag     60
aaagatggct ttaaaagtgc tactagaaca agagaaaacg tttttcactc ttttagtatt    120
actaggctat ttgtcatgta aagtgacttg tgaatcagga gactgtagac agcaagaatt    180
cagggatcgg tctggaaact gtgttccctg caaccagtgt gggccaggca tggagttgtc    240
taaggaatgt ggcttcggct atggggagga tgcacagtgt gtggcgtgcc ggctgcacag    300
gttcaaggag gactggggct ccagaaatgc aagccctgtc tggactgcgc agtggtgaa    360
ccgctttcag aaggcaaatt gttcagccac cagtgatgcc atctgcgggg actgcttgcc    420
aggattttat aggaagacga aacttgtcgg cttcaagac atggagtgtg tgccttgtgg    480
agaccctcct cctccttacg aaccgcactg tgccagcaag gtcaacctcg tgaagatcgc    540
gtccacggcc tccagcccac gggacacggc gctggctgcc gttatctgca cgcgctctggc    600
caccgtcctg ctggccctgc tcatcctctg tgtcatctat tgtaagagac agtttatgga    660
aaagaaaccc agctggtctc tgcggtcaca ggacattcag tacaacgaga ctgagctgtc    720
gtgttttgac agacctcagc tccacgaata tgcccacaga gcctgctgcc agtgccgccg    780
tgactcagtg cagacctgcg ggccggtgcg cttgctccca tccatgtgct gtgaggaggc    840
ctgcagcccc aacccggcga ctcttggttg tggggtgcat tctgcagcca gtcttcaggc    900
aagaaacgca ggcccagccg gggagatggt gccgactttc ttcggatccc tcacgcagtc    960
catctgtggc gagttttcag atgcctggcc tctgatgcag aatcccatgg gtggtgacaa   1020
catctctttt tgtgactctt atcctgaact cactggagaa gacattcatt ctctcaatcc   1080
agaacttgaa agctcaacgt ctttggattc aaatagcagt caagatttgg ttggtggggc   1140
tgttccagtc cagtctcatt ctgaaaactt tacagcagct actgatttat ctagatataa   1200
caacacactg gtagaatcag catcaactca ggatgcacta actatgagaa gccagctaga   1260
tcaggagagt ggcgctgtca tccacccagc cactcagacg tccctccagg taaggcagcg   1320
actgggttcc ctgtgaacac agcactgact tacagtagat cagaactctg ttcccagcat   1380
aagatttggg ggaacctgga tgagtttttt tttttgcatc tttaataatt tcttatatgt   1440
tgtagagtat gttttaaaat aaatttcaag tatttttta aaaactttt                1489
```

<210> SEQ ID NO 2
<211> LENGTH: 423
<212> TYPE: PRT
<213> ORGANISM: Homo sapiens

<400> SEQUENCE: 2

```
Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys Glu Ser Gly
            20                  25                  30

Asp Cys Arg Gln Gln Glu Phe Arg Asp Arg Ser Gly Asn Cys Val Pro
        35                  40                  45

Cys Asn Gln Cys Gly Pro Gly Met Glu Leu Ser Lys Glu Cys Gly Phe
    50                  55                  60

Gly Tyr Gly Glu Asp Ala Gln Cys Val Ala Cys Arg Leu His Arg Phe
65                  70                  75                  80

Lys Glu Asp Trp Gly Phe Gln Lys Cys Lys Pro Cys Leu Asp Cys Ala
                85                  90                  95

Val Val Asn Arg Phe Gln Lys Ala Asn Cys Ser Ala Thr Ser Asp Ala
            100                 105                 110
```

```
Ile Cys Gly Asp Cys Leu Pro Gly Phe Tyr Arg Lys Thr Lys Leu Val
        115                 120                 125

Gly Phe Gln Asp Met Glu Cys Val Pro Cys Gly Asp Pro Pro Pro
        130                 135                 140

Tyr Glu Pro His Cys Ala Ser Lys Val Asn Leu Val Lys Ile Ala Ser
145                 150                 155                 160

Thr Ala Ser Ser Pro Arg Asp Thr Ala Leu Ala Ala Val Ile Cys Ser
                165                 170                 175

Ala Leu Ala Thr Val Leu Leu Ala Leu Leu Ile Leu Cys Val Ile Tyr
            180                 185                 190

Cys Lys Arg Gln Phe Met Glu Lys Lys Pro Ser Trp Ser Leu Arg Ser
            195                 200                 205

Gln Asp Ile Gln Tyr Asn Glu Thr Glu Leu Ser Cys Phe Asp Arg Pro
        210                 215                 220

Gln Leu His Glu Tyr Ala His Arg Ala Cys Cys Gln Cys Arg Arg Asp
225                 230                 235                 240

Ser Val Gln Thr Cys Gly Pro Val Arg Leu Leu Pro Ser Met Cys Cys
                245                 250                 255

Glu Glu Ala Cys Ser Pro Asn Pro Ala Thr Leu Gly Cys Gly Val His
            260                 265                 270

Ser Ala Ala Ser Leu Gln Ala Arg Asn Ala Gly Pro Ala Gly Glu Met
            275                 280                 285

Val Pro Thr Phe Phe Gly Ser Leu Thr Gln Ser Ile Cys Gly Glu Phe
        290                 295                 300

Ser Asp Ala Trp Pro Leu Met Gln Asn Pro Met Gly Gly Asp Asn Ile
305                 310                 315                 320

Ser Phe Cys Asp Ser Tyr Pro Glu Leu Thr Gly Glu Asp Ile His Ser
                325                 330                 335

Leu Asn Pro Glu Leu Glu Ser Ser Thr Ser Leu Asp Ser Asn Ser Ser
            340                 345                 350

Gln Asp Leu Val Gly Gly Ala Val Pro Val Gln Ser His Ser Glu Asn
        355                 360                 365

Phe Thr Ala Ala Thr Asp Leu Ser Arg Tyr Asn Asn Thr Leu Val Glu
370                 375                 380

Ser Ala Ser Thr Gln Asp Ala Leu Thr Met Arg Ser Gln Leu Asp Gln
385                 390                 395                 400

Glu Ser Gly Ala Val Ile His Pro Ala Thr Gln Thr Ser Leu Gln Val
                405                 410                 415

Arg Gln Arg Leu Gly Ser Leu
            420

<210> SEQ ID NO 3
<211> LENGTH: 1364
<212> TYPE: DNA
<213> ORGANISM: Homo sapiens

<400> SEQUENCE: 3
agaactctcc aacaataaat acatttgata agaaagatgg ctttaaaagt gctactagaa      60
caagagaaaa cgttttttcac tcttttagta ttactaggct atttgtcatg taaagtgact     120
tgtgaatcag gagactgtag acagcaagaa ttcagggatc ggtctggaaa ctgtgttccc     180
tgcaaccagt gtgggccagg catggagttg tctaaggaat gtggcttcgg ctatggggag     240
gatgcacagt gtgtgacgtg ccggctgcac aggttcaagg aggactgggg cttccagaaa     300
tgcaagccct gtctggactg cgcagtggtg aaccgctttc agaaggcaaa ttgttcagcc     360
```

-continued

```
accagtgatg ccatctgcgg ggactgcttg ccaggatttt ataggaagac gaaacttgtc      420
ggctttcaag acatggagtg tgtgccttgt ggagaccctc ctcctcctta cgaaccgcac      480
tgtgccagca aggtcaacct cgtgaagatc gcgtccacgg cctccagccc acgggacacg      540
gcgctggctg ccgttatctg cagcgctctg gccaccgtcc tgctggccct gctcatcctc      600
tgtgtcatct attgtaagag acagtttatg gagaagaaac ccagctggtc tctgcgcgtca     660
caggacattc agtacaacgg ctctgagctg tcgtgttttg acagacctca gctccacgaa      720
tatgcccaca gagcctgctg ccagtgccgc cgtgactcag tgcagacctg cgggccggtg      780
cgcttgctcc catccatgtg ctgtgaggag gcctgcagcc caacccggc gactcttggt       840
tgtggggtgc attctgcagc cagtcttcag gcaagaaacg caggcccagc cggggagatg      900
gtgccgactt tcttcggatc cctcacgcag tccatctgtg gcgagttttc agatgcctgg      960
cctctgatgc agaatcccat gggtggtgac aacatctctt tttgtgactc ttatcctgaa     1020
ctcactggag aagacattca ttctctcaat ccagaacttg aaagctcaac gtctttggat     1080
tcaaatagca gtcaagattt ggttggtggg gctgttccag tccagtctca ttctgaaaac     1140
tttacagcag ctactgattt atctagatat aacaacacac tggtagaatc agcatcaact     1200
caggatgcac taactatgag aagccagcta gatcaggaga gtggcgctgt catccaccca     1260
gccactcaga cgtccctcca ggtaaggcag cgactgggtt ccctgtgaac acagcactga     1320
cttacagtag atcagaactc tgttcccagc ataagatttg gggg                      1364
```

<210> SEQ ID NO 4
<211> LENGTH: 423
<212> TYPE: PRT
<213> ORGANISM: Homo sapiens

<400> SEQUENCE: 4

```
Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys Glu Ser Gly
            20                  25                  30

Asp Cys Arg Gln Gln Glu Phe Arg Asp Arg Ser Gly Asn Cys Val Pro
        35                  40                  45

Cys Asn Gln Cys Gly Pro Gly Met Glu Leu Ser Lys Glu Cys Gly Phe
    50                  55                  60

Gly Tyr Gly Glu Asp Ala Gln Cys Val Thr Cys Arg Leu His Arg Phe
65                  70                  75                  80

Lys Glu Asp Trp Gly Phe Gln Lys Cys Lys Pro Cys Leu Asp Cys Ala
                85                  90                  95

Val Val Asn Arg Phe Gln Lys Ala Asn Cys Ser Ala Thr Ser Asp Ala
            100                 105                 110

Ile Cys Gly Asp Cys Leu Pro Gly Phe Tyr Arg Lys Thr Lys Leu Val
        115                 120                 125

Gly Phe Gln Asp Met Glu Cys Val Pro Cys Gly Asp Pro Pro Pro
    130                 135                 140

Tyr Glu Pro His Cys Ala Ser Lys Val Asn Leu Val Lys Ile Ala Ser
145                 150                 155                 160

Thr Ala Ser Ser Pro Arg Asp Thr Ala Leu Ala Ala Val Ile Cys Ser
                165                 170                 175

Ala Leu Ala Thr Val Leu Leu Ala Leu Leu Ile Leu Cys Val Ile Tyr
            180                 185                 190
```

```
Cys Lys Arg Gln Phe Met Glu Lys Lys Pro Ser Trp Ser Leu Arg Ser
        195                 200                 205

Gln Asp Ile Gln Tyr Asn Gly Ser Glu Leu Ser Cys Phe Asp Arg Pro
    210                 215                 220

Gln Leu His Glu Tyr Ala His Arg Ala Cys Cys Gln Cys Arg Arg Asp
225                 230                 235                 240

Ser Val Gln Thr Cys Gly Pro Val Arg Leu Leu Pro Ser Met Cys Cys
                245                 250                 255

Glu Glu Ala Cys Ser Pro Asn Pro Ala Thr Leu Gly Cys Gly Val His
                260                 265                 270

Ser Ala Ala Ser Leu Gln Ala Arg Asn Ala Gly Pro Ala Gly Glu Met
            275                 280                 285

Val Pro Thr Phe Phe Gly Ser Leu Thr Gln Ser Ile Cys Gly Glu Phe
        290                 295                 300

Ser Asp Ala Trp Pro Leu Met Gln Asn Pro Met Gly Gly Asp Asn Ile
305                 310                 315                 320

Ser Phe Cys Asp Ser Tyr Pro Glu Leu Thr Gly Glu Asp Ile His Ser
                325                 330                 335

Leu Asn Pro Glu Leu Glu Ser Ser Thr Ser Leu Asp Ser Asn Ser Ser
            340                 345                 350

Gln Asp Leu Val Gly Gly Ala Val Pro Val Gln Ser His Ser Glu Asn
        355                 360                 365

Phe Thr Ala Ala Thr Asp Leu Ser Arg Tyr Asn Asn Thr Leu Val Glu
        370                 375                 380

Ser Ala Ser Thr Gln Asp Ala Leu Thr Met Arg Ser Gln Leu Asp Gln
385                 390                 395                 400

Glu Ser Gly Ala Val Ile His Pro Ala Thr Gln Thr Ser Leu Gln Val
                405                 410                 415

Arg Gln Arg Leu Gly Ser Leu
            420

<210> SEQ ID NO 5
<211> LENGTH: 1325
<212> TYPE: DNA
<213> ORGANISM: Homo sapiens

<400> SEQUENCE: 5 atggcttta aagtgctact agaacaagag aaaacgtttt tcactctttt agtattacta      60
ggctatttgt catgtaaagt gacttgtgaa acaggagact gtagacagca agaattcagg    120
gatcggtctg gaaactgtgt tccctgcaac cagtgtgggc caggcatgga gttgtctaag    180
gaatgtggct tcggctatgg ggaggatgca cagtgtgtga cgtgccggct gcacaggttc    240
aaggaggact ggggcttcca gaaatgcaag ccctgtctgg actgcgcagt ggtgaaccgc    300
tttcagaagg caaattgttc agccaccagt gatgccatct gcggggactg cttgccagga    360
ttttatagga gacgaaaact tgtcggcttt caagacatgg agtgtgtgcc ttgtggagac    420
cctcctcctc cttacgaacc gcactgtgcc agcaaggtca acctcgtgaa gatcgcgtcc    480
acggcctcca gcccacggga cacggcgctg ctgccgttta ctgcagcgc tctggccacc    540 gtcctgctgg ccctgctcat cctctgtgtc atctattgta agagacagtt tatggagaag    600
aaacccagct ggtctctgcg gtcacaggac attcagtaca acggctctga gctgtcgtgt    660
cttgacagac ctcagctcca cgaatatgcc cacagagcct gctgccagtg ccgccgtgac    720
tcagtgcaga cctgcgggcc ggtgcgcttg ctcccatcca tgtgctgtga ggaggcctgc    780
```

```
agccccaacc cggcgactct tggttgtggg gtgcattctg cagccagtct tcaggcaaga      840
aacgcaggcc cagccgggga gatggtgccg actttcttcg gatccctcac gcagtccatc      900
tgtggcgagt tttcagatgc ctggcctctg atgcagaatc ccatgggtgg tgacaacatc      960 tcttttgtg actcttatcc tgaactcgct ggagaagaca ttcattctct caatccagaa     1020
cttgaaagct caacgtcttt ggattcaaat agcagtcaag atttggttgg tggggctgtt     1080
ccagtccagt ctcattctga aactttaca gcagctacta tttatctag atataacaac     1140 acactggtag aatcagcatc aactcaggat gcactaacta tgagaagcca gctagatcag     1200
gagagtggcg ctatcatcca cccagccact cagacgtccc tccaggtaag gcagcgactg     1260
ggttccctgt gaacacagca ctgacttaca gtagatcaga actctgttcc cagcataaga     1320
tttgg                                                                1325
```

<210> SEQ ID NO 6
<211> LENGTH: 423
<212> TYPE: PRT
<213> ORGANISM: Homo sapiens
<400> SEQUENCE: 6

```
Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys Glu Thr Gly
            20                  25                  30

Asp Cys Arg Gln Gln Glu Phe Arg Asp Arg Ser Gly Asn Cys Val Pro
        35                  40                  45

Cys Asn Gln Cys Gly Pro Gly Met Glu Leu Ser Lys Glu Cys Gly Phe
    50                  55                  60

Gly Tyr Gly Glu Asp Ala Gln Cys Val Thr Cys Arg Leu His Arg Phe
65                  70                  75                  80

Lys Glu Asp Trp Gly Phe Gln Lys Cys Lys Pro Cys Leu Asp Cys Ala
                85                  90                  95

Val Val Asn Arg Phe Gln Lys Ala Asn Cys Ser Ala Thr Ser Asp Ala
            100                 105                 110

Ile Cys Gly Asp Cys Leu Pro Gly Phe Tyr Arg Lys Thr Lys Leu Val
        115                 120                 125

Gly Phe Gln Asp Met Glu Cys Val Pro Cys Gly Asp Pro Pro Pro
    130                 135                 140

Tyr Glu Pro His Cys Ala Ser Lys Val Asn Leu Val Lys Ile Ala Ser
145                 150                 155                 160

Thr Ala Ser Ser Pro Arg Asp Thr Ala Leu Ala Ala Val Ile Cys Ser
                165                 170                 175

Ala Leu Ala Thr Val Leu Leu Ala Leu Leu Ile Leu Cys Val Ile Tyr
            180                 185                 190

Cys Lys Arg Gln Phe Met Glu Lys Lys Pro Ser Trp Ser Leu Arg Ser
        195                 200                 205

Gln Asp Ile Gln Tyr Asn Gly Ser Glu Leu Ser Cys Leu Asp Arg Pro
    210                 215                 220

Gln Leu His Glu Tyr Ala His Arg Ala Cys Cys Gln Cys Arg Arg Asp
225                 230                 235                 240

Ser Val Gln Thr Cys Gly Pro Val Arg Leu Leu Pro Ser Met Cys Cys
                245                 250                 255

Glu Glu Ala Cys Ser Pro Asn Pro Ala Thr Leu Gly Cys Gly Val His
            260                 265                 270
```

```
Ser Ala Ala Ser Leu Gln Ala Arg Asn Ala Gly Pro Ala Gly Glu Met
        275                 280                 285

Val Pro Thr Phe Phe Gly Ser Leu Thr Gln Ser Ile Cys Gly Glu Phe
    290                 295                 300

Ser Asp Ala Trp Pro Leu Met Gln Asn Pro Met Gly Gly Asp Asn Ile
305                 310                 315                 320

Ser Phe Cys Asp Ser Tyr Pro Glu Leu Ala Gly Glu Asp Ile His Ser
                325                 330                 335

Leu Asn Pro Glu Leu Glu Ser Ser Thr Ser Leu Asp Ser Asn Ser Ser
            340                 345                 350

Gln Asp Leu Val Gly Gly Ala Val Pro Val Gln Ser His Ser Glu Asn
        355                 360                 365

Phe Thr Ala Ala Thr Asp Leu Ser Arg Tyr Asn Asn Thr Leu Val Glu
    370                 375                 380

Ser Ala Ser Thr Gln Asp Ala Leu Thr Met Arg Ser Gln Leu Asp Gln
385                 390                 395                 400

Glu Ser Gly Ala Ile Ile His Pro Ala Thr Gln Thr Ser Leu Gln Val
                405                 410                 415

Arg Gln Arg Leu Gly Ser Leu
            420

<210> SEQ ID NO 7
<211> LENGTH: 15
<212> TYPE: PRT
<213> ORGANISM: Artificial Sequence
<220> FEATURE:
<223> OTHER INFORMATION: Linker sequence used to separate two polypetide
      coding regions

<400> SEQUENCE: 7

Gly Gly Gly Gly Ser Gly Gly Gly Ser Gly Gly Gly Gly Ser
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Linker sequence used to separate two polypetide
      coding regions

<400> SEQUENCE: 8

Glu Ser Gly Arg Ser Gly Gly Gly Gly Ser Gly Gly Gly Gly Ser
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: Linker sequence used to separate two polypetide
      coding regions

<400> SEQUENCE: 9

Glu Gly Lys Ser Ser Gly Ser Gly Ser Glu Ser Lys Ser Thr
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Linker sequence used to separate two polypetide
```

-continued coding regions

<400> SEQUENCE: 10

Glu Gly Lys Ser Ser Gly Ser Gly Ser Glu Ser Lys Ser Thr Gln
1               5                   10                  15

<210> SEQ ID NO 11
<211> LENGTH: 14
<212> TYPE: PRT
<213> ORGANISM: Artificial Sequence
<220> FEATURE:
<223> OTHER INFORMATION: Linker sequence used to separate two polypeptide
      coding regions

<400> SEQUENCE: 11

Glu Gly Lys Ser Ser Gly Ser Gly Ser Glu Ser Lys Val Asp
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Linker sequence used to separate two polypeptide
      coding regions

<400> SEQUENCE: 12

Gly Ser Thr Ser Gly Ser Gly Lys Ser Ser Glu Gly Lys Gly
1               5                   10

<210> SEQ ID NO 13
<211> LENGTH: 18
<212> TYPE: PRT
<213> ORGANISM: Artificial Sequence
<220> FEATURE:
<223> OTHER INFORMATION: Linker sequence used to separate two polypeptide
      coding regions

<400> SEQUENCE: 13

Lys Glu Ser Gly Ser Val Ser Ser Glu Gln Leu Ala Gln Phe Arg Ser
1               5                   10                  15

Leu Asp

<210> SEQ ID NO 14
<211> LENGTH: 16
<212> TYPE: PRT
<213> ORGANISM: Artificial Sequence
<220> FEATURE:
<223> OTHER INFORMATION: Linker sequence used to separate two polypeptide
      coding regions

<400> SEQUENCE: 14

Glu Ser Gly Ser Val Ser Ser Glu Glu Leu Ala Phe Arg Ser Leu Asp
1               5                   10                  15

<210> SEQ ID NO 15
<211> LENGTH: 3087
<212> TYPE: DNA
<213> ORGANISM: Homo sapiens

<400> SEQUENCE: 15
gggagggtaa ctacctgctg aaagtgaact ttctttgata tccatgcata tatataaact      60
cagccctgcc tttgatgttc agcaactgat tcactgatca gattacaggc atttcatctc     120
cctgctcgtc tgcctttgat ctgcatggtt aatttattt tcctggattt gaagtttcgt     180

-continued

```
ctgggcttgt gctgacatac attttggga aggtagaagc atttggcaca gaagtgctgc      240
caggagaaac taagttgctg aacggaactc tccaacaata aatacatttg ataagaaaga     300 tggcttaaa agtgctacta gaacaagaga aaacgttttt cactctttta gtattactag      360
gctatttgtc atgtaaagtg acttgtgaat caggagactg tagacagcaa gaattcaggg     420
atcggtctgg aaactgtgtt ccctgcaacc agtgtgggcc aggcatggag ttgtctaagg     480
aatgtggctt cggctatggg gaggatgcac agtgtgtgac gtgccggctg cacaggttca     540
aggaggactg gggcttccag aaatgcaagc cctgtctgga ctgcgcagtg gtgaaccgct     600
ttcagaaggc aaattgttca gccaccagtg atgccatctg cggggactgc ttgccaggat     660
tttataggaa gacgaaactt gtcggctttc aagacatgga gtgtgtgcct tgtggagacc     720
ctcctcctcc ttacgaaccg cactgtgcca gcaaggtcaa cctcgtgaag atcgcgtcca     780
cggcctccag cccacgggac acggcgctgg ctgccgttat ctgcagcgct ctggccaccg     840
tcctgctggc cctgctcatc ctctgtgtca tctattgtaa gagacagttt atggagaaga     900
aacccagctg gtctctgcgg tcacaggaca ttcagtacaa cggctctgag ctgtcgtgtt     960
ttgacagacc tcagctccac gaatatgccc acagagcctg ctgccagtgc cgccgtgact    1020
cagtgcagac ctgcgggccg gtgcgcttgc tcccatccat gtgctgtgag gaggcctgca    1080
gccccaaccc ggcgactctt ggttgtgggg tgcattctgc agccagtctt caggcaagaa    1140
acgcaggccc agccggggag atggtgccga cttctcttcgg atccctcacg cagtccatct    1200
gtggcgagtt tcagatgcc tggcctctga tgcagaatcc catgggtggt gacaacatct     1260 cttttttgtga ctcttatcct gaactcactg gagaagacat tcattctctc aatccagaac    1320
ttgaaagctc aacgtctttg gattcaaata gcagtcaaga tttggttggt ggggctgttc    1380
cagtccagtc tcattctgaa aactttacag cagctactga tttatctaga tataacaaca    1440
cactggtaga atcagcatca actcaggatg cactaactat gagaagccag ctagatcagg    1500
agagtggtgc tgtcatccac ccagccactc agacgtccct ccaggaagct taaagaacct    1560 gcttcttct gcagtagaag cgtgtgctgg aacccaaaga gtactccttt gttaggctta    1620
tggactgagc agtctggacc ttgcatggct tctggggcaa aaataaatct gaaccaaact    1680
gacggcattt gaagcctttc agccagttgc ttctgagcca gaccagctgt aagctgaaac    1740
ctcaatgaat aacaagaaaa gactccaggc cgactcatga tactctgcat cttttcctaca    1800 tgagaagctt ctctgccaca aaagtgactt caaagacgga tgggttgagc tggcagccta    1860
tgagattgtg gacatataac aagaaacaga aatgccctca tgcttatttt catggtgatt    1920
gtggttttac aagactgaag acccagagta tactttttct ttccagaaat aatttcatac    1980
cgcctatgaa atatcagata aattaccttta gcttttatgt agaatgggtt caaaagtgag   2040
tgtttctatt tgagaaggac actttttcat catctaaact gattcgcata ggtggttaga    2100
atggccctca tattgcctgc ctaaatcttg ggttattag atgaagttta ctgaatcaga    2160
ggaatcagac agaggaggat agctcttcc agaatccaca cttctgacct cagcctcggt     2220
ctcatgaaca cccgctgatc tcaggagaac acctgggcta gggaatgtgg tcgagaaagg    2280
gcagcccatt gcccagaatt aacacatatt gtagagactt gtatgcaaag gttggcatat    2340
ttatatgaaa attagttgct atagaaacat ttgttcatc tgtccctctg cctgagctta     2400
gaaggttata gaaaagggt atttataaac ataaatgacc ttttacttgc attgtatctt     2460
atactaaagg ctttagaaat tacaacatat caggttcccc tactactgaa gtagccttcc    2520
gtgagaacac accacatgtt aggactagaa gaaaatgcac aatttgtagg ggtttggatg    2580
```

-continued

```
aagcagctgt aactgccta gtgtagtttg accaggacat tgtcgtgctc cttccaattg    2640
tgtaagatta gttagcacat catctcctac tttagccatc cggtgctgga tttaagagga    2700
cggtgcttct ttctattaaa gtgctccatc ccctaccatc tacacattag cattgtctct    2760
agagctaaga cagaaattaa ccccgttcag tcacaaagca gggaatggtt catttactct    2820
taatctttat gccctggaga agacctactt gaacagggca tatttttag acttctgaac     2880 atcagtatgt tcgagggtac tatgatattt tggtttggaa ttgccctgcc caagtcactg    2940
tcttttaact tttaaactga atattaaaat gtatctgtct ttcctagtat gtttttatct    3000
tctcatgtat tatccatggt tttctctgtt tgtgacagat tagtaaaatt taatgagccc    3060
tcaaaaaaaa aaaaaaaaaa aaaaaaa                                       3087
```

<210> SEQ ID NO 16
<211> LENGTH: 417
<212> TYPE: PRT
<213> ORGANISM: Homo sapiens

<400> SEQUENCE: 16

```
Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys Glu Ser Gly
            20                  25                  30

Asp Cys Arg Gln Gln Glu Phe Arg Asp Arg Ser Gly Asn Cys Val Pro
        35                  40                  45

Cys Asn Gln Cys Gly Pro Gly Met Glu Leu Ser Lys Glu Cys Gly Phe
    50                  55                  60

Gly Tyr Gly Glu Asp Ala Gln Cys Val Thr Cys Arg Leu His Arg Phe
65                  70                  75                  80

Lys Glu Asp Trp Gly Phe Gln Lys Cys Lys Pro Cys Leu Asp Cys Ala
                85                  90                  95

Val Val Asn Arg Phe Gln Lys Ala Asn Cys Ser Ala Thr Ser Asp Ala
            100                 105                 110

Ile Cys Gly Asp Cys Leu Pro Gly Phe Tyr Arg Lys Thr Lys Leu Val
        115                 120                 125

Gly Phe Gln Asp Met Glu Cys Val Pro Cys Gly Asp Pro Pro Pro
    130                 135                 140

Tyr Glu Pro His Cys Ala Ser Lys Val Asn Leu Val Lys Ile Ala Ser
145                 150                 155                 160

Thr Ala Ser Ser Pro Arg Asp Thr Ala Leu Ala Val Ile Cys Ser
                165                 170                 175

Ala Leu Ala Thr Val Leu Leu Ala Leu Leu Ile Leu Cys Val Ile Tyr
            180                 185                 190

Cys Lys Arg Gln Phe Met Glu Lys Lys Pro Ser Trp Ser Leu Arg Ser
        195                 200                 205

Gln Asp Ile Gln Tyr Asn Gly Ser Glu Leu Ser Cys Phe Asp Arg Pro
    210                 215                 220

Gln Leu His Glu Tyr Ala His Arg Ala Cys Gln Cys Arg Arg Asp
225                 230                 235                 240

Ser Val Gln Thr Cys Gly Pro Val Arg Leu Leu Pro Ser Met Cys Cys
                245                 250                 255

Glu Glu Ala Cys Ser Pro Asn Pro Ala Thr Leu Gly Cys Gly Val His
            260                 265                 270

Ser Ala Ala Ser Leu Gln Ala Arg Asn Ala Gly Pro Ala Gly Glu Met
```

-continued

```
            275                 280                 285
Val Pro Thr Phe Phe Gly Ser Leu Thr Gln Ser Ile Cys Gly Glu Phe
    290                 295                 300

Ser Asp Ala Trp Pro Leu Met Gln Asn Pro Met Gly Gly Asp Asn Ile
305                 310                 315                 320

Ser Phe Cys Asp Ser Tyr Pro Glu Leu Thr Gly Glu Asp Ile His Ser
                325                 330                 335

Leu Asn Pro Glu Leu Glu Ser Ser Thr Ser Leu Asp Ser Asn Ser Ser
                340                 345                 350

Gln Asp Leu Val Gly Gly Ala Val Pro Val Gln Ser His Ser Glu Asn
            355                 360                 365

Phe Thr Ala Ala Thr Asp Leu Ser Arg Tyr Asn Asn Thr Leu Val Glu
    370                 375                 380

Ser Ala Ser Thr Gln Asp Ala Leu Thr Met Arg Ser Gln Leu Asp Gln
385                 390                 395                 400

Glu Ser Gly Ala Val Ile His Pro Ala Thr Gln Thr Ser Leu Gln Glu
                405                 410                 415

Ala
```

<210> SEQ ID NO 17
<211> LENGTH: 1914
<212> TYPE: DNA
<213> ORGANISM: Mus musculus

<400> SEQUENCE: 17

| | |
|---|---:|
| atggcactca aggtcctacc tctacacagg acggtgctct tcgctgccat tctcttccta | 60 |
| ctccacctgg catgtaaagt gagttgcgaa accggagatt gcaggcagca ggaattcaag | 120 |
| gatcgatctg gaaactgtgt cctctgcaaa cagtgcggac ctggcatgga gttgtccaag | 180 |
| gaatgtggct tcggctatgg ggaggatgca cagtgtgtgc cctgcaggcc gcaccggttc | 240 |
| aaggaagact ggggtttcca gaagtgtaag ccatgtgcgg actgtgcgct ggtgaaccgc | 300 |
| tttcagaggg ccaactgctc acacaccagt gatgctgtct gcggggactg cctgccagga | 360 |
| ttttaccgga agaccaaact ggttggtttt caagacatgg agtgtgtgcc ctgcggagac | 420 |
| ccacctcctc cctacgaacc acactgtacc agcaaggtga accttgtgaa gatctcctcc | 480 |
| accgtctcca gccctcggga cacggcgctg gctgccgtca tctgcagtgc tctggccacg | 540 |
| gtgctgctcg ccctgctcat cctgtgtgtc atctactgca agaggcagtt catggagaag | 600 |
| aaacccagct ggtctctgcg gtcacaggac attcagtaca atggctctga gctgtcatgc | 660 |
| tttgaccagc tcggctccg ccactgtgcc catagagcat gctgtcagta tcaccgggac | 720 |
| tcagccccaa tgtatgggcc tgttcacctg attccgtcct gtgctgtga agaggcccgc | 780 |
| agctctgccc gagctgtgct tggctgtggg ctgcgttctc ccactaccct ccaggagaga | 840 |
| aaccccggctt ctgtggggga cacgatgcca gccttcttcg ggtctgtttc ccgttccatc | 900 |
| tgcgctgaat ttctgatgc ctggcctctg atgcagaatc ctctgggtgg tgacagctct | 960 |
| ctctgtgact cttatcctga actcactgga agagatacca attccctcaa tcccgaaaac | 1020 |
| gaaagcgcag catctctgga ttccagtggc ggccaggatc tggctgggac agctgctcta | 1080 |
| gagtcttctg gaatgtttc agaatctact gactcaccta gcatggtgga cactggtaca | 1140 |
| gtctgggagc agacgctagc tcaggatgct caaaggactc caagccaagg aggctgggaa | 1200 |
| gacagggaaa acctgaatct agccatgccc acagccttcc aggatgcctg aaggccatct | 1260 |
| tcctgacgtg gaggtgtggg tctggacaag cctgtgatga ggcctacaga ctgagcagtc | 1320 |

-continued

```
ttggtgtctg gaagcaaaaa taaatctgaa ccaaactgac aacatttcca tcctttcagc   1380
cactagcttc tgagccagac cagctgtaag ctgaaacccc agcaagaagc aaggagagac   1440
tgactgtagg cggccttggg acatgtgctt cttccctaag cgagaacctt agctggggcc   1500
aatttgaagg acccatgggt ggaatgtgct gcctgtgagc ttgtgggcac agcaggaccc   1560
agcctggctc cttcttatgt ccacggtgaa tgtggtttca caagacccag agtataaact   1620
ttcatagaca ttctctttta gaaataatcc attaccctgt cttcaaaaac caaaaaaaaa   1680
aaaaagtggt gttaaggttt tgaacatcac ctagccaagt tagtaaaatc tttatttgta   1740
tttcatctca atttttttaa ctattcattt tccttgtatg aattcttgtg tgttttatgt   1800
gtaaatatat tcattatttt gacactatca atattctttg tggttttgta atttttactt   1860
ttattaatga ctcaagctgt aaaaataaac taatttcaac gtcgacgcgg ccgc        1914
```

<210> SEQ ID NO 18
<211> LENGTH: 416
<212> TYPE: PRT
<213> ORGANISM: Mus musculus

<400> SEQUENCE: 18

```
Met Ala Leu Lys Val Leu Pro Leu His Arg Thr Val Leu Phe Ala Ala
1               5                   10                  15

Ile Leu Phe Leu Leu His Leu Ala Cys Lys Val Ser Cys Glu Thr Gly
            20                  25                  30

Asp Cys Arg Gln Gln Glu Phe Lys Asp Arg Ser Gly Asn Cys Val Leu
        35                  40                  45

Cys Lys Gln Cys Gly Pro Gly Met Glu Leu Ser Lys Glu Cys Gly Phe
    50                  55                  60

Gly Tyr Gly Glu Asp Ala Gln Cys Val Pro Cys Arg Pro His Arg Phe
65                  70                  75                  80

Lys Glu Asp Trp Gly Phe Gln Lys Cys Lys Pro Cys Ala Asp Cys Ala
                85                  90                  95

Leu Val Asn Arg Phe Gln Arg Ala Asn Cys Ser His Thr Ser Asp Ala
            100                 105                 110

Val Cys Gly Asp Cys Leu Pro Gly Phe Tyr Arg Lys Thr Lys Leu Val
        115                 120                 125

Gly Phe Gln Asp Met Glu Cys Val Pro Cys Gly Asp Pro Pro Pro Pro
    130                 135                 140

Tyr Glu Pro His Cys Thr Ser Lys Val Asn Leu Val Lys Ile Ser Ser
145                 150                 155                 160

Thr Val Ser Ser Pro Arg Asp Thr Ala Leu Ala Ala Val Ile Cys Ser
                165                 170                 175

Ala Leu Ala Thr Val Leu Leu Ala Leu Leu Ile Leu Cys Val Ile Tyr
            180                 185                 190

Cys Lys Arg Gln Phe Met Glu Lys Lys Pro Ser Trp Ser Leu Arg Ser
        195                 200                 205

Gln Asp Ile Gln Tyr Asn Gly Ser Glu Leu Ser Cys Phe Asp Gln Pro
    210                 215                 220

Arg Leu Arg His Cys Ala His Arg Ala Cys Cys Gln Tyr His Arg Asp
225                 230                 235                 240

Ser Ala Pro Met Tyr Gly Pro Val His Leu Ile Pro Ser Leu Cys Cys
                245                 250                 255

Glu Glu Ala Arg Ser Ser Ala Arg Ala Val Leu Gly Cys Gly Leu Arg
            260                 265                 270
```

```
Ser Pro Thr Thr Leu Gln Glu Arg Asn Pro Ala Ser Val Gly Asp Thr
        275                 280                 285

Met Pro Ala Phe Phe Gly Ser Val Ser Arg Ser Ile Cys Ala Glu Phe
        290                 295                 300

Ser Asp Ala Trp Pro Leu Met Gln Asn Pro Leu Gly Gly Asp Ser Ser
305                 310                 315                 320

Leu Cys Asp Ser Tyr Pro Glu Leu Thr Gly Glu Asp Thr Asn Ser Leu
                325                 330                 335

Asn Pro Glu Asn Glu Ser Ala Ala Ser Leu Asp Ser Ser Gly Gly Gln
            340                 345                 350

Asp Leu Ala Gly Thr Ala Ala Leu Glu Ser Ser Gly Asn Val Ser Glu
        355                 360                 365

Ser Thr Asp Ser Pro Arg His Gly Asp Thr Gly Thr Val Trp Glu Gln
        370                 375                 380

Thr Leu Ala Gln Asp Ala Gln Arg Thr Pro Ser Gln Gly Gly Trp Glu
385                 390                 395                 400

Asp Arg Glu Asn Leu Asn Leu Ala Met Pro Thr Ala Phe Gln Asp Ala
                405                 410                 415

<210> SEQ ID NO 19
<211> LENGTH: 24
<212> TYPE: DNA
<213> ORGANISM: Artificial Sequence
<220> FEATURE:
<223> OTHER INFORMATION: forward primer used to show expression of TAJ
      in brain

<400> SEQUENCE: 19
tatggggagg atgcacagtg tgtg                                          24

<210> SEQ ID NO 20
<211> LENGTH: 24
<212> TYPE: DNA
<213> ORGANISM: Artificial Sequence
<220> FEATURE:
<223> OTHER INFORMATION: Reverse primer used to show expression of TAJ
      in brain

<400> SEQUENCE: 20
agaccagctg ggtttcttct ccat                                          24

<210> SEQ ID NO 21
<211> LENGTH: 24
<212> TYPE: DNA
<213> ORGANISM: Artificial Sequence
<220> FEATURE:
<223> OTHER INFORMATION: Primer used to make TAJ knock-out mice

<400> SEQUENCE: 21
aggaagagaa tggcagcgaa gagc                                          24

<210> SEQ ID NO 22
<211> LENGTH: 27
<212> TYPE: DNA
<213> ORGANISM: Artificial Sequence
<220> FEATURE:
<223> OTHER INFORMATION: Primer used to make TAJ knock-out mice

<400> SEQUENCE: 22
caagttgatg tcctgaccca aggcacc                                       27
```

```
<210> SEQ ID NO 23
<211> LENGTH: 24
<212> TYPE: DNA
<213> ORGANISM: Artificial Sequence
<220> FEATURE:
<223> OTHER INFORMATION: Primer used to make TAJ knock-out mice

<400> SEQUENCE: 23
agcgcctcgt atggacaaag agtg                                          24

<210> SEQ ID NO 24
<211> LENGTH: 200
<212> TYPE: DNA
<213> ORGANISM: Artificial Sequence
<220> FEATURE:
<223> OTHER INFORMATION: General Structure for an Oligonucleotide used
      in Preparation of an siRNA Molecule
<220> FEATURE:
<221> NAME/KEY: misc_feature
<222> LOCATION: (1)..(200)
<223> OTHER INFORMATION: n is a, c, g, t or u
<220> FEATURE:
<221> NAME/KEY: misc_feature
<222> LOCATION: (2)..(200)
<223> OTHER INFORMATION: nucleotide may be missing

<400> SEQUENCE: 24
nnnnnnnnnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn                                               200

<210> SEQ ID NO 25
<211> LENGTH: 200
<212> TYPE: DNA
<213> ORGANISM: Artificial Sequence
<220> FEATURE:
<223> OTHER INFORMATION: General Structure for an Oligonucleotide used
      in Preparation of an siRNA Molecule
<220> FEATURE:
<221> NAME/KEY: misc_feature
<222> LOCATION: (1)..(200)
<223> OTHER INFORMATION: n is a, c, g, t or u
<220> FEATURE:
<221> NAME/KEY: misc_feature
<222> LOCATION: (2)..(200)
<223> OTHER INFORMATION: nucleotide may be missing

<400> SEQUENCE: 25
nnnnnnnnnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn                                               200
```

METHODS OF PROMOTING NEURITE OUTGROWTH WITH SOLUBLE TAJ POLYPEPTIDES

CROSS REFERENCE TO RELATED APPLICATIONS

The present application claims the benefit of the filing date of U.S. Provisional Application No. 60/598,247 filed Aug. 3, 2004, which is incorporated herein by reference in its entirety.

BACKGROUND OF THE INVENTION

1. Field of the Invention

This invention relates to neurobiology, neurology and pharmacology. More particularly, it relates to methods of modulating neuronal function, e.g., in regulating neuronal growth and/or survival, e.g., axon regeneration and/or neurite outgrowth, e.g., in the CNS, by the administration of TAJ antagonists.

2. Background Art

Nerve cell function is influenced by contact between neurons and other cells in their immediate environment (Rutishauser, et al., 1988, *Physiol. Rev.* 68:819). These cells include specialized glial cells, oligodendrocytes in the central nervous system (CNS), and Schwann cells in the peripheral nervous system (PNS), which sheathe the neuronal axon with myelin (Lemke, 1992, in *An Introduction to Molecular Neurobiology*, Z. Hall, Ed., p. 281, Sinauer).

CNS neurons have the inherent potential to regenerate after injury, but they are inhibited from doing so by inhibitory proteins present in myelin (Brittis et al., 2001, *Neuron* 30:11-14; Jones et al, 2002, *J. Neurosci.* 22:2792-2803; Grimpe et al, 2002, *J. Neurosci.*:22:3144-3160). Several myelin inhibitory proteins found on oligodendrocytes have been characterized. Examples of myelin inhibitory proteins include NogoA (Chen et al., *Nature*, 2000, 403, 434-439; Grandpre et al., *Nature* 2000, 403, 439-444), myelin associated glycoprotein (MAG) (McKerracher et al., 1994, *Neuron* 13:805-811; Mukhopadhyay et al., 1994, *Neuron* 13:757-767) and oligodendrocyte glycoprotein (OM-gp), Mikol et al., 1988, *J. Cell. Biol.* 106:1273-1279). Each of these proteins has been separately shown to be a ligand for the neuronal NgR1 (Wang et al., *Nature* 2002, 417, 941-944; Grandpre et al., *Nature* 2000, 403, 439-444; Chen et al., *Nature,* 2000, 403, 434-439; Domeniconi et al., *Neuron* 2002, published online Jun. 28, 2002).

BRIEF SUMMARY OF THE INVENTION

The invention is based, in part, on the discovery that the TNFR superfamily member TAJ (also known as TRAIN, TROY, TRADE or TNFRSF19, see, e.g., Eby et al., 2000, *J. Biolog. Chem.* 275:15336-15342; Kojima et al., 2000, *J. Biol. Chem* 275:20742-20747) is involved in modulating neuronal function, e.g., in regulating neuronal growth and/or survival, e.g., axon regeneration and/or neurite outgrowth, e.g., in the CNS. While not bound by theory, it is believed that TAJ associates with Nogo receptor (NgR1)/LINGO-1 complex to effect Rho activation, which mediates myelin inhibitory effects on neurite outgrowth. Accordingly, the present invention features, inter alia, methods and compositions that use agents (e.g., protein or polynucleotide agents) that modulate TAJ for modulating neural growth, e.g., for promoting neuronal regeneration, e.g., after CNS injury or inflammation.

Accordingly, in one aspect, the invention features a method of modulating growth and/or survival of a neuron, e.g., modulating axon regeneration and/or neurite outgrowth. The method involves contacting a neuron (such as a CNS neuron) with an effective amount of an agent that modulates TAJ complex formation and/or signaling. In a preferred embodiment, the neuron is a CNS neuron. The contacting can be performed in vitro, ex vivo, or in vivo.

In one embodiment, the agent reduces, e.g., blocks, TAJ signaling and/or complex formation (e.g., reduces TAJ/NgR1 and/or TAJ/LINGO-1 complex formation), to thereby promote outgrowth and/or survival of the neuron, e.g., to increase neuronal survival, neurite outgrowth, axon regeneration, and/or reduce myelin-induced inhibition of neurite growth. Such agents are referred to herein as "TAJ antagonists." Exemplary TAJ antagonists include certain TAJ polypeptides and fusion proteins (e.g., soluble TAJ-Fc fusion proteins or dominant negative (e.g., non-signaling) TAJ polypeptide mutants), inhibitory anti-TAJ antibodies (including antigen-binding fragments and homologs thereof), and inhibitory TAJ nucleic acids, e.g., antisense oligonucleotides, and RNAi nucleic acids (e.g., a TAJ-specific siRNA). TAJ signaling and/or complex formation can also be reduced by decreasing the level of expression of an endogenous TAJ gene, e.g., by decreasing transcription of the TAJ gene. In one embodiment, transcription of the TAJ gene can be decreased by: altering the regulatory sequences of the endogenous TAJ gene, e.g., by the addition of a negative regulatory sequence (such as a DNA-binding site for a transcriptional repressor), or by the removal of a positive regulatory sequence (such as an enhancer or a DNA-binding site for a transcriptional activator).

In a preferred embodiment, neuronal survival, neurite outgrowth, and/or axonal regeneration is increased by at least 10%, preferably by at least 15%, 20%, 25%, 30%, 40%, 50% or more, compared to a reference value, e.g., a control.

In another embodiment, the agent increases TAJ signaling and/or TAJ complex formation to thereby decrease neuronal survival, axon regeneration, or neurite outgrowth. Such agents are referred to herein as "TAJ agonists." Examples of such agents include full length TAJ polypeptides or a functional equivalents thereof, and TAJ-encoding nucleic acids. A TAJ-encoding nucleic acid can be a genomic sequence or a cDNA sequence. The nucleotide sequence can include, in addition to a TAJ coding region (e.g., a full length coding region), a promoter sequence, e.g., a promoter sequence from the TAJ gene or from another gene; an enhancer sequence; untranslated regulatory sequences, e.g., a 5' untranslated region (UTR), e.g., a 5' UTR from the TAJ gene or from another gene, a 3' UTR, e.g., a 3' UTR from the TAJ gene or from another gene; a polyadenylation site; an insulator sequence. In another embodiment, the level of TAJ protein is increased by increasing the level of expression of an endogenous TAJ gene, e.g., by increasing transcription of the TAJ gene. In such an embodiment, transcription of the TAJ gene can be increased by: altering the regulatory sequence of the endogenous TAJ gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the TAJ gene to be transcribed more efficiently.

The methods described herein are useful for, e.g., inhibiting growth cone collapse of a CNS neuron, promoting survival of a neuron (e.g., a neuron at risk of dying), promoting neurite outgrowth, promoting axonal regeneration, promoting myelination at the site of a CNS disorder or injury, decreasing inhibition of axonal growth by a myelin inhibitory protein, and treating a CNS condition in a mammal (e.g., treating a CNS injury or disorder, e.g., treating a CNS condition related to axonal injury or transection, such as traumatic brain injury and spinal cord injury, or treating a neurodegenerative condition such as multiple sclerosis (and other myelination disorders, e.g., progressive multifocal leukoencephalopathy (PML), central pontine myelinolysis (CPM), and leukodystrophies), ALS, Huntington's disease, Alzheimer's disease, Parkinson's disease, diabetic neuropathy, and stroke.

In another aspect, the invention features a method of treating a subject (e.g., a mammal, preferably a human) in need of modulating neuronal growth, e.g., a subject in need of increasing neuronal survival, neurite outgrowth, and/or axon regeneration, preferably in the CNS. The method includes administering to the subject an agent that reduces TAJ signaling and/or reduces TAJ complex formation (e.g., reduces TAJ/NgR1/LINGO-1 complex formation) in an amount sufficient to increase neuronal survival, neurite outgrowth, and/or axon regeneration (e.g., to reduce myelin or MAIF-induced inhibition of neurite outgrowth). The agent can be, e.g., an anti-TAJ inhibitory antibody (or antigen-binding fragment or homologue thereof), a soluble TAJ polypeptide, e.g., a soluble TAJ fusion protein (preferably a TAJ-Fc fusion protein), a TAJ antisense nucleic acid or RNAi molecule. A preferred agent is a protein, e.g., a soluble TAJ-Fc fusion protein, e.g., a fusion protein that includes a soluble extracellular domain of human TAJ fused to a human Ig Fc region, or an inhibitory anti-TAJ antibody, preferably a humanized or fully human anti-TAJ antibody.

In one embodiment, the subject has a CNS neurodegenerative condition such as multiple sclerosis (or other myelination disorder, e.g., progressive multifocal leukoencephalopathy (PML), central pontine myelinolysis (CPM), and leukodystrophy), ALS, Huntington's disease, Alzheimer's disease, Parkinson's disease, diabetic neuropathy. In another embodiment, the subject has a CNS injury related to axonal injury or transection, such as traumatic brain injury, stroke, spinal cord injury, or optic nerve injury. In some embodiments, the agent can be administered within a short period of time after the initial injury, e.g., within 72 hours, preferably within 48 hours, more preferably within 24 hours of the injury. In such embodiments, the agent can be administered systemically but is preferably administered locally, at or near the site of the injury.

In one embodiment, the method can include administering the agent to the subject systemically, e.g., by intravenous, or intramuscular route. In other embodiments, the agent is administered locally, at or near the site of the injury or disorder, e.g., intrathecally or by epidural.

For local administration, the therapeutically effective amount of the polypeptide is typically from 10 µg/kg to 10 mg/kg, e.g., from 10 µg/kg to 5 mg/kg. For systemic administration, the therapeutically effective amount of the polypeptide is typically from 1 mg/kg to 20 mg/kg.

In some embodiments, the method includes (a) providing a cultured host cell genetically engineered to express a TAJ polypeptide; and (b) introducing the host cell into the subject at or near the site of the CNS disease, disorder or injury, e.g., spinal cord injury. The cultured host cell can be autologous or allogeneic. In one embodiment, the cell has been transfected with a TAJ polypeptide-encoding nucleic acid. The TAJ polypeptide can be a full-length TAJ polypeptide.

In some embodiments, the method includes the steps of administering to the subject, at or near the site of the disease, disorder or injury, a vector (e.g., a viral vector) containing a nucleotide sequence that causes the expression of a TAJ polypeptide (e.g., a nucleotide sequence that encodes a TAJ polypeptide) so that the TAJ polypeptide is expressed from the nucleotide sequence in the subject in an amount sufficient to reduce inhibition of axonal extension by neurons at or near the site of the injury. The vector can be, e.g., an adenoviral vector, a lentiviral vector, a baculoviral vector, an Epstein Barr viral vector, a papovaviral vector, a vaccinia viral vector, a herpes simplex viral vector, or a plasmid vector. The vector can be administered by a route such as topical administration, intraocular administration, parenteral administration, intrathecal administration, subdural administration or subcutaneous administration.

In some embodiments, the agent is administered in combination with a second prophylactic or therapeutic agent, e.g., a corticosteroid, e.g., methylprednisolone; an analgesic; an antibiotic; a second biologic therapeutic, e.g., a modulator of LINGO-1 activity, p75 activity, or Nogo receptor (NgR) activity. In some cases, the agent may be conjugated to the second agent.

In typical embodiments, administration of the agent is repeated, e.g., is repeated at least 1, 2, 3, 5, 10, 20 or more times. In one embodiment, the agent is administered in a treatment course including at least once weekly administration for at least 8 weeks. In other embodiments (for example, where the subject has had an acute CNS injury), the agent is administered in a treatment course including multiple administrations within a single week.

In one embodiment, the method includes evaluating the subject or a biological sample from the subject for a parameter related to neuronal function, e.g., neuronal Rho activation, neuronal outgrowth, spinal chord function and/or cognitive function. The evaluation can be performed before and/or after the administration.

In some embodiments, the agent is delivered to the subject by controlled delivery, using, e.g., a controlled release device such as a biocompatible polymer, microparticle, or mesh. The device can reduce degradation and control the release of the agent. Such a biocompatible controlled release system can be administered to the subject, e.g., by injection or implantation, e.g., intramuscularly, subcutaneously, intravenously, or at or near the site of a CNS lesion.

In another aspect, the invention features a method of screening for an agent that modulates, e.g., increases or decreases, neuronal survival, e.g., modulates neurite outgrowth and/or axon regeneration. The method includes identifying an agent that reduces the expression or levels of TAJ and/or reduces the ability of TAJ to signal or form a complex (e.g., a TAJ/LINGO-1/NgR1 complex). The method can also include correlating the effect of the test agent on TAJ with the test agent's ability to promote or increase neurite outgrowth (e.g., providing print material or a computer readable medium, e.g., informational, marketing or instructional print material or computer readable medium, related to the identified agent or its use). Correlating means identifying a test agent that decreases expression, activity or levels of TAJ as an agent capable of promoting or increasing neurite outgrowth (e.g., promoting axonal regeneration). The correlating step can include, e.g., generating or providing a record (e.g., a print or computer readable record, such as a laboratory record or dataset or an email) identifying a test agent that decreases expression, activity or levels of TAJ as an agent capable of promoting or increasing neuronal growth. The record can include other information, such as a specific test agent identifier, a date, an operator of the method, or information about the source, structure, method of purification or biological activity of the test agent. The record or information derived from the record can be used, e.g., to identify the test agent as a compound or candidate agent (e.g., a lead compound) for pharmaceutical or therapeutic use. The identified agent can be identified as an agent or a potential agent for treatment of a CNS condition, e.g., a CNS condition described herein. Agents, e.g., compounds, identified by this method can be used, e.g., in the treatment (or development of treatments) for modulating neuronal growth.

In one embodiment, the method includes providing a test agent and evaluating whether the test agent binds TAJ or TAJ ligand. In one embodiment, the method includes providing a test agent and evaluating whether the test agent affects the ability of TAJ to bind one or both of LINGO-1 and NgR1.

In one embodiment, the method includes providing a test agent and evaluating whether the test agent affects the ability of TAJ to signal, e.g., to modulate Rho activation in a neuron. For example, one could use a Rho driven reporter system to screen for agents that affect TAJ signaling.

In another embodiment, the method includes: (a) providing a cell (e.g., a CNS cell described herein), tissue or non-human animal harboring an exogenous nucleic acid that includes a regulatory region (e.g., a promoter) of TAJ operably linked to a nucleotide sequence encoding a reporter polypeptide (e.g., a light based, e.g., colorimetric or fluorescently detectable label, e.g., a fluorescent reporter polypeptide, e.g., GFP, EGFP, BFP, RFP); (b) evaluating the ability of a test agent to modulate the activity of the reporter polypeptide in the cell, tissue or non-human animal; and (c) selecting a test agent that increases or decreases the activity of the reporter polypeptide as an agent that inhibits or promotes CNS neuronal growth, respectively. In one embodiment, the cell or tissue is a neuron. In another embodiment, the non-human animal is a transgenic animal, e.g., a transgenic rodent, e.g., a mouse, rat or guinea pig, harboring the nucleic acid. In another embodiment, the non-human animal is a zebrafish (see, e.g., Hjorth, 2002, *Int J Dev Biol.* 46(4):609-19 for axon growth assays in zebrafish), *Drosophila, C. elegans* or other lower organism harboring the nucleic acid. In one embodiment, the cell is a CNS cell, e.g., a CG neuron, DRG neuron, astrocyte or oligodendrocyte.

In some embodiments, the evaluation includes entering a value for the evaluation, e.g., a value for the effect of the test agent on TAJ, into a database or other record.

In one embodiment, the method includes two evaluating steps, e.g., the method includes a first step of evaluating the test agent in a first system, e.g., a cell-free, cell or tissue system, and a second step of evaluating the test agent in a second system, e.g., a second cell or tissue system or in a non-human animal. In other embodiments, the method includes two evaluating steps in the same type of system, e.g., the agent is re-evaluated in a non-human animal after a first evaluation in the same or a different non-human animal. The two evaluations can be separated by any length of time, e.g., days, weeks, months or years. In one embodiment, the test agent is first evaluated for its ability to interact with TAJ, e.g., bind to TAJ, and is then evaluated for its ability to modulate Rho activation and/or neurite outgrowth.

The test agent can be a crude or semi-purified extract (e.g., an organic, e.g., animal or botanical extract) or an isolated compound, e.g., a small molecule, protein, lipid or nucleic acid.

In another aspect, the invention features a transgenic non-human animal, e.g., a transgenic non-human rodent, e.g., a mouse, rat or guinea pig, whose genome comprises a transgene that disrupts the TAJ gene. In one embodiment, the non-human animal (or a cell from the animal) exhibits one or more of: reduced neurite outgrowth inhibition in response to inhibitors of neurite outgrowth (e.g., myelin and MAIF); and reduced Rho activation in response to an inhibitor of neurite outgrowth.

Although methods and materials similar or equivalent to those described herein can be used in the practice or testing of the invention, the preferred methods and materials are described below. The materials, methods and examples are illustrative only, and are not intended to be limiting. Other features and advantages of the invention will be apparent from the detailed description and from the claims.

BRIEF DESCRIPTION OF THE DRAWINGS/FIGURES

FIG. 1A-C shows the results of various binding assays. (A) is a bar graph showing results of an ELISA assay for binding of various proteins to soluble NgR1 (10 ug/ml). (B) is a set of histograms showing binding of AP-TAJ to transfected CHO cells expressing the indicated proteins. (C) is a graph showing results of an ELISA assay for binding of AP-TAJ to NgR1-expressing CHO cells.

Figure 4:
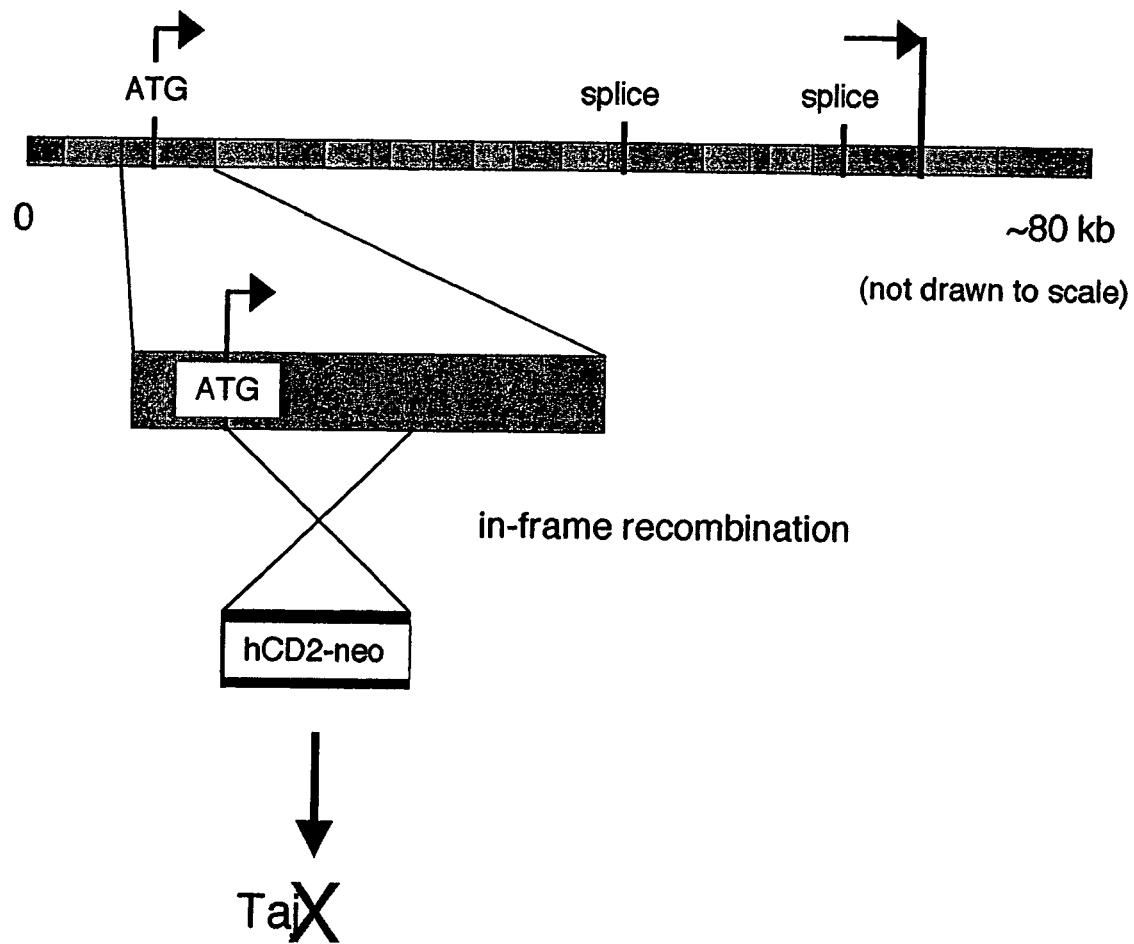

FIG. 4. is a diagram of the TAJ knock-out construct.

FIG. 5A-D is a set of histograms and graphs showing the effects of TAJ on neurite outgrowth. (A) P8 cerebellar granule neurons (CGNs) from TAJ knockout and wild-type mice plated onto myelin-coated slides. (B) Measurement of neurite outgrowth in wildtype CGNs in the absence and presence of TAJ 1 day after plating. (C) Measurement of neurite length from TAJ wildtype and knockout CGNs in respective myelin dose-response curves. (D) Measurement of neurite outgrowth (after 24 hours in vitro) in dissociated DRG neurons from postnatal day 7 rats grown on a substrate of poly-D-lysine (PDL) and AP-Nogo66 (with and without TAJ-Fc as indicated).

Figure 6:
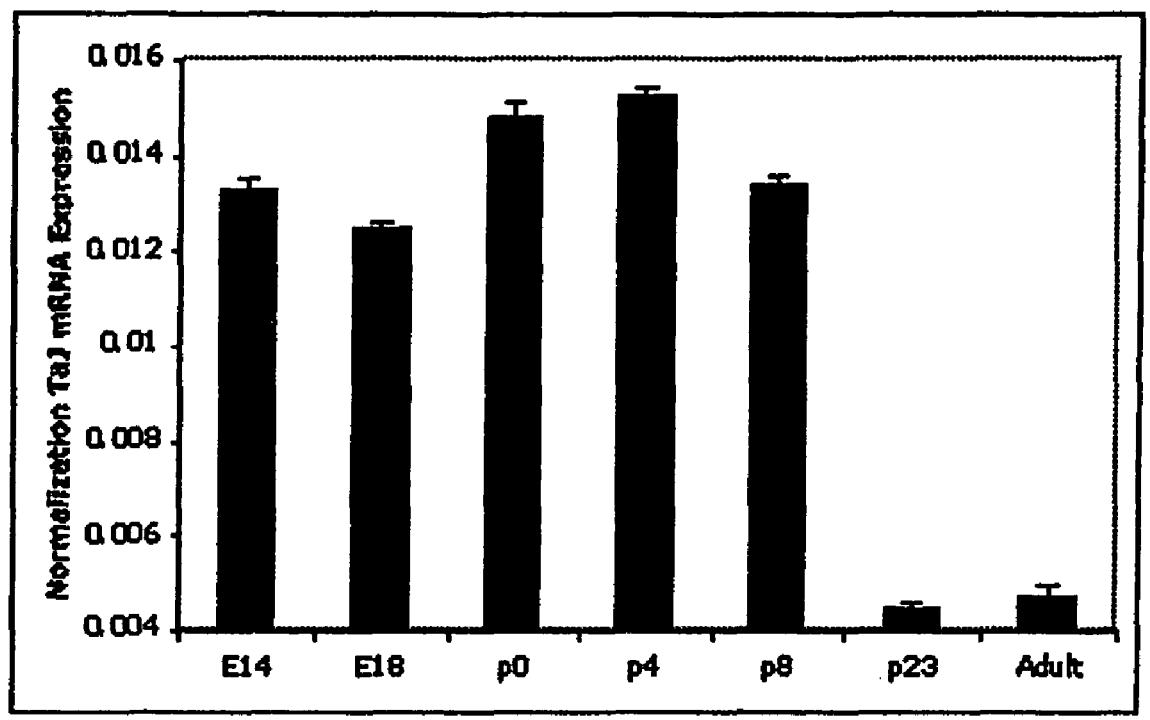

FIG. 6 is a graph showing relative levels of expression of TAJ in whole rat brain homogenates taken over a developmental timecourse spanning E14, E18, P0, P4, P8, P11, P23, and adult (E=embryonic day and P=Post-natal day).

DETAILED DESCRIPTION OF THE INVENTION

Following axon injury or transection, neurons in the peripheral nervous system (PNS) are able to regrow and repair their axons to the extent that functional connections are reestablished. In contrast, neurons of the central nervous system (CNS) lack this restorative ability, and the mechanisms responsible for the inhibition of CNS regeneration remain the subject of intense investigation. Importantly, the described ability of CNS neurons to regrow their axons in a PNS environment indicates that there is not an inherent inability of CNS neurons to regenerate following injury. Instead, it appears that inhibition of CNS axon repair is the result of interactions between the neuronal process and its local CNS environment. Studies suggest that a significant contributor to these negative interactions is a group of inhibitory molecules that are associated with myelin, namely myelin-associated glycoprotein (MAG), Nogo, and oligodendrocyte-myelin glycoprotein (OMgp). Each of these proteins has been shown to negatively affect growth cone extension and axon outgrowth.

Further investigations into Nogo, MAG, and OMgp (collectively referred to as myelin-associated inhibitory factors, or MAIFs) has indicated that the outgrowth-inhibitory signal of these proteins is transduced by a common multifactorial receptor complex. At least three different subunits can participate in the MAIF receptor complex: Nogo receptor 1 (NgR1), p75, and LINGO-1. See Fournier, A. E., et al. *Nature* 409:341-346 (2001); Mi, S., et al. *Nat. Neurosci.* 7:221-228 (2004); and Wang, K. C., et al., *Nature* 420:74-78 (2002) While these three molecules combine to form a functional MAIF receptor, they are highly different from each other in their respective physical characteristics. NgR1 is a member of the leucine-rich-repeat (LRR) superfamily of molecules and is GPI-linked to the cell surface. See Fournier, A. E., et al. *Nature* 409:341-346 (2001). p75 is a member of the tumor necrosis factor receptor (TNFR) superfamily, yet was originally identified as a low-affinity neurotrophin receptor that has since been found to play important roles in cell death signaling as well. See Rabizadeh, S. and Bredesen, D. E. *Cytokine Growth Factor Rev.* 14:225-239 (2003). LINGO-1, the most recently described member of the MAIF receptor complex, is also an LRR family member yet contains a transmembrane and cytoplasmic domain that is capable of tyrosine phosphorylation and downstream signaling. See Mi, S., et al. *Nat. Neurosci.* 7:221-228 (2004).

Extensive in vitro analysis has shown that each of the three receptor components, NgR1, p75, and LINGO-1, contribute to a fully functional MAIF receptor complex. However, other lines of evidence suggest that p75 may not play as important a role in axon outgrowth inhibition under more physiological conditions. Axons in the corticospinal tract are highly responsive to MAIFs, yet corticospinal neurons do not normally express appreciable levels of p75. p75 is expressed by ascending sensory neurons, yet the loss of p75 in these neurons by gene knockout failed to promote the regeneration of these axons following dorsal column lesion. Lastly, p75 binding to NgR1 is relatively weak compared to LINGO-1/NgR1 binding (this paper), with p75/NgR1 affinity being markedly increased by the presence of ligand. See, e.g., Copray, S., et al., *J. Neuroimmunol.* 148:41-53 (2004); Giehl, K. M., et al., *J. Neurosci.* 21:3492-3502 (2001); Mi, S., et al. *Nat. Neurosci.* 7:221-228 (2004); Shao, Z., et al., *Neuron* 45:353-359 (2004); and Song, X. Y., et al., *J. Neurosci.* 24:542-546 (2004).

The methods and compositions described herein relate to a role for TAJ (a TNF receptor superfamily member) in neuronal survival and/or growth, e.g., in neurite outgrowth in the CNS. As described herein, TAJ binds NgR1 and is expressed in a variety of cell types in multiple brain regions. TAJ forms a functional MAIF receptor complex with NgR1 and LINGO-1. Neurons cultured from mice lacking TAJ expression show reduced outgrowth inhibition in response to myelin and MAIF. Thus, TAJ participates in the MAIF receptor complex and plays a role in mediating the inhibitory influences of the MAIFs. Accordingly, TAJ reagents such as TAJ polypeptides (e.g., soluble TAJ polypeptides and fusion proteins), anti-TAJ antibodies, and TAJ nucleic acids (e.g., nucleic acids encoding TAJ or antisense TAJ nucleic acids) can be used to modulate neurite outgrowth, e.g., to treat various CNS conditions, e.g., traumatic spinal cord injury, stroke, and multiple sclerosis (MS).

Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

In order to further define this invention, the following terms and definitions are provided.

It is to be noted that the term "a" or "an" entity, refers to one or more of that entity; for example, "an immunoglobulin molecule," is understood to represent one or more immunoglobulin molecules. As such, the terms "a" (or "an"), "one or more," and "at least one" can be used interchangeably herein.

Throughout this specification and claims, the word "comprise," or variations such as "comprises" or "comprising," indicate the inclusion of any recited integer or group of integers but not the exclusion of any other integer or group of integers in the specified method, structure, or composition.

As used herein, the term "consists of," or variations such as "consist of" or "consisting of," as used throughout the specification and claims, indicate the inclusion of any recited integer or group of integers, but that no additional integer or group of integers may be added to the specified method, structure or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

In the present invention, a polypeptide can be composed of amino acids joined to each other by peptide bonds or modified peptide bonds, i.e., peptide isosteres, and may contain amino acids other than the 20 gene-encoded amino acids (e.g. non-naturally occuring amino acids). The polypeptides of the present invention may be modified by either natural processes, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure And Molecular Properties, 2nd Ed., T. E. Creighton, W.H. Freeman and Company, New York (1993); Posttranslational Covalent Modification of Proteins, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992).)

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

In the present invention, a "polypeptide fragment" refers to a short amino acid sequence of a larger polypeptide. Protein fragments may be "free-standing," or comprised within a larger polypeptide of which the fragment forms a part of region. Representative examples of polypeptide fragments of the invention, include, for example, fragments comprising about 5 amino acids, about 10 amino acids, about 15 amino acids, about 20 amino acids, about 30 amino acids, about 40 amino acids, about 50 amino acids, about 60 amino acids, about 70 amino acids, about 80 amino acids, about 90 amino acids, and about 100 amino acids or more in length.

The terms "fragment," "variant," "derivative" and "analog" when referring to a polypeptide of the present invention include any polypeptide which retains at least some biological activity. Polypeptides as described herein may include fragment, variant, or derivative molecules therein without limitation, so long as the polypeptide still serves its function. NgR1 polypeptides and polypeptide fragments of the present invention may include proteolytic fragments, deletion fragments and in particular, fragments which more easily reach the site of action when delivered to an animal. Polypeptide fragments further include any portion of the polypeptide which comprises an antigenic or immunogenic epitope of the native polypeptide, including linear as well as three-dimensional epitopes. NgR1 polypeptides and polypeptide fragments of the present invention may comprise variant regions, including fragments as described above, and also polypeptides with altered amino acid sequences due to amino acid substitutions, deletions, or insertions. Variants may occur naturally, such as an allelic variant. By an "allelic variant" is intended alternate forms of a gene occupying a given locus on a chromosome of an organism. *Genes II*, Lewin, B., ed., John Wiley & Sons, New York (1985). Non-naturally occurring variants may be produced using art-known mutagenesis techniques. NgR1 polypeptides and polypeptide fragments of the invention may comprise conservative or non-conservative amino acid substitutions, deletions or additions. NgR1 polypeptides and polypeptide fragments of the present invention may also include derivative molecules. Variant polypeptides may also be referred to herein as "polypeptide analogs." As used herein a "derivative" of a polypeptide or a polypeptide fragment refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

As used herein the term "disulfide bond" includes the covalent bond formed between two sulfur atoms. The amino acid cysteine comprises a thiol group that can form a disulfide bond or bridge with a second thiol group.

As used herein, "fusion protein" means a protein comprising a first polypeptide linearly connected, via peptide bonds, to a second, polypeptide. The first polypeptide and the second polypeptide may be identical or different, and they may be directly connected, or connected via a peptide linker (see below).

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). A polynucleotide can contain the nucleotide sequence of the full length cDNA sequence, including the untranslated 5' and 3' sequences, the coding sequences, as well as fragments, epitopes, domains, and variants of the nucleic acid sequence. The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotides can be composed of triple-stranded regions comprising RNA or DNA or both RNA and DNA. polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The term "nucleic acid" refer to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a TAJ polypeptide or polypeptide fragment of the invention contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a TAJ polypeptide or polypeptide fragment of the present invention. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

In certain embodiments, agents for use in the methods disclosed herein are "antibody" or "immunoglobulin" molecules, or immunospecific fragments thereof, e.g., naturally occurring antibody or immunoglobulin molecules or engineered antibody molecules or fragments that bind antigen in a manner similar to antibody molecules. As used herein, the term "antibody" is used in the broadest sense and covers polyclonal as well as monoclonal antibodies, including full length antibodies, multispecific antibodies (e.g., bispecific antibodies), chimeric, humanized and fully human antibodies, and fragments of such antibodies including Fab, Fab', F(ab')2, and Fv fragments, diabodies, linear antibodies, single-chain antibody molecules, and multispecific antibodies formed from antibody fragments, so long as they exhibit the desired antigen-binding activity. A monoclonal antibody indicates the character of the antibody as being a substantially homogeneous population of antibodies, and is not to be construed as requiring production of the antibody by any particular method.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., *Antibodies: A Laboratory Manual*, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma, \mu, \alpha, \delta, \epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain ($C_H1$, $C_H2$ or $C_H3$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_H3$ and $C_L$ domains actually comprise the carboxy-terminus of the heavy and light chain, respectively.

Light chains are classified as either kappa or lambda ($\kappa, \lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, ($\gamma, \mu, \alpha, \delta, \epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention.

As indicated above, the variable region allows the antibody to selectively recognize and specifically bind epitopes on antigens. That is, the $V_L$ domain and $V_H$ domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the $V_H$ and $V_L$ chains. In some instances, e.g., certain immunoglobulin molecules derived from camelid species or engineered based on camelid immunoglobulins, a complete immunoglobulin molecule may consist of heavy chains only, with no light chains. See, e.g., Hamers Casterman et al., *Nature* 363:446 448 (1993).

In one embodiment, an antigen binding molecule of the invention comprises at least one heavy or light chain CDR of an antibody molecule. In another embodiment, an antigen binding molecule of the invention comprises at least two CDRs from one or more antibody molecules. In another embodiment, an antigen binding molecule of the invention comprises at least three CDRs from one or more antibody molecules. In another embodiment, an antigen binding molecule of the invention comprises at least four CDRs from one or more antibody molecules. In another embodiment, an antigen binding molecule of the invention comprises at least five CDRs from one or more antibody molecules. In another embodiment, an antigen binding molecule of the invention comprises at least six CDRs from one or more antibody molecules. Exemplary antibody molecules comprising at least one CDR that can be included in the subject antigen binding molecules are known in the art and exemplary molecules are described herein.

Antibodies or immunospecific fragments thereof for use in the methods of the invention include, but are not limited to, polyclonal, monoclonal, multispecific, human, humanized, primatized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to binding molecules disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antibody fragments, including single-chain antibodies, may comprise the variable region(s) alone or in combination with the entirety or a portion of the following: hinge region, $C_H1$, $C_H2$, and $C_H3$ domains. Also included in the invention are antigen-binding fragments also comprising any combination of variable region(s) with a hinge region, $CH_1$, $C_H2$, and $C_H3$ domains. Antibodies or immunospecific fragments thereof for use in the diagnostic and therapeutic methods disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain. A polypeptide comprising a heavy chain portion comprises at least one of: a $C_H1$ domain, a hinge (e.g., upper, middle, and/or lower hinge region) domain, a $C_H2$ domain, a $C_H3$ domain, or a variant or fragment thereof. For example, a binding polypeptide for use in the invention may comprise a polypeptide chain comprising a $C_H1$ domain; a polypeptide chain comprising a $C_H1$ domain, at least a portion of a hinge domain, and a $C_H2$ domain; a polypeptide chain comprising a $C_H1$ domain and a $C_H3$ domain; a polypeptide chain comprising a $C_H1$ domain, at least a portion of a hinge domain, and a $C_H3$ domain, or a polypeptide chain comprising a $C_H1$ domain, at least a portion of a hinge domain, a $C_H2$ domain, and a $C_H3$ domain. In another embodiment, a polypeptide of the invention comprises a polypeptide chain comprising a $C_H3$ domain. Further, a binding polypeptide for use in the invention may lack at least a portion of a $C_H2$ domain (e.g., all or part of a $C_H2$ domain). As set forth above, it will be understood by one of ordinary skill in the art that these domains (e.g., the heavy chain portions) may be modified such that they vary in amino acid sequence from the naturally occurring immunoglobulin molecule.

In certain TAJ antagonist antibodies or immunospecific fragments thereof for use in the treatment methods disclosed herein, the heavy chain portions of one polypeptide chain of a multimer are identical to those on a second polypeptide chain of the multimer. Alternatively, heavy chain portion-containing monomers for use in the methods of the invention are not identical. For example, each monomer may comprise a different target binding site, forming, for example, a bispecific antibody.

The heavy chain portions of a binding polypeptide for use in the methods disclosed herein may be derived from different immunoglobulin molecules. For example, a heavy chain portion of a polypeptide may comprise a $C_H1$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a $V_L$ or $C_L$ domain.

Antibodies or immunospecific fragments thereof for use in the treatment methods disclosed herein act as antagonists of TAJ as described herein. For example, an antibody for use in the methods of the present invention may function as an antagonist, blocking or inhibiting the suppressive activity of the TAJ polypeptide.

An isolated nucleic acid molecule encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

Anti-TAJ antibodies, or antigen-binding fragments, variants, or derivatives thereof disclosed herein may be described or specified in terms of the epitope(s) or portion(s) of an antigen, e.g., a target polypeptide (TAJ) that they recognize or specifically bind. The portion of a target polypeptide which specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or include non-polypeptide elements, e.g., an "epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, peptide or polypeptide epitope recognized by anti-TAJ antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of TAJ, e.g., SEQ ID NO:2.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

An antibody or or antigen-binding fragment, variant, or derivative disclosed herein may be said to bind a target polypeptide disclosed herein or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, an antibody of the invention may be said to bind a target polypeptide disclosed herein or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-5} \times 10^{-6}$ sec$^{-1}$, $10^{-6}$ sec$^{-1}$, $5 \times 10^{-7}$ sec$^{-1}$ or $10^{-7}$ sec$^{-1}$.

An antibody or or antigen-binding fragment, variant, or derivative disclosed herein may be said to bind a target polypeptide disclosed herein or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. More preferably, an antibody of the invention may be said to bind a target polypeptide disclosed herein or a fragment or variant thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-TAJ antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Antibodies or immunospecific fragments thereof for use in the treatment methods disclosed herein may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

Anti-TAJ antibodies or antigen-binding fragments, variants or derivatives thereof of the invention may be "multispecific," e.g., bispecific, trispecific or of greater multispecificity, meaning that it recognizes and binds to two or more different epitopes present on one or more different antigens (e.g., proteins) at the same time. Thus, whether an anti-TAJ antibody is "monospecfic" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains, present in an Anti-TAJ antibody, binding polypeptide or antibody. Each binding domain specifically binds one epitope. When an anti-TAJ antibody or binding polypeptide comprises more than one binding domain, each binding domain may specifically bind the same epitope, for an antibody with two binding domains, termed "bivalent monospecific," or to different epitopes, for an antibody with two binding domains, termed "bivalent bispecific." An antibody may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Appl. Publ. Nos. 2003/020734 and 2002/0155537, the disclosures of all of which are incoporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "$C_H1$ domain" includes the first (most amino terminal) constant region domain of an immunoglobulin heavy chain. The $C_H1$ domain is adjacent to the $V_H$ domain and is amino terminal to the hinge region of an immunoglobulin heavy chain molecule.

As used herein the term "$C_H2$ domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit. The $C_H2$ domain is unique in that it is not closely paired with another domain. Rather, two N-linked branched carbohydrate chains are interposed between the two $C_H2$ domains of an intact native IgG molecule. It is also well documented that the $C_H3$ domain extends from the $C_H2$ domain to the C-terminal of the IgG molecule and comprises approximately 108 residues.

As used herein, the term "hinge region" includes the portion of a heavy chain molecule that joins the $C_H1$ domain to the $C_H2$ domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the $C_H1$ and $C_L$ regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein, the terms "linked," "fused" or "fusion" are used interchangeably. These terms refer to the joining together of two more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

A "linker" sequence is a series of one or more amino acids separating two polypeptide coding regions in a fusion protein. A typical linker comprises at least 5 amino acids. Additional linkers comprise at least 10 or at least 15 amino acids. In certain embodiments, the amino acids of a peptide linker are selected so that the linker is hydrophilic. The linker (Gly-Gly-Gly-Gly-Ser)$_3$ (SEQ ID NO: 7) is a preferred linker that is widely applicable to many antibodies as it provides sufficient flexibility. Other linkers include Glu Ser Gly Arg Ser Gly Gly Gly Gly Ser Gly Gly Gly Gly Ser (SEQ ID NO: 8), Glu Gly Lys Ser Ser Gly Ser Gly Ser Glu Ser Lys Ser Thr (SEQ ID NO: 9), Glu Gly Lys Ser Ser Gly Ser Gly Ser Glu Ser Lys Ser Thr Gln (SEQ ID NO: 10), Glu Gly Lys Ser Ser Gly Ser Gly Ser Glu Ser Lys Val Asp (SEQ ID NO: 11), Gly Ser Thr Ser Gly Ser Gly Lys Ser Ser Glu Gly Lys Gly (SEQ ID NO: 12), Lys Glu Ser Gly Ser Val Ser Ser Glu Gln Leu Ala Gln Phe Arg Ser Leu Asp (SEQ ID NO: 13), and Glu Ser Gly Ser Val Ser Ser Glu Glu Leu Ala Phe Arg Ser Leu Asp (SEQ ID NO: 14). Examples of shorter linkers include fragments of the above linkers, and examples of longer linkers include combinations of the linkers above, combinations of fragments of the linkers above, and combinations of the linkers above with fragments of the linkers above.

As used herein the term "properly folded polypeptide" includes polypeptides (e.g., Anti-TAJ antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product and the translation of such mRNA into polypeptide(s). If the final desired product is biochemical, expression includes the creation of that biochemical and any precursors.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject.

As used herein, phrases such as "a subject that would benefit from administration of a TAJ polypeptide or polypeptide fragment of the present invention" and "an animal in need of treatment" includes subjects, such as mammalian subjects, that would benefit from administration of a TAJ polypeptide or polypeptide fragment of the present invention used, e.g., for detection (e.g., for a diagnostic procedure) and/or for treatment, i.e., palliation or prevention of a disease such as MS, with a TAJ polypeptide or polypeptide fragment of the present invention. As described in more detail herein, the polypeptide or polypeptide fragment can be used in unconjugated form or can be conjugated, e.g., to a drug, prodrug, or an isotope.

As used herein, a "therapeutically effective amount" refers to an amount effective, at dosages and for periods of time necessary, to achieve a desired therapeutic result. A therapeutic result may be, e.g., lessening of symptoms, prolonged survival, improved mobility, and the like. A therapeutic result need not be a "cure".

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

TAJ (TROY)

The invention is based on the discovery certain modulators of TAJ signaling activity in the CNS may affect neuronal survival and/or outgrowth.

As used herein, a "TAJ polypeptide" is a polypeptide that includes a full length TAJ amino acid sequence or a functional fragment or domain thereof. A TAJ polypeptide can also optionally include a heterologous (non-TAJ) amino acid sequence.

A naturally occurring full length human TAJ polypeptide is 423 amino acids in length with a calculated molecular mass of 46 kDa. The amino acid sequence of this human TAJ polypeptide is shown below (SEQ ID NO:2) This human TAJ polypeptide is encoded by the cDNA of SEQ ID NO:1.

```
  1 MALKVLLEQE KTFFTLLVLL GYLSCKVTCE SGDCRQQEFR DRSGNCVPCN QCGPGMELSK

61 ECGFGYGEDA QCVACRLHRF KEDWGFQKCK PCLDCAVVNR FQKANCSATS DAICGDCLPG

121 FYRKTKLVGF QDMECVPCGD PPPPYEPHCA SKVNLVKIAS TASSPRDTAL AAVICSALAT

181 VLLALLILCV IYCKRQFMEK KPSWSLRSQD IQYNETELSC FDRPQLHEYA HRACCQCRRD

241 SVQTCGPVRL LPSMCCEEAC SPNPATLGCG VHSAASLQAR NAGPAGEMVP TFFGSLTQSI

301 CGEFSDAWPL MQNPMGGDNI SFCDSYPELT GEDIHSLNPE LESSTSLDSN SSQDLVGGAV

361 PVQSHSENFT AATDLSRYNN TLVESASTQD ALTMRSQLDQ ESGAVIHPAT QTSLQVRQRL

421 GSL
```

See, e.g., Eby, M. T., et al., *J. Biol. Chem.* 275:15336-15342 (2000).

Naturally occurring variants of human TAJ are known, for example, GenBank Accession Number BAB03269 (SEQ ID NO:4), encoded by the cDNA having GenBank Accession Number AB040434 (SEQ ID NO:3), GenBank Accession Number AAK28396 (SEQ ID NO:6), encoded by the cDNA having GenBank Accession Number AF246999 (SEQ ID NO:5).

Other naturally occurring human TAJ polypeptides include alternative splicing forms. Naturally occurring TAJ polypeptides include the alternatively spliced forms of the same gene. One alternative splicing form is similar to amino acids 1 to 417 of SEQ ID NO:2. The messenger RNA encoding this splice variant has a unique 5' UTR and differs in the 3' end-region which includes a part of the coding sequence, as compared to SEQ ID NO:2. The resulting variant has a distinct and shorter C-terminus, as compared to SEQ ID NO:2. See, e.g., GenBank Accession No. AAH47321 (SEQ ID NO: 16), encoded by the cDNA having GenBank Accession No: BC047321 (SEQ ID NO: 15).

Other related sequences include homologs in other species, e.g., mouse TRADE (GenBank Accession NO: AAK28397 (SEQ ID NO: 18), encoded by the cDNA of GenBank Accession No: AF247000 (SEQ ID NO: 17)).

The human TAJ polypeptide of SEQ ID NO:2 comprises a signal peptide sequence, an extracellular domain, a transmembrane domain, and a cytoplasmic domain. The signal peptide sequence of TAJ polypeptide spans from amino acid 1 to about amino acid 25 of SEQ ID NO:2, the extracellular domain spans from about amino acids 26 to about amino acid 173 of SEQ ID NO:2. The transmembrane domain spans from about amino acid 174 of SEQ ID NO:2 to about amino acid 190 of SEQ ID NO:2, and the cytoplasmic domain spans from about amino acid 191 to amino acid 423 of SEQ ID NO:2. Of course, the skilled artisan realizes that the ends of the predicted domains are approximate. For example, the signal peptide sequence may contain amino acids 1 to 20, 1 to 21, 1 to 22, 1 to 23, 1 to 24, 1 to 25, 1 to 26, 1 to 27, 1 to 28, 1 to 29, or 1 to 30 of SEQ ID NO:2. Accordingly, the N-terminus of the extracellular domain of human TAJ would be at amino acid 21 to amino acid 31, of SEQ ID NO:2, respectively. Table 2 lists the approximate domains and other regions of the human TAJ polypeptide of SEQ ID NO:2. Similar domain fragments for other TAJ polypeptides, such as those disclosed herein, are easily deduced by one of ordinary skill in the art.

Like other members of the TNF-receptor superfamily, the extracellular domain of TAJ characterized by the presence of cysteine rich domains ("CRDs"). CRDs are pseudo-repeats typically containing six cysteine residues. While not being bound by theory, CRDs are believed to be engaged in the formation of three intradomain disulfide bonds important for ligand binding. CRDs may also contain less than six cysteines, forming incomplete cysteine rich motif. The number of CRDs in a given receptor varies from one to four. See Banner et al., *Cell*, 1993, 73:431-445.

TNF family receptors have functional domain structure such that one receptor extracellular domain is comprised of multiple TNF receptor domains (i.e., CRDs) (for a review, see Bodmer et al., 2002, *TRENDS in Biochem. Sci.* 27:19-26). In one embodiment, a soluble TAJ polypeptide comprises one or more (e.g, 1 or 2) but not all of the TNF receptor domains of full length TAJ polypeptide. Such a truncated soluble TAJ polypeptide comprises a subset of its TNF receptor domains sufficient to form an interaction site for NgR1 and/or LINGO-1.

The TAJ polypeptide of SEQ ID NO:2 is believed to contain three cysteine rich domains. Two CRD domains have six cysteines in the region, and one CRD has only four cysteines. Thus, the TAJ polypeptide contains two perfect TNF receptor motifs, CRD1 and CRD2 herein, and one imperfect motif, CRD3, in which C2 and C6 are not present.

The approximate coordinates of these domains are shown in Table 2.

TABLE 2

| Domain or Region | Beginning Residue | Ending Residue |
|---|---|---|
| Signal Sequence | 1 | 25 |
| N-terminal EC region | 26 | 32 |
| CRD 1 | 33 | 73 |
| CRD 2 | 74 | 115 |
| CRD 3 | 116 | 160 |
| C-terminal EC region | 161 | 173 |
| Transmembrane domain | 174 | 190 |
| Cytoplasmic domain | 191 | 423 |

TAJ polypeptides of the present invention may further comprise one or more of the following polypeptide fragments, motifs, or domains: a serine/threonine/proline-rich domain (e.g., about amino acid 137 to about amino acid 168 of SEQ ID NO:2), a TAJ related death effector domain (e.g., about amino acid 218 to about amino acid 423 of SEQ ID NO:2), an N-linked glycosylation site (e.g., amino acids 105-108 of SEQ ID NO:2), a cAMP/cGMP-dependent protein kinase phosphorylation site (e.g., amino acids 200 to 203 of SEQ ID NO:2 or residues 238 to 241 of SEQ ID NO:2), a protein kinase C phosphorylation site (e.g., amino acids 205 to 207 of SEQ ID NO:2), casein kinase II phosphorylation sites (e.g., amino acids 219 to 222 of SEQ ID NO:2 and/or amino acids 325 to 328 of SEQ ID NO:2), a tyrosine kinase phosphorylation site (e.g., amino acids 207 to 213 of SEQ ID NO:2), an N-myristoylation site (e.g., amino acids 215-220 of SEQ ID NO:2), a TRAF binding domain (e.g., amino acids 1-328 of SEQ ID NO:2 or, alternatively, amino acids 218-328 of SEQ ID NO:2), or an NFkB activation signaling domain (e.g., amino acids 1-368 of SEQ ID NO:2, or alternatively amino acids in the cytoplasmic domain of TAJ polypeptides) See Wood et al., U.S. Patent Application Publication No. 2002/0068696A1; see also WO 01/058954 A3, both of which are incorporated herein by reference in their entireties.

As described in more detail elsewhere herein, "soluble TAJ polypeptide" is a polypeptide that includes a fragment of full length TAJ polypeptide that lacks a transmembrane domain and optionally lacks a cytoplasmic domain. A typical soluble TAJ polypeptide includes at least a portion of the extracellular domain of TAJ polypeptide. (The extracellular domain of human TAJ polypeptides includes from about amino acid 26 to about amino acid 173 of SEQ ID NO:2, see Table 2). The term "about" is intended to indicate the polypeptide domains and fragments as described herein may vary in size by one or more amino acids, e.g., one, two, three, four, five, six, or more amino acids, depending on, for example, the exact sequence of the polypeptide or the criteria used to define the particular domain or fragment. Such variation is well understood by those of ordinary skill in the art. Accordingly, in certain embodiments, a soluble, human TAJ polypeptide includes, for example, a polypeptide having a N-terminus between amino acids 20 and 32 of SEQ ID NO:2, extending to a C-terminus between amino acids 160 and 200 of SEQ ID NO:2. In one embodiment, a soluble, human TAJ polypeptide includes amino acids 26-173 of SEQ ID NO:2. A "soluble TAJ polypeptide" also encompasses fusions proteins, wherein a soluble fragment of TAJ is fused to a heterologous amino acid sequence such as a peptide tag, AP, or an Fc region of an immunoglobulin, e.g., of an IgG.

A human TAJ polypeptide is not limited to SEQ ID NO:2. A human TAJ polypeptide can comprise a sequence at least 90%, or at least 95%, 96%, 98%, or 99% identical to SEQ ID NO:2 or its extracellular domain. Also included is a TAJ polypeptide that comprises SEQ ID NO:2 or its extracellular domain with up to 15 amino acid deletions, substitutions, or additions. Such polypeptides can be readily assayed for TAJ biological activity, e.g., for the ability to affect neurite outgrowth or neuronal survival.

It is also clear to the skilled artisan that functional variants (i.e., having the same functions) of SEQ ID NO:2 can be constructed by, for example, making substitutions of residues or sequences (e.g., making conservative substitutions) or deleting terminal or internal residues or sequences not needed for biological activity. A great deal of guidance regarding what residues are critical or not critical for activity is provided in the knowledge of which residues of human TAJ are highly conserved compared with murine TAJ and other TNFR family members (see, e.g., Eby et al., 2000, *J. Biol. Chem.* 275: 15336-15342). A skilled artisan could, without undue experimentation, make conservative substitutions in SEQ ID NO:2 without affecting biological function. In another example, a skilled artisan could, without undue experimentation, make a non-conservative substitution in a critical residue (e.g., a highly conserved residue) to disrupt a TAJ function, e.g., to produce a dominant negative TAJ polypeptide, e.g., the transmembrane domain may be inactivated by substitutions of the normally hydrophobic amino acid residues which comprise a functional transmembrane domain with hydrophilic ones. In another example, cysteine residues can be deleted or replaced with other amino acids to prevent formation of unnecessary intramolecular disulfide bridges upon renaturation. Other approaches may involve amino acid modifications, for example, to enhance expression in a chosen expression system.

Treatment Methods Using Antagonists of TAJ

One embodiment of the present invention provides methods for treating a disease, disorder or injury associated with lack of neurite outgrowth, or neuronal cell death, e.g., multiple sclerosis in an animal suffering from such disease, the method comprising, consisting essentially of, or consisting of administering to the animal an effective amount of a TAJ antagonist selected from the group consisting of a soluble TAJ polypeptide, an anti-TAJ antibody and a TAJ antagonist polynucleotide. Such TAJ antagonists further include functional fragments, variants, or derivatives of any of the above antagonist molecules.

Additionally, the invention is directed to a method for promoting neurite outgrowth in a mammal comprising, consisting essentially of, or consisting of administering a therapeutically effective amount of a TAJ antagonist selected from the group consisting of a soluble TAJ polypeptide, an anti-TAJ antibody and a TAJ antagonist polynucleotide. Such TAJ antagonists further include functional fragments, variants, or derivatives of any of the above antagonist molecules.

Also included in the present invention is a method of promoting neurite outgrowth, comprising, consisting essentially of, or consisting of contacting a neuron with an effective amount of a TAJ antagonist as described above. In addition, the invention provides a method of promoting neuronal survival, comprising, consisting essentially of, or consisting of contacting a neuron with an effective amount of a TAJ antagonist as described above.

A TAJ antagonist, e.g., a soluble TAJ polypeptide, an anti-TAJ antibody and a TAJ antagonist polynucleotide or fragments, variants, or derivatives of such molecules to be used in treatment methods disclosed herein, can be prepared and used as a therapeutic agent that stops, reduces, prevents, or inhibits the ability of TAJ to negatively regulate neuronal growth or regeneration.

In methods of the present invention, a TAJ antagonist can be administered via direct administration of a soluble TAJ polypeptide, an anti-TAJ antibody and a TAJ antagonist polynucleotide to the patient. Alternatively, the TAJ antagonist can be administered via an expression vector which expresses the specific TAJ antagonist, either in vivo or ex vivo.

Diseases or disorders which may be treated or ameliorated by the methods of the present invention include diseases, disorders or injuries which relate to the death or lack of axonal regeneration. Such disease include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), globoid cell leukodystrophy (Krabbe's disease) and Wallerian Degeneration.

Diseases or disorders which may be treated or ameliorated by the methods of the present invention include neurodegenerate disease or disorders. Such diseases include, but are not limited to, amyotrophic lateral sclerosis, Huntington's disease, Alzheimer's disease, diabetic neuropathy, and Parkinson's disease.

Examples of additional diseases, disorders or injuries which may be treated or ameliorated by the methods of the present invention include, but are not limited to spinal cord injuries, chronic myelopathy or rediculopathy, tramatic brain injury, motor neuron disease, axonal shearing, contusions, paralysis, post radiation damage or other neurological complications of chemotherapy, stroke, large lacunes, medium to large vessel occlusions, leukoariaosis, acute ischemic optic neuropathy, vitamin E deficiency (isolated deficiency syndrome, AR, Bassen-Kornzweig syndrome), B12, B6 (pyridoxine-pellagra), thiamine, folate, nicotinic acid deficiency, Marchiafava-Bignami syndrome, Metachromatic Leukodystrophy, Trigeminal neuralgia, Bell's palsy, or any neural injury which would require axonal regeneration, remylination or oligodendrocyte survival or differentiation/proliferation.

TAJ Antagonists

A TAJ antagonist is an agent which blocks or inhibits TAJ signaling pathway, thereby inhibiting the ability of TAJ to negatively regulate neuronal growth. As a result, a TAJ antagonist increases, induces, or promotes neuronal survival and/or neurite outgrowth. TAJ antagonists for use in the methods disclosed herein include, but are not limited to a soluble TAJ polypeptide or fragment, variant, or derivative thereof; an anti-TAJ antibody or an antigen-binding fragment, variant, or derivative thereof; and a TAJ antagonist polynucleotide, e.g., an antisense or RNAi polynucleotide. TAJ antagonists further include polynucleotides which encode any of the TAJ antagonists listed above. A TAJ antagonist can be administered alone or in combination with another TAJ antagonist listed herein, or with any other treatment which modulates MAIF-induced neurite outgrowth, e.g., a LINGO-1 antagonist and/or a Nogo receptor antagonist. LINGO-1 antagonists and Nogo receptor antagonists are described in, e.g., PCT Publication Nos. WO 2004/085648, WO 2005/016955, WO 03/031462, WO 2004/014311, and WO 01/51520, all of which are incorporated herein by reference in their entireties.

Soluble TAJ Polypeptides

A soluble TAJ polypeptide, or fragment, variant or derivative thereof, acting as an antagonist, can block, inhibit or interfere with the biological function of a naturally occurring TAJ polypeptide.

Soluble TAJ polypeptides or fragments, variants, or derivatives thereof lack the transmembrane domain of the TAJ polypeptide and optionally lack the cytoplasmic domain. Certain soluble TAJ polypeptides are composed one or more TAJ CRDs, e.g., amino acid fragments of about amino acid 33 to about amino acid 73 of SEQ ID NO:2, about amino acid 33 to about amino acid 115 of SEQ ID NO:2, about amino acid 33 to about amino acid 160 of SEQ ID NO:2, about amino acid 33 to about amino acid 173 of SEQ ID NO:2, about amino acid 74 to about amino acid 115 of SEQ ID NO:2, about amino acid 74 to about amino acid 160 of SEQ ID NO:2, about amino acid 74 to about amino acid 173 of SEQ ID NO:2, about amino acid 116 to about amino acid 160 of SEQ ID NO:2, about amino acid 116 to about amino acid 173 of SEQ ID NO:2, about amino acid 26 to about amino acid 73 of SEQ ID NO:2, about amino acid 26 to about amino acid 115 of SEQ ID NO:2, about amino acid 26 to about amino acid 160 of SEQ ID NO:2, and/or the entire extracellular domain (corresponding to about amino acids 26 to about 173 of SEQ ID NO:2). The CRDs or the entire extracellular domain of the TAJ polypeptide, as described above, may include additional or fewer amino acids on either the C-terminal or N-terminal end of the fragment, as denoted by use of term "about." Furthermore, soluble TAJ polypeptides as described herein may have various alterations such as substitutions, insertions or deletions.

A soluble TAJ polypeptide can comprise a fragment of at least six, e.g., ten, fifteen, twenty, twenty-five, thirty, forty, fifty, sixty, seventy, one hundred, or more amino acids of SEQ ID NO: 2. In addition, a soluble TAJ polypeptide may comprise at least one, e.g., five, ten, fifteen or twenty conservative amino acid substitutions. Corresponding fragments of soluble TAJ polypeptides at least 70%, 75%, 80%, 85%, 90%, or 95% identical to a reference TAJ polypeptide of SEQ ID NO:2 described herein are also contemplated.

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

Soluble TAJ polypeptides for use in the methods of the present invention may include any combination of two or more soluble TAJ polypeptides. Accordingly, soluble TAJ polypeptide dimers, either homodimers or heterodimers, are contemplated. Two or more soluble TAJ polypeptides as described herein may be directly connected, or may be connected via a suitable peptide linker. Such peptide linkers are described elsewhere herein.

Accordingly, methods described herein that use TAJ polypeptides, and in particular human TAJ, are not limited to the use of SEQ ID NO:2. Also included are TAJ polypeptides that include a sequence at least 90%, preferably at least 95%, 96%, 98%, or 99% identical to SEQ ID NO:2 or its extracellular domain. Also included are TAJ polypeptides that comprise SEQ ID NO:2 or its extracellular domain with up to 15 amino acid deletions, substitutions, or additions. Such polypeptides can be readily assayed for biological activity, e.g., for the ability to affect neurite outgrowth.

Soluble TAJ polypeptides for use in the methods of the present invention described herein may be cyclic. Cyclization of the soluble TAJ polypeptides reduces the conformational freedom of linear peptides and results in a more structurally constrained molecule. Many methods of peptide cyclization are known in the art. For example, "backbone to backbone" cyclization by the formation of an amide bond between the N-terminal and the C-terminal amino acid residues of the peptide. The "backbone to backbone" cyclization method includes the formation of disulfide bridges between two ω-thio amino acid residues (e.g. cysteine, homocysteine). Certain soluble TAJ peptides of the present invention include modifications on the N- and C-terminus of the peptide to form a cyclic TAJ polypeptide. Such modifications include, but are not limited to, cysteine residues, acetylated cysteine residues cysteine residues with a $NH_2$ moiety and biotin. Other methods of peptide cyclization are described in Li & Roller. *Curr. Top. Med. Chem.* 3:325-341 (2002), which is incorporated by reference herein in its entirety.

Fusion Proteins and Conjugates

Some embodiments of the invention involve the use of a TAJ polypeptide, wherein a TAJ polypeptide moiety is fused to a heterologous polypeptide moiety at the N- or C-terminus to form a fusion protein. Such fusion proteins can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the heterologous moiety can be inert or biologically active. Also, it can be chosen to be stably fused to the TAJ moiety or to be cleavable, in vitro or in vivo. Heterologous moieties to accomplish different objectives are known in the art.

Fc Fusion Proteins

In one embodiment, a soluble TAJ polypeptide is fused to a hinge and Fc region, i.e., the C-terminal portion of an Ig heavy chain constant region. Potential advantages of a TAJ-Fc fusion include solubility, in vivo stability, and multivalency, e.g., dimerization. The Fc region used can be an IgA, IgD, or IgG Fc region (hinge-$C_H2$-$C_H3$). Alternatively, it can be an IgE or IgM Fc region (hinge-$C_H2$-$C_H3$-$C_H4$). An IgG Fc region is generally used, e.g., an IgG1 Fc region or IgG4 Fc region. In one embodiment, a sequence beginning in the hinge region just upstream of the papain cleavage site which defines IgG Fc chemically (i.e. residue 216, taking the first residue of heavy chain constant region to be 114 according to the Kabat system), or analogous sites of other immunoglobulins is used in the fusion. The precise site at which the fusion is made is not critical; particular sites are well known and may be selected in order to optimize the biological activity, secretion, or binding characteristics of the molecule. Materials and methods for constructing and expressing DNA encoding Fc fusions are known in the art and can be applied to obtain soluble TAJ fusions without undue experimentation. Some embodiments of the invention employ a TAJ fusion protein such as those described in Capon et al., U.S. Pat. Nos. 5,428, 130 and 5,565,335.

The TAJ portion of the fusion protein preferably includes at least a portion of the extracellular region of TAJ and preferably lacks a transmembrane domain, such that the TAJ moiety is soluble. The N-terminus of the TAJ portion of a soluble fusion protein is typically a residue between about amino acid 20 to 50 of SEQ ID NO:2 and the C-terminus is typically a residue between about amino acid 130 to 185 of SEQ ID NO:2. Thus, examples of a TAJ portion of a soluble Fc fusion protein includes amino acid 20 to amino acid 173 SEQ ID NO:2, amino acids 26 to 180 of SEQ ID NO:2, and amino acids 40 to 185 of SEQ ID NO:2.

The signal sequence is a polynucleotide that encodes an amino acid sequence that initiates transport of a protein across the membrane of the endoplasmic reticulum. Signal sequences useful for constructing a fusion protein include antibody light chain signal sequences, e.g., antibody 14.18 (Gillies et al., 1989, *J. Immunol. Meth.*, 125:191-202), antibody heavy chain signal sequences, e.g., the MOPC141 antibody heavy chain signal sequence (Sakano et al., 1980, *Nature* 286:5774). Alternatively, other signal sequences can be used. See, for example, Watson, 1984, *Nucleic Acids Research* 12:5145). The signal peptide is usually cleaved in the lumen of the endoplasmic reticulum by signal peptidases. This results in the secretion of a fusion protein containing the Fc region and the TAJ moiety.

In some embodiments the DNA sequence encodes a proteolytic cleavage site between the secretion cassette and the TAJ moiety. A cleavage site provides for the proteolytic cleavage of the encoded fusion protein, thus separating the Fc domain from the target protein. Useful proteolytic cleavage sites include amino acids sequences recognized by proteolytic enzymes such as trypsin, plasmin, thrombin, factor Xa, or enterokinase K.

The secretion cassette can be incorporated into a replicable expression vector. Useful vectors include linear nucleic acids, plasmids, phagemids, cosmids and the like. An exemplary expression vector is pdC, in which the transcription of the immunofusin DNA is placed under the control of the enhancer and promoter of the human cytomegalovirus. See, e.g., Lo et al., 1991, *Biochim. Biophys. Acta* 1088:712; and Lo et al., 1998, *Protein Engineering* 11:495-500. An appropriate host cell can be transformed or transfected with a DNA that encodes a TAJ polypeptide, and is used for the expression and secretion of the TAJ polypeptide. Preferred host cells include immortal hybridoma cells, myeloma cells, 293 cells, Chinese hamster ovary (CHO) cells, Hela cells, and COS cells.

Certain sites preferably can be deleted from the Fc region during the construction of the secretion cassette. For example, since coexpression with the light chain is unnecessary, the binding site for the heavy chain binding protein, Bip (Hendershot et al., 1987, *Immunol. Today* 8:111-114), can be deleted from the CH2 domain of the Fc region of IgE, such that this site does not interfere with the efficient secretion of the immunofusin. Transmembrane domain sequences, such as those present in IgM, can be deleted.

The IgG1 Fc region is preferred. Alternatively, the Fc region of the other subclasses of immunoglobulin gamma (gamma-2, gamma-3 and gamma-4) can be used in the secretion cassette. The IgG1 Fc region of immunoglobulin gamma-1 is preferably used in the secretion cassette includes the hinge region (at least part), the $C_H2$ region, and all or part of the $C_H3$ region. In some embodiments, the Fc region of immunoglobulin gamma-1 is a $C_H2$-deleted-Fc, which includes part of the hinge region and the $C_H3$ region, but not the $C_H2$ region. A $C_H2$-deleted-Fc has been described by Gillies et al., 1990, *Hum. Antibod. Hybridomas*, 1:47. In some embodiments, the Fc regions of IgA, IgD, IgE, or IgM, are used.

TAJ fusion proteins can be constructed in several different configurations. In one configuration the C-terminus of the TAJ moiety is fused directly to the N-terminus of the Fc moiety. In a slightly different configuration, a short polypeptide, e.g., 2-10 amino acids, is incorporated into the fusion between the N-terminus of the TAJ moiety and the C-terminus of the Fc moiety. Such a linker can provide conformational flexibility, which may improve biological activity in some circumstances. If a sufficient portion of the hinge region is retained in the Fc moiety, the TAJ-Fc fusion will dimerize, thus forming a divalent molecule. A homogeneous population of monomeric Fc fusions will yield monospecific, bivalent dimers. A mixture of two monomeric Fc fusions each having a different specificity will yield bispecific, bivalent dimers.

Other Fusion Proteins

TAJ polypeptides can also be fused to heterologous peptides to facilitate purification or identification of the TAJ moiety. For example, a histidine tag can be fused to a TAJ polypeptide to facilitate purification using commercially available chromatography media.

In some embodiments of the invention, a TAJ fusion construct is used to enhance the production of a TAJ moiety in bacteria. In such constructs a bacterial protein normally expressed and/or secreted at a high level is employed as the N-terminal fusion partner of a TAJ polypeptide. See, e.g., Smith et al., 1988 *Gene* 67:31; Hopp et al., 1988, *Biotechnology* 6:1204; La Vallie et al., 1993, *Biotechnology* 11:187.

By fusing a TAJ moiety at the amino and carboxy termini of a suitable fusion partner, bivalent or tetravalent forms of a TAJ polypeptide can be obtained. For example, a TAJ moiety can be fused to the amino and carboxy termini of an Ig moiety to produce a bivalent monomeric polypeptide containing two TAJ moieties. Upon dimerization of two of these monomers, by virtue of the Ig moiety, a tetravalent form of a TAJ protein is obtained. Such multivalent forms can be used to achieve increased binding affinity for the target. Multivalent forms of TAJ also can be obtained by placing TAJ moieties in tandem to form concatamers, which can be employed alone or fused to a fusion partner such as Ig or HSA.

Conjugated Polymers

Any of a number of cross-linkers that contain a corresponding amino reactive group and thiol reactive group can be used to link TAJ to a second protein, such as serum albumin. Examples of suitable linkers include amine reactive cross linkers that insert a thiol reactive-maleimide, e.g., SMCC, AMAS, BMPS, MBS, EMCS, SMPB, SMPH, KMUS, and GMBS. Other suitable linkers insert a thiol reactive-haloacetate group, e.g., SBAP, SIA, SLAB. Linkers that provide a protected or non-protected thiol for reaction with sulfhydryl groups to product a reducible linkage include SPDP, SMPT, SATA, and SATP. Such reagents are commercially available (e.g., Pierce Chemicals).

Conjugation does not have to involve the N-terminus of a TAJ polypeptide or the thiol moiety on serum albumin. For example, TAJ-albumin fusions can be obtained using genetic engineering techniques, wherein the TAJ moiety is fused to the serum albumin gene at its N-terminus, C-terminus, or both.

As an alternative to expression of a TAJ fusion protein, a chosen heterologous moiety can be preformed and chemically conjugated to the TAJ moiety. In most cases, a chosen heterologous moiety will function similarly, whether fused or conjugated to the TAJ moiety. Therefore, in the following discussion of heterologous amino acid sequences, unless otherwise noted, it is to be understood that the heterologous sequence can be joined to the TAJ moiety in the form of a fusion protein or as a chemical conjugate.

Pharmacologically active polypeptides such as TAJ often exhibit rapid in vivo clearance, necessitating large doses to achieve therapeutically effective concentrations in the body. In addition, polypeptides smaller than about 60 kDa potentially undergo glomerular filtration, which sometimes leads to nephrotoxicity. Fusion or conjugation of relatively small polypeptides such as TAJ fragments can be employed to reduce or avoid the risk of such nephrotoxicity. Various heterologous amino acid sequences, i.e., polypeptide moieties or "carriers," for increasing the in vivo stability, i.e., serum half-life, of therapeutic polypeptides are known.

Due to its long half-life, wide in vivo distribution, and lack of enzymatic or immunological function, essentially full-length human serum albumin (HSA), or an HSA fragment, is a preferred heterologous moiety. Through application of methods and materials such as those taught in Yeh et al., 1992, *Proc. Natl. Acad. Sci. USA*, 89:1904-1908 and Syed et al., 1997, *Blood* 89:3243-3252, HSA can be used to form a TAJ fusion protein or conjugate that displays pharmacological activity by virtue of the TAJ moiety while displaying significantly increased, e.g., 10-fold to 100-fold higher, in vivo stability. Preferably, the C-terminus of the HSA is fused to the N-terminus of the TAJ moiety. Since HSA is a naturally secreted protein, the HSA signal sequence can be exploited to obtain secretion of the TAJ fusion protein into the cell culture medium, when the fusion protein is produced in a eukaryotic, e.g., mammalian, expression system.

Some embodiments of the invention involve a TAJ polypeptide wherein one or more polymers are conjugated (covalently linked) to the TAJ polypeptide. Examples of polymers suitable for such conjugation include polypeptides (discussed above), sugar polymers and polyalkylene glycol chains. Typically, but not necessarily, a polymer is conjugated to the TAJ polypeptide for the purpose of improving one or more of the following: solubility, stability, or bioavailability. For example, TAJ antagonist polypeptides or antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

A preferred class of polymer for conjugation to a TAJ polypeptide is a polyalkylene glycol. Polyethylene glycol (PEG) is particularly preferred. PEG moieties, e.g., 1, 2, 3, 4 or 5 PEG polymers, can be conjugated to each TAJ polypeptide to increase serum half life, as compared to the TAJ polypeptide alone. PEG moieties are non-antigenic and essentially biologically inert. PEG moieties used in the practice of the invention may be branched or unbranched.

The number of PEG moieties attached to the TAJ polypeptide and the molecular weight of the individual PEG chains can vary. In general, the higher the molecular weight of the polymer, the fewer polymer chains attached to the polypeptide. A PEG moiety can be linked to the TAJ polypeptide through any suitable, exposed reactive group on the polypeptide. The exposed reactive group(s) can be, for example, an N-terminal amino group or the epsilon amino group of an internal lysine residue, or both. An activated polymer can react and covalently link at any free amino group on the TAJ polypeptide. Free carboxylic groups, suitably activated carbonyl groups, hydroxyl, guanidyl, imidazole, oxidized carbohydrate moieties and mercapto groups of the TAJ (if available) also can be used as reactive groups for polymer attachment.

Preferably, in a conjugation reaction, from about 1.0 to about 10 moles of activated polymer per mole of polypeptide, depending on polypeptide concentration, is employed. Usually, the ratio chosen represents a balance between maximizing the reaction while minimizing side reactions (often non-specific) that can impair the desired pharmacological activity of the TAJ moiety. Preferably, at least 50% of the biological activity (as demonstrated, e.g., in any of the assays described herein or known in the art) of the TAJ polypeptide is retained, and most preferably nearly 100% is retained.

The polymer can be conjugated to the TAJ polypeptide using conventional chemistry. For example, a polyalkylene glycol moiety can be coupled to a lysine epsilon amino group of the TAJ polypeptide. Linkage to the lysine side chain can be performed with an N-hydroxylsuccinimide (NHS) active ester such as PEG succinimidyl succinate (SS-PEG) and succinimidyl propionate (SPA-PEG). Suitable polyalkylene glycol moieties include, e.g. carboxymethyl-NHS, norleucine-NHS, SC-PEG, tresylate, aldehyde, epoxide, carbonylimidazole, and PNP carbonate. These reagents are commercially available. Additional amine reactive PEG linkers can be substituted for the succinimidyl moiety. These include, e.g., isothiocyanates, nitrophenylcarbonates, epoxides, and benzotriazole carbonates. Conditions preferably are chosen to maximize the selectivity and extent or reaction. Such optimization of reaction conditions is within ordinary skill in the art.

PEGylation can be carried out by any of the PEGylation reactions known in the art. See, e.g., Focus on Growth Factors, 3: 4-10, 1992; published European patent applications EP 0 154 316 and EP 0 401 384. PEGylation may be carried out using an acylation reaction or an alkylation reaction with a reactive polyethylene glycol molecule (or an analogous reactive water-soluble polymer).

PEGylation by acylation generally involves reacting an active ester derivative of polyethylene glycol. Any reactive PEG molecule can be employed in the PEGylation. A preferred activated PEG ester is PEG esterified to N-hydroxysuccinimide (NHS). As used herein, "acylation" includes without limitation the following types of linkages between the therapeutic protein and a water soluble polymer such as PEG: amide, carbamate, urethane, and the like. See, Bioconjugate Chem. 5: 133-140, 1994. Reaction parameters should be chosen to avoid temperature, solvent, and pH conditions that would damage or inactivate the TAJ polypeptide.

Preferably, the connecting linkage is an amide. Preferably, at least 95% of the resulting product is mono, di- or tri-PEGylated. However, some species with higher degrees of PEGylation may be formed in amounts depending on the specific reaction conditions used. Optionally, purified PEGylated species are separated from the mixture, particularly unreacted species, by conventional purification methods, including, e.g., dialysis, salting-out, ultrafiltration, ion-exchange chromatography, gel filtration chromatography, and electrophoresis.

PEGylation by alkylation generally involves reacting a terminal aldehyde derivative of PEG with TAJ in the presence of a reducing agent. In addition, one can manipulate the reaction conditions to favor PEGylation substantially only at the N-terminal amino group of TAJ (i.e., a mono-PEGylated protein). In either case of mono-PEGylation or poly-PEGylation, the PEG groups are preferably attached to the protein via a $—C_H2-NH—$ group. With particular reference to the $—C_H2$-group, this type of linkage is known as an "alkyl" linkage.

Derivatization via reductive alkylation to produce a mono-PEGylated product exploits differential reactivity of different types of primary amino groups (lysine versus the N-terminal) available for derivatization. The reaction is performed at a pH that allows one to take advantage of the pKa differences between the epsilon-amino groups of the lysine residues and that of the N-terminal amino group of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs.

The polymer molecules used in both the acylation and alkylation approaches are selected from among water soluble polymers. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono C1-C10 alkoxy or aryloxy derivatives thereof (see, U.S. Pat. No. 5,252,714). The polymer may be branched or unbranched. For the acylation reactions, the polymer(s) selected should have a single reactive ester group. For reductive alkylation, the polymer(s) selected should have a single reactive aldehyde group. Generally, the water soluble polymer will not be selected from naturally-occurring glycosyl residues since these are usually made more conveniently by mammalian recombinant expression systems.

Methods for preparing a PEGylated TAJ generally includes the steps of (a) reacting a TAJ protein or polypeptide with polyethylene glycol (such as a reactive ester or aldehyde derivative of PEG) under conditions whereby the molecule becomes attached to one or more PEG groups, and (b) obtaining the reaction product(s). In general, the optimal reaction conditions for the acylation reactions will be determined case by case based on known parameters and the desired result. For example, the larger the ratio of PEG:protein, the greater the percentage of poly-PEGylated product.

Reductive alkylation to produce a substantially homogeneous population of mono-polymer/TAJ generally includes the steps of: (a) reacting a TAJ protein or polypeptide with a reactive PEG molecule under reductive alkylation conditions, at a pH suitable to permit selective modification of the N-terminal amino group of TAJ; and (b) obtaining the reaction product(s).

For a substantially homogeneous population of mono-polymer/TAJ, the reductive alkylation reaction conditions are those that permit the selective attachment of the water soluble polymer moiety to the N-terminus of TAJ. Such reaction conditions generally provide for pKa differences between the lysine side chain amino groups and the N-terminal amino group. For purposes of the present invention, the preferred pH is in the range of 3-9, preferably 3-6.

TAJ polypeptides can include a tag, e.g., a moiety that can be subsequently released by proteolysis. Thus, the lysine moiety can be selectively modified by first reacting a His-tag modified with a low molecular weight linker such as Traut's reagent (Pierce) which will react with both the lysine and N-terminus, and then releasing the his tag. The polypeptide will then contain a free SH group that can be selectively modified with a PEG containing a thiol reactive head group such as a maleimide group, a vinylsulfone group, a haloacetate group, or a free or protected SH.

Traut's reagent can be replaced with any linker that will set up a specific site for PEG attachment. For example, Traut's reagent can be replaced with SPDP, SMPT, SATA, or SATP (Pierce). Similarly one could react the protein with an amine reactive linker that inserts a maleimide (for example SMCC, AMAS, BMPS, MBS, EMCS, SMPB, SMPH, KMUS, or GMBS), a haloacetate group (SBAP, SIA, SIAB), or a vinylsulfone group and react the resulting product with a PEG that contains a free SH.

In some embodiments, the polyalkylene glycol moiety is coupled to a cysteine group of the TAJ polypeptide. Coupling can be effected using, e.g., a maleimide group, a vinylsulfone group, a halo acetate group, or a thiol group.

Optionally, the TAJ polypeptide is conjugated to the polyethylene glycol moiety through a labile bond. The labile bond can be cleaved in, e.g., biochemical hydrolysis, proteolysis, or sulfhydryl cleavage. For example, the bond can be cleaved under in vivo (physiological) conditions.

The reactions may take place by any suitable method used for reacting biologically active materials with inert polymers, preferably at about pH 5-8, e.g., pH 5, 6, 7, or 8, if the reactive groups are on the alpha amino group at the N-terminus. Generally the process involves preparing an activated polymer and thereafter reacting the protein with the activated polymer to produce the soluble protein suitable for formulation.

Antibodies or Immunospecific Fragments Thereof

TAJ antagonists for use in the methods of the present invention also include TAJ-specific antibodies or antigen-binding fragments, variants, or derivatives which are antagonists of TAJ activity. For example, binding of certain TAJ antibodies to TAJ, as expressed on adult nervous system, block the inhibition of neuronal growth, thereby promoting neuronal survival, neurite outgrowth, and/or axon regeneration.

Certain antagonist antibodies for use in the methods described herein specifically or preferentially binds to a particular TAJ polypeptide fragment or domain. Such TAJ polypeptide fragments include, but are not limited to, a TAJ polypeptide comprising, consisting essentially of, or consisting of amino acid fragments of about amino acid 33 to about amino acid 73 of SEQ ID NO:2, about amino acid 33 to about amino acid 115 of SEQ ID NO:2, about amino acid 33 to about amino acid 160 of SEQ ID NO:2, about amino acid 33 to about amino acid 173 of SEQ ID NO:2, about amino acid 74 to about amino acid 115 of SEQ ID NO:2, about amino acid 74 to about amino acid 160 of SEQ ID NO:2, about amino acid 74 to about amino acid 173 of SEQ ID NO:2, about amino acid 116 to about amino acid 160 of SEQ ID NO:2, about amino acid 116 to about amino acid 173 of SEQ ID NO:2, about amino acid 26 to about amino acid 73 of SEQ ID NO:2, about amino acid 26 to about amino acid 115 of SEQ ID NO:2, about amino acid 26 to about amino acid 160 of SEQ ID NO:2, and/or the entire extracellular domain (corresponding to about amino acids 26 to about 173 of SEQ ID NO:2), or a TAJ variant polypeptide at least 70%, 75%, 80%, 85%, 90%, or 95% identical to amino acid fragments of about amino acid 33 to about amino acid 73 of SEQ ID NO:2, about amino acid 33 to about amino acid 115 of SEQ ID NO:2, about amino acid 33 to about amino acid 160 of SEQ ID NO:2, about amino acid 33 to about amino acid 173 of SEQ ID NO:2, about amino acid 74 to about amino acid 115 of SEQ ID NO:2, about amino acid 74 to about amino acid 160 of SEQ ID NO:2, about amino acid 74 to about amino acid 173 of SEQ ID NO:2, about amino acid 116 to about amino acid 160 of SEQ ID NO:2, about amino acid 116 to about amino acid 173 of SEQ ID NO:2, about amino acid 26 to about amino acid 73 of SEQ ID NO:2, about amino acid 26 to about amino acid 115 of SEQ ID NO:2, about amino acid 26 to about amino acid 160 of SEQ ID NO:2, and/or the entire extracellular domain (corresponding to about amino acids 26 to about 173 of SEQ ID NO:2).

In other embodiments, the present invention includes an antibody, or antigen-binding fragment, variant, or derivative thereof which specifically or preferentially binds to at least one epitope of TAJ, where the epitope comprises, consists essentially of, or consists of at least about four to five amino acids of SEQ ID NO:2, at least seven, at least nine, or between at least about 15 to about 30 amino acids of SEQ ID NO:2.

The amino acids of a given epitope of SEQ ID NO:2 as described may be, but need not be contiguous or linear. In certain embodiments, the at least one epitope of TAJ comprises, consists essentially of, or consists of a non-linear epitope formed by the extracellular domain of TAJ as expressed on the surface of a cell or as a soluble fragment, e.g., fused to an IgG Fc region. Thus, in certain embodiments the at least one epitope of TAJ comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:2, where non-contiguous amino acids form an epitope through protein folding.

In other embodiments, the present invention includes an antibody, or antigen-binding fragment, variant, or derivative thereof which specifically or preferentially binds to at least one epitope of TAJ, where the epitope comprises, consists essentially of, or consists of, in addition to one, two, three, four, five, six or more contiguous or non-contiguous amino acids of SEQ ID NO:2 as described above, and an additional moiety which modifies the protein, e.g., a carbohydrate moiety may be included such that the TAJ antibody binds with higher affinity to modified target protein than it does to an unmodified version of the protein. Alternatively, the TAJ antibody does not bind the unmodified version of the target protein at all.

In certain embodiments, an antibody, or antigen-binding fragment, variant, or derivative thereof of the invention binds specifically to at least one epitope of TAJ or fragment or variant described above, i.e., binds to such an epitope more readily than it would bind to an unrelated, or random epitope; binds preferentially to at least one epitope of TAJ or fragment, variant, or derivative described above, i.e., binds to such an epitope more readily than it would bind to a related, similar, homologous, or analogous epitope; competitively inhibits binding of a reference antibody which itself binds specifically or preferentially to a certain epitope of TAJ or fragment or variant described above; or binds to at least one epitope of TAJ or fragment or variant described above with an affinity characterized by a dissociation constant $K_D$ of less than about $5\times10^{-2}$ M, about $10^{-2}$ M, about $5\times10^{-3}$ M, about $10^{-3}$ M, about $5\times10^{-4}$ M, about $10^{-4}$ M, about $5\times10^{-5}$ M, about $10^{-5}$ M, about $5\times10^{-6}$ M, about $10^{-6}$ M, about $5\times10^{-7}$ M, about $10^{-7}$ M, about $5\times10^{-8}$ M, about $10^{-8}$ M, about $5\times10^{-9}$ M, about $10^{-9}$ M, about $5\times10^{-10}$ M, about $10^{-10}$ M, about $5\times10^{-11}$ M, about $10^{-11}$ M, about $5\times10^{-12}$ M, about $10^{-12}$ M, about $5\times10^{-13}$ M, about $10^{-13}$ M, about $5\times10^{-14}$ M, about $10^{-14}$ M, about $5\times10^{-15}$ M, or about $10^{-15}$ M. In a particular aspect, the antibody or fragment thereof preferentially binds to a human TAJ polypeptide or fragment thereof, relative to a murine TAJ polypeptide or fragment thereof.

As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M.

In specific embodiments, an antibody, or antigen-binding fragment, variant, or derivative thereof of the invention binds TAJ polypeptides or fragments or variants thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. Alternatively, an antibody, or antigen-binding fragment, variant, or derivative thereof of the invention binds TAJ polypeptides or fragments or variants thereof with an off rate (k(off)) of less than or equal to $5\times10^{-4}$ sec$^{-1}$, $10^{-4}$ sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{-7}$ sec$^{-1}$ or $10^{-7}$ sec$^{-1}$.

In other embodiments, an antibody, or antigen-binding fragment, variant, or derivative thereof of the invention binds TAJ polypeptides or fragments or variants thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. Alternatively, an antibody, or antigen-binding fragment, variant, or derivative thereof of the invention binds TAJ polypeptides or fragments or variants thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

In one embodiment, a TAJ antagonist for use in the methods of the invention is an antibody molecule, or immunospecific fragment thereof. Unless it is specifically noted, as used herein a "fragment thereof" in reference to an antibody refers to an immunospecific fragment, i.e., an antigen-specific fragment. In one embodiment, an antibody of the invention is a bispecific binding molecule, binding polypeptide, or antibody, e.g., a bispecific antibody, minibody, domain deleted antibody, or fusion protein having binding specificity for more than one epitope, e.g., more than one antigen or more than one epitope on the same antigen. In one embodiment, a bispecific antibody has at least one binding domain specific for at least one epitope on TAJ. A bispecific antibody may be a tetravalent antibody that has two target binding domains specific for an epitope of TAJ and two target binding domains specific for a second target. Thus, a tetravalent bispecific antibody may be bivalent for each specificity.

In certain embodiments of the present invention comprise administration of a TAJ antagonist antibody, or immunospecific fragment thereof, in which at least a fraction of one or more of the constant region domains has been deleted or otherwise altered so as to provide desired biochemical characteristics such as reduced effector functions, the ability to non-covalently dimerize, increased ability to localize at the site of a neuron, reduced serum half-life, or increased serum half-life when compared with a whole, unaltered antibody of approximately the same immunogenicity. For example, certain antibodies for use in the treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the $C_H2$ domain will be deleted.

In certain TAJ antagonist antibodies or immunospecific fragments thereof for use in the therapeutic methods described herein, the Fc portion may be mutated to decrease effector function using techniques known in the art. For example, the deletion or inactivation (through point mutations or other means) of a constant region domain may reduce Fc receptor binding of the circulating modified antibody thereby increasing CNS localization, especially in neurons. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as CNS localization, biodistribution and serum half-life, may easily be measured and quantified using well know immunological techniques without undue experimentation.

Modified forms of antibodies or immunospecific fragments thereof for use in the diagnostic and therapeutic methods disclosed herein can be made from whole precursor or parent antibodies using techniques known in the art. Exemplary techniques are discussed in more detail herein.

In certain embodiments both the variable and constant regions of TAJ antagonist antibodies or immunospecific fragments thereof for use in the treatment methods disclosed herein are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human antibodies can likewise be produced by various display technologies, e.g., phage display or other viral display systems, as described in more detail elsewhere herein.

TAJ antagonist antibodies or immunospecific fragments thereof for use in the methods disclosed herein can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

In preferred embodiments, a TAJ antagonist antibody or immunospecific fragment thereof for use in the methods disclosed herein will not elicit a deleterious immune response in the animal to be treated, e.g., in a human. In one embodiment, TAJ antagonist antibodies or immunospecific fragments thereof for use in the treatment methods disclosed herein be modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, $V_H$ and $V_L$ sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., TAJ antagonist antibodies or immunospecific fragments thereof for use in the methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

TAJ antagonist antibodies or fragments thereof for use in the methods of the present invention may be generated by any suitable method known in the art. Polyclonal antibodies can be produced by various procedures well known in the art. For example, a TAJ immunospecific fragment can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, Cold Spring Harbor Laboratory Press, 2nd ed. (1988); Hammerling et al., in: *Monoclonal Antibodies and T-Cell Hybridomas* Elsevier, N.Y., 563-681 (1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art including the use of hybridoma and recombinant and phage display technology.

Using art recognized protocols, in one example, antibodies are raised in mammals by multiple subcutaneous or intraperitoneal injections of the relevant antigen (e.g., purified TAJ antigens or cells or cellular extracts comprising such antigens) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (MAbs). Preferably, the lymphocytes are obtained from the spleen.

In this well known process (Kohler et al., *Nature* 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by in vitro assays such as immunoprecipitation, radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, Academic Press, pp 59-103 (1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Antibody fragments that recognize specific epitopes may be generated by known techniques. For example, Fab and F(ab')2 fragments may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the $C_H1$ domain of the heavy chain.

Those skilled in the art will also appreciate that DNA encoding antibodies or antibody fragments (e.g., antigen binding sites) may also be derived from antibody phage libraries. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Exemplary methods are set forth, for example, in EP 368 684 B1; U.S. Pat. No. 5,969, 108, Hoogenboom, H. R. and Chames, *Immunol. Today* 21:371 (2000); Nagy et al. *Nat. Med.* 8:801 (2002); Huie et al., *Proc. Natl. Acad. Sci. USA* 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al., *Nat. Biotechnol.* 18:1287 (2000); Wilson et al., *Proc. Natl. Acad. Sci. USA* 98:3750 (2001); or Irving et al., *J. Immunol. Methods* 248:31 (2001)). In yet another embodiment, cell surface libraries can be screened for antibodies (Boder et al., *Proc. Natl. Acad. Sci. USA* 97:10701 (2000); Daugherty et al., *J. Immunol. Methods* 243:211 (2000)). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. In particular, DNA sequences encoding $V_H$ and $V_L$ regions are amplified from animal cDNA libraries (e.g., human or murine cDNA libraries of lymphoid tissues) or synthetic cDNA libraries. In certain embodiments, the DNA encoding the $V_H$ and $V_L$ regions are joined together by an scFv linker by PCR and cloned into a phagemid vector (e.g., pCANTAB 6 or pComb 3 HSS). The vector is electroporated in *E. coli* and the *E. coli* is infected with helper phage. Phage used in these methods are typically filamentous phage including fd and M13 and the $V_H$ or $V_L$ regions are usually recombinantly fused to either the phage gene III or gene VIII. Phage expressing an antigen binding domain that binds to an antigen of interest (i.e., a TAJ polypeptide or a fragment thereof) can be selected or identified with antigen, e.g., using labeled antigen or antigen bound or captured to a solid surface or bead.

Additional examples of phage display methods that can be used to make the antibodies include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403, 484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *Proc. Natl. Acad. Sci. USA* 90:7995-7999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816,397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(415):489-498 (1991); Studnicka et al., *Protein Engineering* 7(6):805-814 (1994); Roguska. et al., *Proc. Natl. Acad. Sci. USA* 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 12:899-903 (1988)). See also, U.S. Pat. No. 5,565,332.

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., TAJ. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci. USA* 81:851-855 (1984); Neuberger et al., *Nature* 312:604-608 (1984); Takeda et al., *Nature* 314:452-454 (1985)) by splicing genes from a mouse antibody molecule of appropriate antigen specificity together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be adapted to produce single chain antibodies. Single chain antibodies are formed by linking the heavy and light chain fragments of the Fv region via an amino acid bridge, resulting in a single chain antibody. Techniques for the assembly of functional Fv fragments in *E coli* may also be used (Skerra et al., *Science* 242:1038-1041 (1988)).

TAJ antagonist antibodies may also be human or substantially human antibodies generated in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibodies for use in the therapeutic methods disclosed herein can be produced by any method known in the art for the synthesis of antibodies, in particular, by chemical synthesis or preferably, by recombinant expression techniques as described herein.

It will further be appreciated that the scope of this invention further encompasses all alleles, variants and mutations of antigen binding DNA sequences.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Recombinant expression of an antibody, or fragment, derivative or analog thereof, e.g., a heavy or light chain of an antibody which is a TAJ antagonist, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., *EMBO J.* 2:1791 (1983)), in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 *Clinical Pharmacy* 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); *TIB TECH* 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (eds.), Current Protocols in Molecular Biology, John Wiley & Sons, NY (1993); Kriegler, *Gene Transfer and Expression*, A Laboratory Manual, Stockton Press, NY (1990); and in Chapters 12 and 13, Dracopoli et al. (eds), *Current Prolocols in Human Genetics*, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, *The use of vectors based on gene amplification for the expression of cloned genes in mammalian cells in DNA cloning*, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in U.S. 2002 0123057 A1.

In one embodiment, a binding molecule or antigen binding molecule for use in the methods of the invention comprises a synthetic constant region wherein one or more domains are partially or entirely deleted ("domain-deleted antibodies"). In certain embodiments compatible modified antibodies will comprise domain deleted constructs or variants wherein the entire $C_H2$ domain has been removed ($\Delta C_H2$ constructs). For other embodiments a short connecting peptide may be substituted for the deleted domain to provide flexibility and freedom of movement for the variable region. Those skilled in the art will appreciate that such constructs are particularly preferred due to the regulatory properties of the $C_H2$ domain on the catabolic rate of the antibody.

In certain embodiments, modified antibodies for use in the methods disclosed herein are minibodies. Minibodies can be made using methods described in the art (see, e.g., see e.g., U.S. Pat. No. 5,837,821 or WO 94/09817A1).

In another embodiment, modified antibodies for use in the methods disclosed herein are $C_H2$ domain deleted antibodies which are known in the art. Domain deleted constructs can be derived using a vector (e.g., from Biogen IDEC Incorporated) encoding an IgG1 human constant domain (see, e.g., WO 02/060955A2 and WO02/096948A2). This exemplary vector was engineered to delete the $C_H2$ domain and provide a synthetic vector expressing a domain deleted IgG1 constant region.

In one embodiment, a TAJ antagonist antibody or fragment thereof for use in the treatment methods disclosed herein comprises an immunoglobulin heavy chain having deletion or substitution of a few or even a single amino acid as long as it permits association between the monomeric subunits. For example, the mutation of a single amino acid in selected areas of the $C_H2$ domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The present invention also provides the use of antibodies that comprise, consist essentially of, or consist of, variants (including derivatives) of antibody molecules (e.g., the $V_H$ regions and/or $V_L$ regions) described herein, which antibodies or fragments thereof immunospecifically bind to a TAJ polypeptide. Standard techniques known to those of skill in the art can be used to introduce mutations in the nucleotide sequence encoding a binding molecule, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$CDR1, $V_H$CDR2, $V_H$CDR3, $V_L$ region, $V_L$CDR1, $V_L$CDR2, or $V_L$CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity.

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein can be determined using techniques described herein or by routinely modifying techniques known in the art.

Antibodies used in the methods described herein include polyclonal as well as monoclonal antibodies, including full length antibodies, and antibody homologues, such as multispecific antibodies (e.g., bispecific antibodies), chimeric, humanized and fully human antibodies, and fragments of any of the foregoing, including Fab, Fab', F(ab')2, and Fv fragments, diabodies, linear antibodies, single-chain antibody molecules, and multispecific antibodies formed from antibody fragments, so long as they exhibit the desired biological activity. A monoclonal antibody indicates the character of the antibody as being a substantially homogeneous population of antibodies, and is not to be construed as requiring production of the antibody by any particular method.

For example, monoclonal antibodies include those antibodies made by the hybridoma method first described by Kohler et al., Nature 256:495 (1975), or may be made by recombinant DNA methods (see, e.g., U.S. Pat. No. 4,816,567). Monoclonal antibodies may also be isolated from phage antibody libraries using, e.g., the techniques described in Clackson et al., Nature 352:624-628 (1991) and Marks et al., J. Mol. Biol. 222:581-597 (1991). Monoclonal antibodies also include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

Also included are humanized monoclonal antibodies. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may include residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will include at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444-6448 (1993).

The expression "linear antibodies" when used throughout this application refers to the antibodies described in Zapata et al. Protein Eng. 8(10):1057-1062 (1995). Briefly, these antibodies comprise a pair of tandem Fd segments ($V_H$-$C_{H1}$-$V_H$-$C_{H1}$) which form a pair of antigen binding regions. Linear antibodies can be bispecific or monospecific.

To express the antibodies or antibody fragments, DNAs encoding partial or full-length light and heavy chains are inserted into expression vectors such as plasmids, retroviruses, cosmids, YACs, EBV-derived episomes, and the like. The expression vector and expression control sequences are chosen to be compatible with the expression host cell used. The antibody light chain gene and the antibody heavy chain gene can be inserted into separate vector. In some embodiments, both genes are inserted into the same expression vector.

A convenient vector is one that encodes a functionally complete human $C_H$ or $C_L$ immunoglobulin sequence. Preferably, restriction sites engineered so that any $V_H$ or $V_L$ sequence can be easily inserted and expressed. In such vectors, splicing usually occurs between the splice donor site in the inserted J region and the splice acceptor site preceding the human C region, and also at the splice regions that occur within the human $C_H$ exons. Polyadenylation and transcription termination occur at native chromosomal sites downstream of the coding regions. The recombinant expression vector can also encode a signal peptide that facilitates secretion of the antibody chain from a host cell.

In some embodiments, a TAJ antibody (or antigen-binding antibody fragment) can be administered directly as a preformed polypeptide, or indirectly through a nucleic acid vector, to block TAJ signaling or complex formation and permit beneficial axonal outgrowth.

Techniques for making and using antibodies and antibody fragments and homologues can be found, e.g., in Zola, *Monoclonal Antibodies: Preparation and Use of Monoclonal Antibodies and Engineered Antibody Derivatives (Basics: From Background to Bench)*, 1st edition, 2000, BIOS Scientific Publishers; and Osbourn (2003) *Drug Discov Today* 8(18): 845-51.

TAJ Polynucleotide Antagonists

Specific embodiments comprise a method of increasing neurite outgrowth, comprising administering an effective amount of a TAJ polynucleotide antagonist which comprises a nucleic acid molecule which specifically binds to a polynucleotide which encodes TAJ. The TAJ polynucleotide antagonist prevents expression of TAJ (knockdown). TAJ polynucleotide antagonists include, but are not limited to antisense molecules, ribozymes, siRNA, shRNA and RNAi. Typically, such binding molecules are separately administered to the animal (see, for example, O'Connor, *J. Neurochem.* 56:560 (1991)), but such binding molecules may also be expressed in vivo from polynucleotides taken up by a host cell and expressed in vivo. See also *Oligodeoxynucleotides as Antisense Inhibitors of Gene Expression*, CRC Press, Boca Raton, Fla. (1988).

RNAi refers to the expression of an RNA which interferes with the expression of the targeted mRNA. Specifically, the RNAi silences a targeted gene via interacting with the specific mRNA (e.g. TAJ) through a siRNA (short interfering RNA). The ds RNA complex is then targeted for degradation by the cell. Additional RNAi molecules include Short hairpin RNA (shRNA); also short interfering hairpin. The shRNA molecule contains sense and antisense sequences from a target gene connected by a loop. The shRNA is transported from the nucleus into the cytoplasm, it is degraded along with the mRNA. Pol III or U6 promoters can be used to express RNAs for RNAi.

RNAi is mediated by double stranded RNA (dsRNA) molecules that have sequence-specific homology to their "target" mRNAs (Caplen et al., *Proc Natl Acad Sci USA* 98:9742-9747, 2001). Biochemical studies in *Drosophila* cell-free lysates indicates that the mediators of RNA-dependent gene silencing are 21-25 nucleotide "small interfering" RNA duplexes (siRNAs). Accordingly, siRNA molecules are advantageously used in the methods of the present invention. The siRNAs are derived from the processing of dsRNA by an RNase known as DICER (Bernstein et al., *Nature* 409:363-366, 2001). It appears that siRNA duplex products are recruited into a multi-protein siRNA complex termed RISC (RNA Induced Silencing Complex). Without wishing to be bound by any particular theory, it is believed that a RISC is guided to a target mRNA, where the siRNA duplex interacts sequence-specifically to mediate cleavage in a catalytic fashion (Bernstein et al., *Nature* 409:363-366, 2001; Boutla et al., *Curr Biol* 11: 1776-1780, 2001).

RNAi has been used to analyze gene function and to identify essential genes in mammalian cells (Elbashir et al., *Methods* 26:199-213, 2002; Harborth et al., *J Cell Sci* 114:4557-4565, 2001), including by way of non-limiting example neurons (Krichevsky et al., *Proc Natl Acad Sci USA* 99:11926-11929, 2002). RNAi is also being evaluated for therapeutic modalities, such as inhibiting or blocking the infection, replication and/or growth of viruses, including without limitation poliovirus (Gitlin et al., *Nature* 418:379-380, 2002) and HIV (Capodici et al., *J Immunol* 169:5196-5201, 2002), and reducing expression of oncogenes (e.g., the bcr-abl gene; Scherr et al., *Blood* Sep 26 epub ahead of print, 2002). RNAi has been used to modulate gene expression in mammalian (mouse) and amphibian (*Xenopus*) embryos (respectively, Calegari et al., *Proc Natl Acad Sci USA* 99:14236-14240, 2002; and Zhou, et al., *Nucleic Acids Res* 30:1664-1669, 2002), and in postnatal mice (Lewis et al., *Nat Genet* 32:107-108, 2002), and to reduce trangsene expression in adult transgenic mice (McCaffrey et al., *Nature* 418:38-39, 2002). Methods have been described for determining the efficacy and specificity of siRNAs in cell culture and in vivo (see, e.g., Bertrand et al., *Biochem Biophys Res Commun* 296:1000-1004, 2002; Lassus et al., *Sci STKE* 2002(147): PL13, 2002; and Leirdal et al., *Biochem Biophys Res Commun* 295:744-748, 2002).

Molecules that mediate RNAi, including without limitation siRNA, can be produced in vitro by chemical synthesis (Hohjoh, *FEBS Lett* 521:195-199, 2002), hydrolysis of dsRNA (Yang et al., *Proc Natl Acad Sci USA* 99:9942-9947, 2002), by in vitro transcription with T7 RNA polymerase (Donzeet et al., *Nucleic Acids Res* 30:e46, 2002; Yu et al., *Proc Natl Acad Sci USA* 99:6047-6052, 2002), and by hydrolysis of double-stranded RNA using a nuclease such as *E. coli* RNase III (Yang et al., *Proc Natl Acad Sci USA* 99:9942-9947, 2002).

siRNA molecules may also be formed by annealing two oligonucleotides to each other, typically have the following general structure, which includes both double-stranded and single-stranded portions:

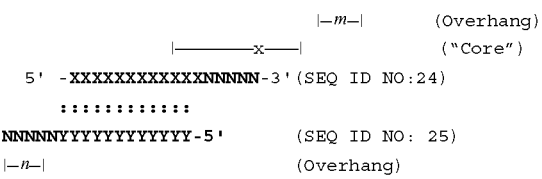

Wherein N, X and Y are nucleotides; X hydrogen bonds to Y; ":" signifies a hydrogen bond between two bases; x is a natural integer having a value between 1 and about 100; and m and n are whole integers having, independently, values between 0 and about 100. In some embodiments, N, X and Y are independently A, G, C and T or U. Non-naturally occurring bases and nucleotides can be present, particularly in the case of synthetic siRNA (i.e., the product of annealing two oligonucleotides). The double-stranded central section is called the "core" and has base pairs (bp) as units of measurement; the single-stranded portions are overhangs, having nucleotides (nt) as units of measurement. The overhangs shown are 3' overhangs, but molecules with 5' overhangs are also within the scope of the invention. Also within the scope of the invention are siRNA molecules with no overhangs (i.e., m=0 and n=0), and those having an overhang on one side of the core but not the other (e.g., m=0 and n>1, or vice-versa).

Initially, RNAi technology did not appear to be readily applicable to mammalian systems. This is because, in mammals, dsRNA activates dsRNA-activated protein kinase (PKR) resulting in an apoptotic cascade and cell death (Der et al, *Proc. Natl. Acad. Sci. USA* 94:3279-3283, 1997). In addition, it has long been known that dsRNA activates the interferon cascade in mammalian cells, which can also lead to altered cell physiology (Colby et al., *Annu. Rev. Microbiol.* 25:333, 1971; Kleinschmidt et al., *Annu. Rev. Biochem.* 41:517, 1972; Lampson et al., *Proc. Natl. Acad. Sci. USA* 58L782, 1967; Lomniczi et al., *J. Gen. Virol.* 8:55, 1970; and Younger et al., *J. Bacteriol.* 92:862, 1966). However, dsRNA-mediated activation of the PKR and interferon cascades requires dsRNA longer than about 30 base pairs. In contrast, dsRNA less than 30 base pairs in length has been demonstrated to cause RNAi in mammalian cells (Caplen et al., *Proc. Natl. Acad. Sci. USA* 98:9742-9747, 2001). Thus, it is expected that undesirable, non-specific effects associated with longer dsRNA molecules can be avoided by preparing short RNA that is substantially free from longer dsRNAs.

References regarding siRNA: Bernstein et al., *Nature* 409: 363-366, 2001; Boutla et al., *Curr Biol* 11:1776-1780, 2001; Cullen, *Nat Immunol.* 3:597-599, 2002; Caplen et al., *Proc Natl Acad Sci USA* 98:9742-9747, 2001; Hamilton et al., *Science* 286:950-952, 1999; Nagase et al., *DNA Res.* 6:63-70, 1999; Napoli et al., *Plant Cell* 2:279-289, 1990; Nicholson et al., *Mamm. Genome* 13:67-73, 2002; Parrish et al., *Mol Cell* 6:1077-1087, 2000; Romano et al., *Mol Microbiol* 6:3343-3353, 1992; Tabara et al., *Cell* 99:123-132, 1999; and Tuschl, *Chembiochem.* 2:239-245, 2001.

Paddison et al. (*Genes & Dev.* 16:948-958, 2002) have used small RNA molecules folded into hairpins as a means to effect RNAi. Accordingly, such short hairpin RNA (shRNA) molecules are also advantageously used in the methods of the invention. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the dsRNA products of the DICER RNase and, in any event, have the same capacity for inhibiting expression of a specific gene.

In some embodiments of the invention, the shRNA is expressed from a lentiviral vector, e.g., pLL3.7.

Antisense technology can be used to control gene expression through antisense DNA or RNA, or through triple-helix formation. Antisense techniques are discussed for example, in Okano, *J. Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' non-coding portion of a polynucleotide that encodes TAJ may be used to design an antisense RNA oligonucleotide of from about 10 to 40 base pairs in length. A DNA oligonucleotide is designed to be complementary to a region of the gene involved in transcription thereby preventing transcription and the production of the target protein. The antisense RNA oligonucleotide hybridizes to the mRNA in vivo and blocks translation of the mRNA molecule into the target polypeptide.

In one embodiment, antisense nucleic acids specific for the TAJ gene are produced intracellularly by transcription from an exogenous sequence. For example, a vector or a portion thereof, is transcribed, producing an antisense nucleic acid (RNA). Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the antisense molecule, can be by any promoter known in the art to act in vertebrate, preferably human cells, such as those described elsewhere herein.

Absolute complementarity of an antisense molecule, although preferred, is not required. A sequence complementary to at least a portion of an RNA encoding TAJ, means a sequence having sufficient complementarity to be able to hybridize with the RNA, forming a stable duplex; or triplex formation may be assayed. The ability to hybridize will depend on both the degree of complementarity and the length of the antisense nucleic acid. Generally, the larger the hybridizing nucleic acid, the more base mismatches it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of a messenger RNA, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333-335 (1994). Thus, oligonucleotides complementary to either the 5'- or 3'-non-translated, non-coding regions could be used in an antisense approach to inhibit translation of TAJ. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Polynucleotides for use the therapeutic methods disclosed herein can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. USA.* 86:6553-6556 (1989); Lemaitre et al., *Proc. Natl. Acad. Sci. USA* 84:648-652 (1987)); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., *BioTechniques* 6:958-976 (1988)) or intercalating agents. (See, e.g., Zon, *Pharm. Res.* 5:539-549(1988)). To this end, the oligonucleotide may be conjugated to another molecule, e.g., a peptide, hybridization triggered cross-linking agent, transport agent, hybridization-triggered cleavage agent, etc.

An antisense oligonucleotide for use in the therapeutic methods disclosed herein may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methylcytosine, N-6-adenine, 7-methylguanine, 5-methylaminomethyluracil, 5-methoxyaminomethyl-2-thiouracil, beta-D-mannosylqueosine, 5'methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3(3-amino-3-N-2-carboxypropyl) uracil, (acp3)w, and 2,6-diaminopurine.

An antisense oligonucleotide for use in the therapeutic methods disclosed herein may also comprise at least one modified sugar moiety selected from the group including, but not limited to, arabinose, 2-fluoroarabinose, xylulose, and hexose.

In yet another embodiment, an antisense oligonucleotide for use in the therapeutic methods disclosed herein comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, an antisense oligonucleotide for use in the therapeutic methods disclosed herein is an α-anomeric oligonucleotide. An α-anomeric oligonucleotide forms specific double-stranded hybrids with complementary RNA in which, contrary to the usual situation, the strands run parallel to each other (Gautier et al., *Nucl. Acids Res.* 15:6625-6641(1987)). The oligonucleotide is a 2'-β-methylribonucleotide (Inoue et al., *Nucl. Acids Res.* 15:6131-6148 (1987)), or a chimeric RNA-DNA analogue (Inoue et al., *FEBS Lett.* 215:327-330(1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al., *Nucl. Acids Res.* 16:3209 (1988), methylphosphonate oligonucleotides can be prepared by use of controlled pore glass polymer supports (Sarin et al., *Proc. Natl. Acad. Sci. USA.* 85:7448-7451(1988)), etc.

Polynucleotide compositions for use in the therapeutic methods disclosed herein further include catalytic RNA, or a ribozyme (See, e.g., PCT International Publication WO 90/11364, published Oct. 4, 1990; Sarver et al., *Science* 247: 1222-1225 (1990). The use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585-591 (1988). Preferably, the ribozyme is engineered so that the cleavage recognition site is located near the 5' end of the target mRNA; i.e., to increase efficiency and minimize the intracellular accumulation of non-functional mRNA transcripts.

As in the antisense approach, ribozymes for use in the diagnostic and therapeutic methods disclosed herein can be composed of modified oligonucleotides (e.g. for improved stability, targeting, etc.) and may be delivered to cells which express TAJ in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous TAJ messages and inhibit translation. Since ribozymes unlike antisense molecules, are catalytic, a lower intracellular concentration is required for efficiency.

Antisense

In some embodiments, TAJ expression can be inhibited by using antisense nucleic acids to directly block the translation of mRNA by hybridizing to targeted mRNA and preventing protein translation.

An "antisense" nucleic acid includes a nucleotide sequence which is complementary to a "sense" nucleic acid encoding the component, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire coding strand, or to only a portion thereof. For example, an antisense nucleic acid molecule which antisense to the "coding region" of the coding strand of a nucleotide sequence encoding the component can be used.

The coding strand sequence encoding TAJ is known. Thus, a skilled person can design antisense nucleic acids according to the rules of Watson and Crick base pairing. The antisense nucleic acid molecule can be complementary to the entire coding region of mRNA, but more preferably is an oligonucleotide which is antisense to only a portion of the coding or noncoding region of mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopenten-yladenine, uraci-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, Current Biology 4, 469-471 (1994), and PCT publication No. WO 97/3355.

A review of antisense therapeutics as it related to CNS disease is provided in Jaeger, 2004, Front Biosci. 9:1720-7.

RNAi

Expression of the TAJ gene can, in some embodiments, also be inhibited using RNA interference ("RNAi"). RNAi is a phenomenon in which the introduction of double-stranded RNA (dsRNA) into a cell causes degradation of the homologous mRNA. First discovered in the nematode *Caenorhabditis elegans*, RNAi has since been found to operate in a wide range of organisms. An "RNAi nucleic acid" as used herein is a nucleic acid sequence generally shorter than 50 nucleotides in length, that causes gene silencing at the mRNA level. RNAi nucleic acids include gene-specific short interfering RNAs (siRNA), and double-stranded RNAs (dsRNA).

For example, in mammalian cells, introduction of long dsRNA (>30 nucleotides) can initiate a potent antiviral response, exemplified by nonspecific inhibition of protein synthesis and RNA degradation. RNA interference provides a mechanism of gene silencing at the mRNA level. In recent years, RNAi has become an endogenous and potent gene-specific silencing technique that uses double-stranded RNAs (dsRNA) to mark a particular transcript for degradation in vivo. It also offers an efficient and broadly applicable approach for gene knock-out. In addition, RNAi technology can be used for therapeutic purposes. For example, RNAi targeting Fas-mediated apoptosis has been shown to protect mice from fulminant hepatitis. RNAi technology has been disclosed in numerous publications, such as U.S. Pat. Nos. 5,919,619, 6,506,559 and PCT Publication Nos. WO99/14346, WO01/70949, WO01/36646, WO00/63364, WO00/44895, WO01/75164, WO01/92513, WO01/68836 and WO01/29058.

A sequence capable of inhibiting gene expression by RNA interference can have any length. For instance, the sequence can have at least 10, 15, 20, 25, 30, 35, 40, 45, 50, 100 or more consecutive nucleotides. The sequence can be dsRNA or any other type of polynucleotide, provided that the sequence can form a functional silencing complex to degrade the target mRNA transcript.

In one embodiment, the sequence comprises or consists of a short interfering RNAs (siRNA). The siRNA can be dsRNA having 19-25 nucleotides. siRNAs can be produced endogenously by degradation of longer dsRNA molecules by an RNase III-related nuclease called Dicer. siRNAs can also be introduced into a cell exogenously, or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing.

At least two ways can be employed to achieve siRNA-mediated gene silencing. First, siRNAs can be synthesized in vitro and introduced into cells to transiently suppress gene expression. Synthetic siRNA provides an easy and efficient way to achieve RNAi. siRNA are duplexes of short mixed oligonucleotides which can include, for example, 19 RNAs nucleotides with symmetric dinucleotide 3' overhangs. Using synthetic 21 bp siRNA duplexes (e.g., 19 RNA bases followed by a UU or dTdT 3' overhang), sequence specific gene silencing can be achieved in mammalian cells. These siRNAs can specifically suppress targeted gene translation in mammalian cells without activation of DNA-dependent protein kinase (PKR) by longer dsRNA, which may result in non-specific repression of translation of many proteins. Second, siRNAs can be expressed in vivo from vectors.

Vectors

Vectors comprising nucleic acids encoding TAJ antagonists may also be used to produce antagonists for use in the methods of the invention. The choice of vector and expression control sequences to which such nucleic acids are operably linked depends on the functional properties desired, e.g., protein expression, and the host cell to be transformed.

In a typical embodiment, a TAJ polypeptide useful in the composition and methods described herein is a recombinant protein produced by a cell (e.g., a CHO cell) that carries an exogenous nucleic acid encoding the protein. In other embodiments, the recombinant polypeptide is produced by a process commonly known as gene activation, wherein a cell that carries an exogenous nucleic acid that includes a promoter or enhancer is operably linked to an endogenous nucleic acid that encodes the polypeptide.

Routine techniques for making recombinant polypeptides (e.g., recombinant TAJ or fragments thereof) may be used to construct expression vectors encoding the polypeptides of interest using appropriate transcriptional/translational control signals and the protein coding sequences. (See, for example, Sambrook et al., Molecular Cloning: A Laboratory Manual, 3d Ed. (Cold Spring Harbor Laboratory 2001)). These methods may include in vitro recombinant DNA and synthetic techniques and in vivo recombination, e.g., in vivo homologous recombination. Expression of a nucleic acid sequence encoding a polypeptide may be regulated by a second nucleic acid sequence that is operably linked to the polypeptide encoding sequence such that the polypeptide is expressed in a host transformed with the recombinant DNA molecule.

Expression control elements useful for regulating the expression of an operably linked coding sequence are known in the art. Examples include, but are not limited to, inducible promoters, constitutive promoters, secretion signals, and other regulatory elements. When an inducible promoter is used, it can be controlled, e.g., by a change in nutrient status, or a change in temperature, in the host cell medium.

Expression vectors capable of being replicated in a bacterial or eukaryotic host comprising a nucleic acid encoding a polypeptide are used to transfect a host and thereby direct expression of such nucleic acid to produce the polypeptide, which may then be isolated. The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Routine techniques for transfecting cells with exogenous DNA sequences may be used in the present invention. Transfection methods may include chemical means, e.g., calcium phosphate, DEAE-dextran, or liposome; or physical means, e.g., microinjection or electroporation. The transfected cells are grown up by routine techniques. For examples, see Kuchler et al. (1977) Biochemical Methods in Cell Culture and Virology. The expression products are isolated from the cell medium in those systems where the protein is secreted from the host cell, or from the cell suspension after disruption of the host cell system by, e.g., routine mechanical, chemical, or enzymatic means.

These methods may also be carried out using cells that have been genetically modified by other procedures, including gene targeting and gene activation (see Treco et al. WO 95/31560, herein incorporated by reference; see also Selden et al. WO 93/09222).

The vector can include a prokaryotic replicon, i.e., a DNA sequence having the ability to direct autonomous replication and maintenance of the recombinant DNA molecule extrachromosomally in a bacterial host cell. Such replicons are well known in the art. In addition, vectors that include a prokaryotic replicon may also include a gene whose expression confers a detectable marker such as a drug resistance. Examples of bacterial drug-resistance genes are those that confer resistance to ampicillin or tetracycline.

Vectors that include a prokaryotic replicon can also include a prokaryotic or bacteriophage promoter for directing expression of the coding gene sequences in a bacterial host cell. Promoter sequences compatible with bacterial hosts are typically provided in plasmid vectors containing convenient restriction sites for insertion of a DNA segment to be expressed. Examples of such plasmid vectors are pUC8, pUC9, pBR322 and pBR329 (BioRad), pPL and pKK223 (Pharmacia). Any suitable prokaryotic host can be used to express a recombinant DNA molecule encoding a protein used in the methods of the invention.

For the purposes of this invention, numerous expression vector systems may be employed. For example, one class of vector utilizes DNA elements which are derived from animal viruses such as bovine papilloma virus, polyoma virus, adenovirus, adeno-associated virus, herpes simplex virus-1, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. The neomycin phosphotransferase (neo) gene is an example of a selectable marker gene (Southern et al., *J. Mol. Anal. Genet.* 1:327-341 (1982)). Additional elements may also be needed for optimal synthesis of mRNA. These elements may include signal sequences, splice signals, as well as transcriptional promoters, enhancers, and termination signals.

In one embodiment, a proprietary expression vector of Biogen IDEC, Inc., referred to as NEOSPLA (U.S. Pat. No. 6,159,730) may be used. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression upon transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). Additional eukaryotic cell expression vectors are known in the art and are commercially available. Typically, such vectors contain convenient restriction sites for insertion of the desired DNA segment. Exemplary vectors include pSVL and pKSV-10 (Pharmacia), pBPV-1, pml2d (International Biotechnologies), pTDT1 (ATCC 31255), retroviral expression vector pMIG and pLL3.7, adenovirus shuttle vector pDC315, and AAV vectors. Other exemplary vector systems are disclosed e.g., in U.S. Pat. No. 6,413,777.

In general, screening large numbers of transformed cells for those which express suitably high levels of the antagonist is routine experimentation which can be carried out, for example, by robotic systems.

Frequently used regulatory sequences for mammalian host cell expression include viral elements that direct high levels of protein expression in mammalian cells, such as promoters and enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdmlP)), polyoma and strong mammalian promoters such as native immunoglobulin and actin promoters. For further description of viral regulatory elements, and sequences thereof, see e.g., Stinski, U.S. Pat. No. 5,168,062; Bell, U.S. Pat. No. 4,510,245; and Schaffner, U.S. Pat. No. 4,968,615.

The recombinant expression vectors may carry sequences that regulate replication of the vector in host cells (e.g., origins of replication) and selectable marker genes. The selectable marker gene facilitates selection of host cells into which the vector has been introduced (see, e.g., Axel, U.S. Pat. Nos. 4,399,216; 4,634,665 and 5,179,017). For example, typically the selectable marker gene confers resistance to a drug, such as G418, hygromycin or methotrexate, on a host cell into which the vector has been introduced. Frequently used selectable marker genes include the dihydrofolate reductase (DHFR) gene (for use in dhfr− host cells with methotrexate selection/amplification) and the neo gene (for G418 selection).

Vectors encoding TAJ antagonists can be used for transformation of a suitable host cell. Transformation can be by any suitable method. Methods for introduction of exogenous DNA into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

Transformation of host cells can be accomplished by conventional methods suited to the vector and host cell employed. For transformation of prokaryotic host cells, electroporation and salt treatment methods can be employed (Cohen et al., *Proc. Natl. Acad. Sci. USA* 69:2110-14 (1972)). For transformation of vertebrate cells, electroporation, cationic lipid or salt treatment methods can be employed. See, e.g., Graham et al., *Virology* 52:456-467 (1973); Wigler et al., *Proc. Natl. Acad. Sci. USA* 76:1373-76 (1979).

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, NSO, SP2 cells, baby hamster kidney (BHK) cells, monkey kidney cells (COS), human hepatocellular carcinoma cells (e.g., Hep G2), A549 cells DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

Expression of polypeptides from production cell lines can be enhanced using known techniques. For example, the glutamine synthetase (GS) system is commonly used for enhancing expression under certain conditions. See, e.g., European Patent Nos. 0 216 846, 0 256 055, and 0 323 997 and European Patent Application No. 89303964.4.

Host Cells

Host cells for expression of a TAJ antagonist for use in a method of the invention may be prokaryotic or eukaryotic. Exemplary eukaryotic host cells include, but are not limited to, yeast and mammalian cells, e.g., Chinese hamster ovary (CHO) cells (ATCC Accession No. CCL61), NIH Swiss mouse embryo cells NIH-3T3 (ATCC Accession No. CRL1658), and baby hamster kidney cells (BHK). Other useful eukaryotic host cells include insect cells and plant cells. Exemplary prokaryotic host cells are *E. coli* and *Streptomyces*.

A polypeptide produced by a cultured cell as described herein can be recovered from the culture medium as a secreted polypeptide, or, if it is not secreted by the cells, it can be recovered from host cell lysates. As a first step in isolating the polypeptide, the culture medium or lysate is generally centrifuged to remove particulate cell debris. The polypeptide thereafter is isolated, and preferably purified, from contaminating soluble proteins and other cellular components, with the following procedures being exemplary of suitable purification procedures: fractionation on immunoaffinity or ion-exchange columns; ethanol precipitation; reverse phase HPLC; chromatography on silica or on a cation-exchange resin such as DEAE; chromatofocusing; SDS PAGE; ammonium sulfate precipitation; and gel filtration, e.g., with Sephadex™ columns (Amersham Biosciences). Protease inhibitors may be used to inhibit proteolytic degradation during purification. One skilled in the art will appreciate that purification methods suitable for the polypeptide of interest may require modification to account for changes in the character of the polypeptide upon expression in recombinant cell culture.

The purification of polypeptides may require the use of, e.g., affinity chromatography, conventional ion exchange chromatography, sizing chromatography, hydrophobic interaction chromatography, reverse phase chromatography, gel filtration or other conventional protein purification techniques. See, e.g., Deutscher, ed. (1990) "Guide to Protein Purification" in Methods in Enzymology, Vol. 182.

Cell Therapy

In some embodiments of the invention a soluble TAJ polypeptide is administered in a treatment method that includes: (1) transforming or transfecting an implantable host cell with a nucleic acid, e.g., a vector, that expresses a TAJ polypeptide; and (2) implanting the transformed host cell into a mammal, at the site of a disease, disorder or injury. For example, the transformed host cell can be implanted at the site of a spinal cord injury. In some embodiments of the invention, the implantable host cell is removed from a mammal, temporarily cultured, transformed or transfected with an isolated nucleic acid encoding a TAJ polypeptide, and implanted back into the same mammal from which it was removed. The cell can be, but is not required to be, removed from the same site at which it is implanted. Such embodiments, sometimes known as ex vivo gene therapy, can provide a continuous supply of the TAJ polypeptide, localized at the site of site of action, for a limited period of time.

Gene Therapy

A TAJ antagonist can be produced in vivo in a mammal, e.g., a human patient, using a gene-therapy approach to treatment of a nervous-system disease, disorder or injury in which reducing inhibition of axonal extension would be therapeutically beneficial. This involves administration of a suitable TAJ antagonist-encoding nucleic acid operably linked to suitable expression control sequences. Generally, these sequences are incorporated into a viral vector. Suitable viral vectors for such gene therapy include an adenoviral vector, an alphavirus vector, an enterovirus vector, a pestivirus vector, a lentiviral vector, a baculoviral vector, a herpesvirus vector, an Epstein Barr viral vector, a papovaviral vector, a poxvirus vector, a vaccinia viral vector, adeno-associated viral vector and a herpes simplex viral vector. The viral vector can be a replication-defective viral vector. Adenoviral vectors that have a deletion in its E1 gene or E3 gene are typically used. When an adenoviral vector is used, the vector usually does not have a selectable marker gene.

Expression constructs of TAJ polypeptides may be administered in any biologically effective carrier, e.g. any formulation or composition capable of effectively delivering the TAJ gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA, encoding a TAJ polypeptide, or a TAJ antisense nucleic acid. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes. A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include .psi.Crip, .psi.Cre, .psi.2 and .psi.Am. Retroviruses have been used to introduce a variety of genes into many different cell types, including epithelial cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject gene is the adeno-associated virus (AAV). Reviewed in Ali, 2004, Novartis Found Symp. 255:165-78; and Lu, 2004, *Stem Cells Dev.* 13(1):133-45. Adeno-associated virus is a naturally occurring defective virus that requires another virus, such as an adenovirus or a herpes virus, as a helper virus for efficient replication and a productive life cycle. (For a review see Muzyczka et al. (1992) *Curr. Topics in Micro. and Immunol.* 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

In addition to viral transfer methods, such as those illustrated above, non-viral methods can also be employed to cause expression of a TAJ polypeptide, fragment, or analog, in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject TAJ gene by the targeted cell. Exemplary gene delivery systems of this type include liposomal derived systems, poly-lysine conjugates, and artificial viral envelopes. Other embodiments include plasmid injection systems such as are described in Meuli et al. (2001) *J Invest Dermatol.* 116(1):131-135; Cohen et al. (2000) *Gene Ther* 7(22):1896-905; or Tam et al. (2000) *Gene Ther* 7(21):1867-74.

In a representative embodiment, a gene encoding a TAJ polypeptide, active fragment, or analog, can be entrapped in liposomes bearing positive charges on their surface (e.g., lipofectins) and (optionally) which are tagged with antibodies against cell surface antigens of the target tissue (Mizuno et al. (1992) No Shinkei Geka 20:547-551; PCT publication WO91/06309; Japanese patent application 1047381; and European patent publication EP-A-43075).

In clinical settings, the gene delivery systems for the therapeutic TAJ gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *Pros. Natl. Acad. Sci. USA* 91: 3054-3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Guidance regarding gene therapy in particular for treating a CNS condition or disorder as described herein can be found, e.g., in U.S. patent application Ser. No. 2002/0,193,335 (provides methods of delivering a gene therapy vector, or transformed cell, to neurological tissue); U.S. patent application Ser. No. 2002/0,187,951 (provides methods for treating a neurodegenerative disease using a lentiviral vector to a target cell in the brain or nervous system of a mammal); U.S. patent application Ser. No. 2002/0,107,213 (discloses a gene therapy vehicle and methods for its use in the treatment and prevention of neurodegenerative disease); U.S. patent application Ser. No. 2003/0,099,671 (discloses a mutated rabies virus suitable for delivering a gene to the CNS); and U.S. Pat. No. 6,436,708 (discloses a gene delivery system which results in long-term expression throughout the brain); U.S. Pat. No. 6,140,111 (discloses retroviral vectors suitable for human gene therapy in the treatment of a variety of disease); and Kaspar et al. (2002) *Mol Ther.* 5:50-6' Suhr et al (1999) *Arch Neurol.* 56:287-92; and Wong et al. (2002) *Nat Neurosci* 5, 633-639).

Pharmaceutical Compositions

The TAJ antagonists used in the methods of the invention may be formulated into pharmaceutical compositions for administration to mammals, including humans. The pharmaceutical compositions used in the methods of this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions used in the methods of the present invention may be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. As described previously, TAJ antagonists used in the methods of the invention act in the nervous system to promote neuronal survival, neurite outgrowth, and/or axonal regeneration. Accordingly, in the methods of the invention, the TAJ antagonists are administered in such a way that they cross the blood-brain barrier. This crossing can result from the physico-chemical properties inherent in the TAJ antagonist molecule itself, from other components in a pharmaceutical formulation, or from the use of a mechanical device such as a needle, cannula or surgical instruments to breach the blood-brain barrier. Where the TAJ antagonist is a molecule that does not inherently cross the blood-brain barrier, e.g., a fusion to a moiety that facilitates the crossing, suitable routes of administration are, e.g., intrathecal or intracranial, e.g., directly into a chronic lesion of MS. Where the TAJ antagonist is a molecule that inherently crosses the blood-brain barrier, the route of administration may be by one or more of the various routes described below.

Sterile injectable forms of the compositions used in the methods of this invention may be aqueous or oleaginous suspension. These suspensions may be formulated according to techniques known in the art using suitable dispersing or wetting agents and suspending agents. The sterile, injectable preparation may also be a sterile, injectable solution or suspension in a non-toxic parenterally acceptable diluent or solvent, for example as a suspension in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Compositions containing an agent described herein, e.g., TAJ polypeptides, anti-TAJ antibodies, or antigen binding fragments of anti-TAJ antibodies may contain suitable pharmaceutically acceptable carriers. For example, they may contain excipients and/or auxiliaries that facilitate processing of the active compounds into preparations designed for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension include, for example, sodium carboxymethyl cellulose, sorbitol and dextran. Optionally, the suspension may also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In some embodiments, the compositions comprise pharmaceutically acceptable substances such as wetting or minor amounts of auxiliary substances such as wetting or emulsifying agents, preservatives or buffers, which enhance the shelf life or effectiveness of the active ingredients.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in the methods of this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

Compositions of the invention may be in a variety of forms, including, for example, liquid (e.g., injectable and infusible solutions), dispersions, suspensions, semi-solid and solid dosage forms. The preferred form depends on the mode of administration and therapeutic application. For treating tissues in the central nervous system, administration can be, e.g., by injection or infusion into the cerebrospinal fluid (CSF). Administration can also be with one or more agents capable of promoting penetration of TAJ polypeptide across the blood-brain barrier.

The composition can be formulated as a solution, microemulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., *Sustained and Controlled Release Drug Delivery Systems*, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In some embodiments, a TAJ polypeptide, anti-TAJ antibody or fragment thereof is coadministered with an anti-NgR1 antibody, or an antigen-binding fragments thereof.

The amount of a TAJ antagonist that may be combined with the carrier materials to produce a single dosage form will vary depending upon the host treated, the type of antagonist used and the particular mode of administration. The composition may be administered as a single dose, multiple doses or over an established period of time in an infusion. Dosage regimens also may be adjusted to provide the optimum desired response (e.g., a therapeutic or prophylactic response).

The methods of the invention use a "therapeutically effective amount" or a "prophylactically effective amount" of a TAJ antagonist. Such a therapeutically or prophylactically effective amount may vary according to factors such as the disease state, age, sex, and weight of the individual. A therapeutically or prophylactically effective amount is also one in which any toxic or detrimental effects are outweighed by the therapeutically beneficial effects.

A specific dosage and treatment regimen for any particular patient will depend upon a variety of factors, including the particular TAJ antagonist used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Dosage regimens may be adjusted to provide the optimum desired response. For example, a single bolus may be administered, several divided doses may be administered over time, or the dose may be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form may contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

In the methods of the invention the TAJ antagonists are generally administered directly to the nervous system, intracerebroventricularly, or intrathecally, e.g. into a chronic lesion of MS. Compositions for administration according to the methods of the invention can be formulated so that a dosage of 0.001-10 mg/kg body weight per day of the TAJ antagonist polypeptide is administered. In some embodiments of the invention, the dosage is 0.01-1.0 mg/kg body weight per day. In some embodiments, the dosage is 0.001-0.5 mg/kg body weight per day.

For treatment with a TAJ antagonist antibody, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

In certain embodiments, a subject can be treated with a nucleic acid molecule encoding a TAJ antagonist polynucleotide. Doses for nucleic acids range from about 10 ng to 1 g, 100 ng to 100 mg, 1 μg to 10 mg, or 30-300 μg DNA per patient. Doses for infectious viral vectors vary from 10-100, or more, virions per dose.

Supplementary active compounds also can be incorporated into the compositions used in the methods of the invention. For example, a soluble TAJ polypeptide or a fusion protein may be coformulated with and/or coadministered with one or more additional therapeutic agents.

The invention encompasses any suitable delivery method for a TAJ antagonist to a selected target tissue, including bolus injection of an aqueous solution or implantation of a controlled-release system. Use of a controlled-release implant reduces the need for repeat injections.

The TAJ antagonists used in the methods of the invention may be directly infused into the brain. Various implants for direct brain infusion of compounds are known and are effective in the delivery of therapeutic compounds to human patients suffering from neurological disorders. These include chronic infusion into the brain using a pump, stereotactically implanted, temporary interstitial catheters, permanent intracranial catheter implants, and surgically implanted biodegradable implants. See, e.g., Gill et al., supra; Scharfen et al., "High Activity Iodine-125 Interstitial Implant For Gliomas," *Int. J. Radiation Oncology Biol. Phys.* 24(4):583-591 (1992); Gaspar et al., "Permanent 1251 Implants for Recurrent Malignant Gliomas," *Int. J. Radiation Oncology Biol. Phys.* 43(5):977-982 (1999); chapter 66, pages 577-580, Bellezza et al., "Stereotactic Interstitial Brachytherapy," in Gildenberg et al., Textbook of Stereotactic and Functional Neurosurgery, McGraw-Hill (1998); and Brem et al., "The Safety of Interstitial Chemotherapy with BCNU-Loaded Polymer Followed by Radiation Therapy in the Treatment of Newly Diagnosed Malignant Gliomas: Phase I Trial," *J. Neuro-Oncology* 26:111-23 (1995).

The compositions may also comprise a TAJ antagonist dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., *Biopolymers* 22:547-56 (1985)); poly(2-hydroxyethyl-methacrylate), ethylene vinyl acetate (Langer et al., *J. Biomed. Mater. Res.* 15:167-277 (1981); Langer, *Chem. Tech.* 12:98-105 (1982)) or poly-D-(−)-3hydroxybutyric acid (EP 133,988).

In some embodiments of the invention, a TAJ antagonist is administered to a patient by direct infusion into an appropriate region of the brain. See, e.g., Gill et al., "Direct brain infusion of glial cell line-derived neurotrophic factor in Parkinson disease," *Nature Med.* 9: 589-95 (2003). Alternative techniques are available and may be applied to administer a TAJ antagonist according to the invention. For example, stereotactic placement of a catheter or implant can be accomplished using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three-dimensional multiplanar treatment planning (STP, Fischer, Freiburg, Germany). This equipment permits planning on the basis of magnetic resonance imaging studies, merging the CT and MRI target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 nun intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

The methods of treatment of CNS disorders as described herein are typically tested in vitro, and then in vivo in an acceptable animal model, for the desired therapeutic or prophylactic activity, prior to use in humans. Suitable animal models, including transgenic animals, are will known to those of ordinary skill in the art. For example, in vitro assays to demonstrate the differentiation and survival effect of the TAJ antagonists are described herein. The effect of the TAJ antagonists on regeneration of axons can be tested in vitro as described in the Examples. Finally, in vivo tests can be performed by creating transgenic mice which express the TAJ antagonist or by administering the TAJ antagonist to mice

EXAMPLES

The invention is further illustrated by the following experimental examples. The examples are provided for illustrative purposes only, and are not to be construed as limiting the scope or content of the invention in any way.

Example 1

Production of TAJ Fusion Proteins

Residues 1-168 of murine TAJ fused to the hinge and Fc region of human IgG1 was expressed in CHO cells and purified on Protein A Sepharose (Pharmacia). The purified protein ran on SDS-PAGE with Mr=50 KDa under reducing conditions and Mr=D KDa under non-reducing conditions. AP-TAJ (human placental AP with an N-terminal six-histidine-tag fused at its C terminus to human TAJ residues 26-168) was expressed in CHO cells. The protein was purified on TMAE-Fractogel (EM Industries) and Ni-NTA Agarose (Qiagen). A similar strategy were used for the construction, expression, and purification of AP-p75, AP-Nogo66, which was expressed in 293 cells. Myelin preparations were purified from wildtype C57B16 mouse and bovine brains using standard protocols (Norton and Podulso, 1973).

Example 2

TAJ Binds NgR1 and LINGO-1

This example shows the association of TAJ with NgR1 and LINGO-1 using a number of different biochemical approaches.

Figure 1A:
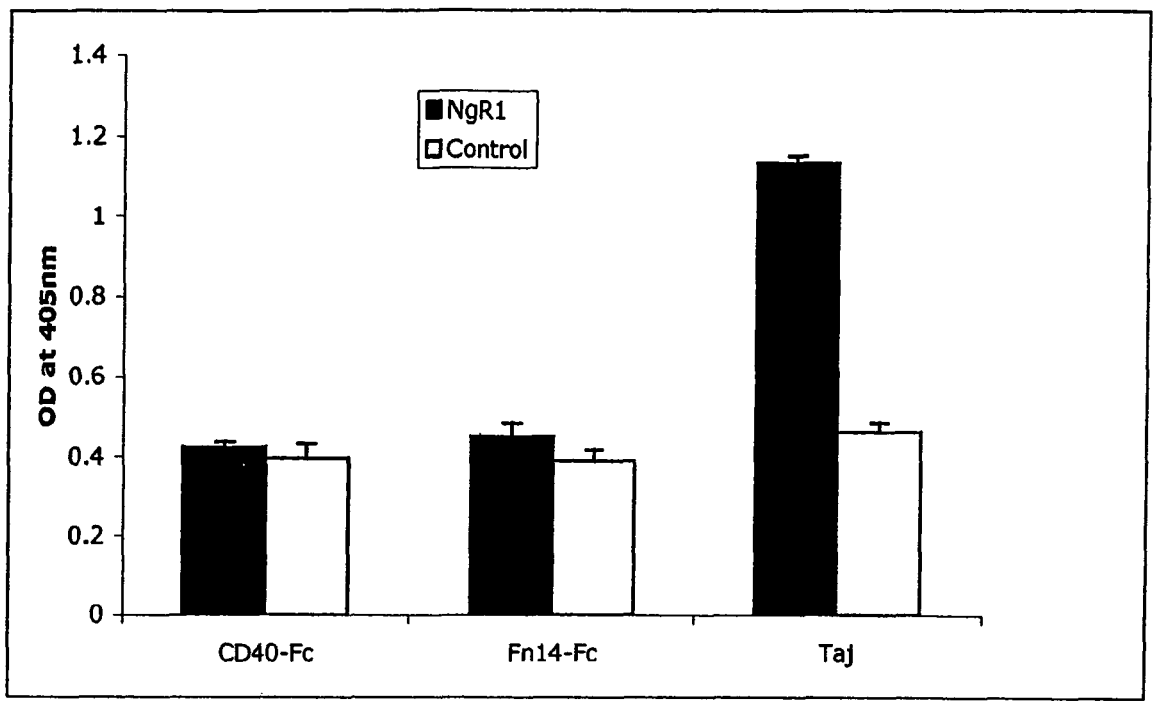

ELISA plates (Costar) were coated with 10 µg/ml soluble NgR1 (rat NgR1 ectodomain residues 1-310 or 1-344 fused to the hinge and Fc of rat IgG1) or full length NgR1. The plates were blocked, and incubated at 4° C. overnight with a number of TNFR superfamily/Fc fusion proteins (30 µg/ml), including TAJ-Fc, CD40-Fc, Fn14-Fc, TNFR1-Fc, TNFR2-Fc and BaffR-Fc. The plates were washed with PBS plus 0.05% Tween-20 and bound fusion proteins were detected with anti-human-Ig conjugated with HPR. Sonic hedgehog-Fc was used as a specificity control. As shown in FIG. 1A, of all the candidates screened, only TAJ-Fc bound to NgR1.

90% confluent COS-7 cells were transfected with human NgR1 expression plasmids using Fugene 6 reagents (Roche). After 48 h, the transfected cells were washed with HBH (Hank's balanced salt buffer, 1 mg/ml BSA, 20 mM Hepes, pH 7.0), incubated for 1.5 h at 23° C. with 4 µg/ml of AP-TAJ or other AP-fusions in HBH, and processed as described (Mi et al. 2004). Bound AP-TAJ was detected directly by incubation with NBT/BCIP (Roche) or following extraction lysis of the cells (Mi et al. 2004). In selected studies, COS-7 cells were transfected with various combinations of NgR1, p75, and LINGO-1 and analyzed for AP-TAJ binding as described above.

Figure 1C:
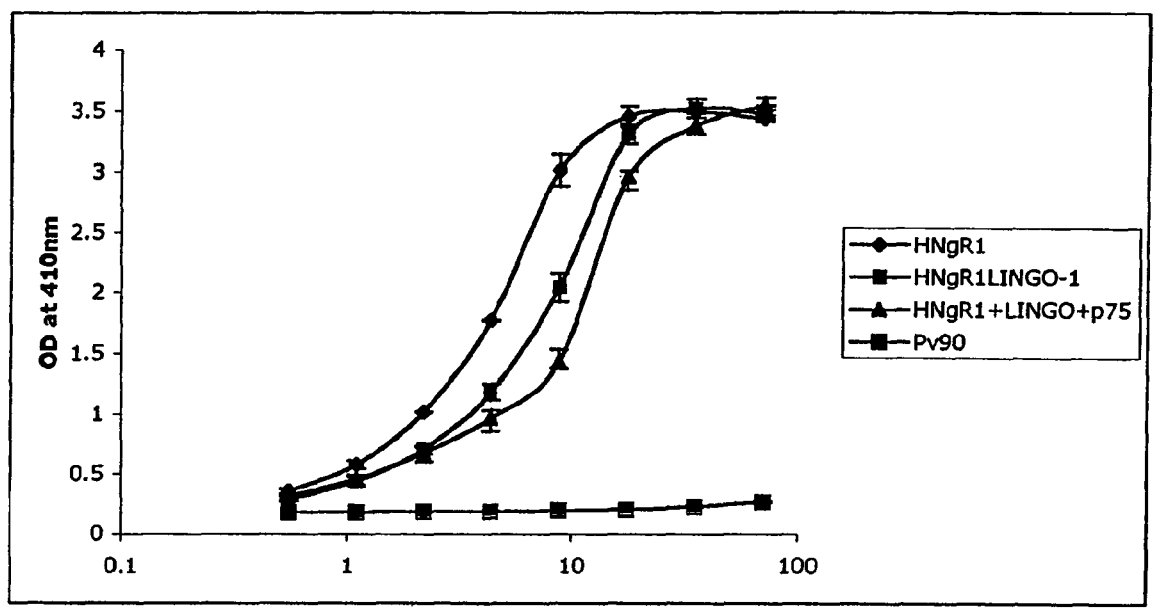

TAJ binding to NgR1 was confirmed in subsequent analyses with expressed AP-TAJ fusion protein (FIG. 1B, 1C). TAJ binding of other identified components of the MAIF receptor complex, both individually and in various combinations, was also evaluated. TAJ binding to COS cells co-expressing NgR1/LINGO-1 and NgR1/LINGO-1/p75 was slightly lower than NgR1 alone, perhaps due to competition or steric hindrance. Notably, TAJ binds NgR1 with markedly higher affinity than p75 (FIG. 1B).

Figure 3:
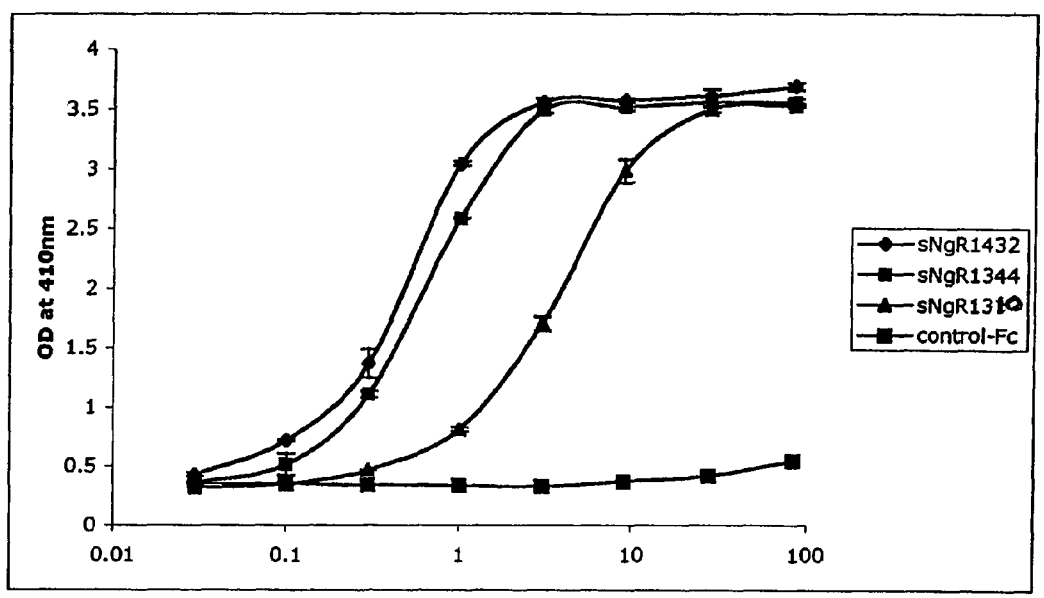
FIG. 3 is a graph showing results of an ELISA assay for binding of AP-TAJ to full length (sNgR1-432) and truncated (sNgR1-344 and sNgR1-310) NgR1.

To identify the region of NgR1 bound by TAJ, soluble truncated forms of NgR1 were generated and used to coat ELISA plates for binding by AP-TAJ. A truncated NgR1 construct containing 344 amino acids from the amino terminus was bound by TAJ as effectively as full-length NgR1. However, a slightly shorter construct containing the N-terminal 310 amino acids showed far less affinity for AP-TAJ, suggesting that amino acids 310-344 of NgR1 are important to Taj/NgR1 binding (FIG. 3).

COS-7 cells (100 mm dishes) were transfected with combinations of Human TAJ and human NgR1, human TAJ, human LINGO-1, human NgR1/rat p75 and human NgR1/BaffR. BaffR was used as a specificity control. The cells were harvested after 48 h and lysed in 1 ml lysis buffer (50 mM HEPES, pH 7.5, 150 mM NaCl, 1.5 mM $MgCl_2$, 1 mM EGTA, 1% Triton X-100 and 10% glycerol) for 30 min at 4° C. After centrifugation at 14,000×g for 15 min, the supernatants were incubated with Protein A/G-Sepharose beads (Santa Cruz Biotechnology, Inc.) at 4° C. for 1 h and then incubated at 4° C. for 1 h with either anti-NgR1, anti-TAJ antibody plus Protein A/G-Sepharose beads or myc tagged anti-LINGO-1 plus anti-myc (9E10) agarose bead. The beads were washed three times with lysis buffer, boiled in Laemmli sample buffer, subjected to 4-20% SDS-PAGE, and analyzed by Western blotting with anti-NgR1 or anti-LINGO-1 or anti-TAJ (Alexis Biochemical) antibodies. Human TAJ residue 26 to 416 were inserted into PV90 HA tag expression vector.

Figure 2:
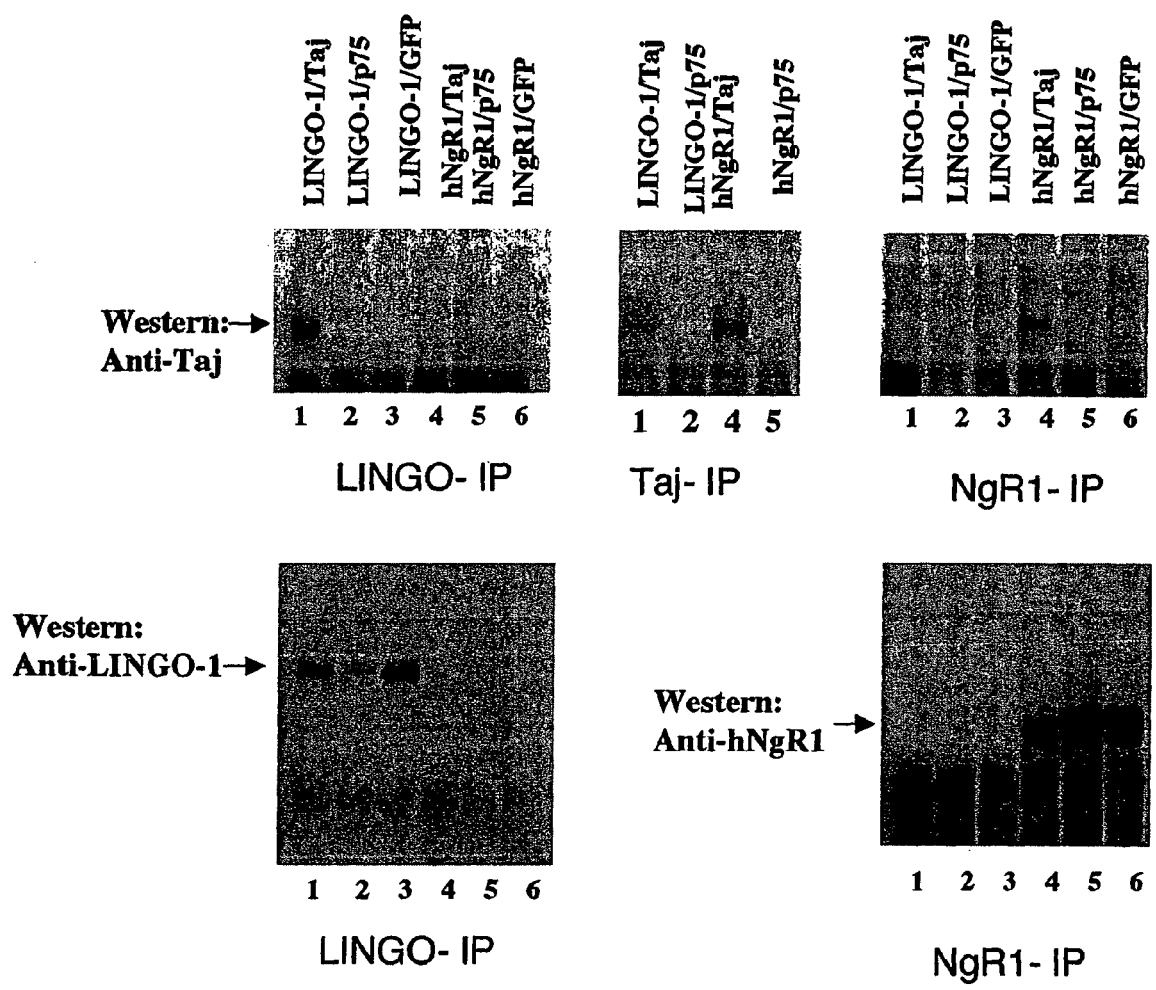
FIG. 2 is a series of Western blots of immunoprecipitation experiments. Various combinations of proteins as indicated were co-expressed and cell extracts immunoprecipitated with the indicated antibodies (top panels: anti-TAJ; bottom panels: anti-LINGO-1).

Binding of NgR1 and LINGO-1 by human-TAJ was verified by immunoprecipitation studies in which TAJ was combined with NgR1 or LINGO-1 (FIG. 2). Co-expression of TAJ and NgR1 or TAJ and LINGO-1 followed by immunoprecipitation with anti-NgR1 or LINGO-1 antibodies yielded an anti-TAJ immunoreactive band in Western blots. Similarly, immunoprecipitation of the reaction mixture with anti-TAJ antibodies yielded a band on Western blots that was easily detected by NgR1 or LINGO-1 antibodies. These data show that TAJ associates with NgR1 and LINGO-1.

Example 3

TAJ Expression in Brain

This example shows that TAJ is expressed is highly and widely expressed in brain.

Northern analyses of human multiple tissue and human brain blots (Clontech) were performed using standard protocols and a human TAJ probe generated using PCR (419 bp fragment, forward primer (5'-tatgggaggatgcacagtgtgtg-3' (SEQ ID NO: 19)) and reverse primer (5'-agaccagctgggtttct-tctccat-3' (SEQ ID NO: 20)).

Mouse tissue cDNAs (Clontech) and rat cDNAs were analyzed by semi-quantitative PCR using a forward primer (5'-tatgggaggatgcacagtgtgtg-3' (SEQ ID NO: 19)) and reverse primer (5'-agaccagctgggtttcttctccat-3' (SEQ ID NO: 20)) that yield an amplified TAJ fragment of 419 bp. Amplification of GAPDH was carried out in parallel for normalization purposes. For PCR analysis of individual rat cell types, purified cultures of postnatal day 6-7 (P6-7) cerebellar granular neurons, P2 cerebellar oligodendrocytes, P4 cerebellar astrocytes, and embryonic day 14 (E14) dorsal root ganglia neurons were prepared as described (insert-references-here or insert-methodology-here) and harvested for RNA using Trizol reagent and manufacturer's protocol (Invitrogen). Purified RNAs were used to generate cell-type specific cDNA using GeneAmp kit (Applied Biosystems).

mRNA was extracted from embryonic day 14 (E14), E18, postnatal day 0 (P0), P4, P8, P23, and adult mouse brains using Trizol reagent (Invitrogen). These RNAs were subjected to Taqman RT-PCR to quantify TAJ, p75, LINGO-1, and NgR1 message levels.

Transcriptional analysis by semi-quantitative PCR confirmed that high levels of TAJ mRNA are found in the mouse brain, with more moderate expression in the heart, lung, liver, skeletal muscle, and testis. TAJ mRNA expression was broadly distributed across multiple brain regions, with highest expression in the cortex, cerebellum, hippocampus, and thalamus.

To determine whether TAJ is expressed in neurons, astrocytes or oligodendrocytes, purified cultures of postnatal day 6-7 (P6-7) cerebellar granular neurons, P2 cerebellar oligodendrocytes, P4 cerebellar astrocytes, and embryonic day 14 (E14) dorsal root ganglia neurons were prepared and analyzed for TAJ mRNA by semi-quantitative RT-PCR. Roughly comparable levels of message were found in each cell type.

Relative levels of expression of TAJ were compared to gain insight into the potential composition of the MAIF receptor complex in the developing and adult brain. Quantitative real-time PCR was performed for TAJ on whole rat brain homogenates taken over a developmental timecourse spanning E14, E18, P0, P4, P8, P11, P23, and adult. These data showed that TAJ expression is dramatically reduced in P23 and adult rats (FIG. 6).

Purified cultures of P6-7 cerebellar granule neurons were grown for 24 hour in vitro and then stained using anti-TAJ, p75, LINGO-1, and NgR1 antibodies. The immunohistochemical data shows that TAJ, LINGO-1 and NgR1 are colocalized in the same cells.

Example 4

TAJ Induces Rho Activation

This example shows that TAJ mediates Rho activation in response to an inhibitor of neurite outgrowth.

Binding of the MAIF receptor by Nogo, Omgp, or MAG leads to the activation of RhoA, a step in the MAIF receptor signaling pathway that is critical to the inhibitory effects of myelin on neurite outgrowth. To determine whether the interaction of TAJ and NgR1 is truly indicative of a MAIF receptor complex that is functionally active, COS cells were transfected with various combinations of TAJ, NgR1, and LINGO-1, and treated with AP-tagged Omgp or an unrelated AP-tagged control protein. The level of activated RhoA in the cells was then measured. COS-7 cells were treated with AP-OMgp ligands for 10 min, lysed in 50 mM Tris-HCl, pH 7.5, 1% Triton X-100, 0.5% sodium deoxycholate, 0.1% SDS, 500 mM NaCl, 10 mM $MgCl_2$, plus protease inhibitors. GTP-bound and total RhoA proteins were detected by Western blotting using an anti-RhoA mAb (Santa Cruz).

COS cells transfected with TAJ alone, TAJ and LINGO-1, or TAJ and NgR1 showed no increase in activated RhoA. However, transfection with all three components led to increased RhoA activation following treatment with AP-Omgp (not shown), indicating that expression of TAJ, LINGO-1, and NgR1 was sufficient to reconstitute a functional MAIF receptor capable of downstream signaling.

Example 5

Making of TAJ Knock-out Mice

TAJ knockout mice were generated in which the first two coding exons of the TAJ gene were deleted by homologous recombination. TAJ knockout mice were created on a mixed 129 Sv/C57B16 background. The first 66 amino acids of the first coding exon for TAJ were deleted by homologous recombination with a human CD2-neomycin fusion construct (FIG. 4). There are at least two splice variants for Taj; however, both use the same initiating methionine, and the CD2-neo construct contains two stop codons (one in frame, one not), so deletion of TAJ is believed to be complete. The absence of TAJ mRNA expression was verified by RT-PCR of TAJ knockout mouse brain RNA. Primers used were wildtype upstream-5'-AGGAAGAGAATGGCAGCGAAGAGC-3' (SEQ ID NO: 21), knockout upstream-5'-CAAGTTGAT-GTCCTGACCCAAGGCACC-3' (SEQ ID NO: 22), and wildtype/knockout downstream 5'-AGCGCCTCGTATG-GACAAAGAGTG-3' (SEQ ID NO: 23), and yielded wildtype and knockout amplified fragments of 195 and 277 bp, respectively.

These mice are grossly normal, with no obvious physical abnormalities or alterations in behavior, locomotion, or fecundity. RT-PCR was performed to confirm that TAJ gene knock out using mouse brain tissues.

Primary CG or DRG neuron cultures were prepared using Labtek culture slides (8 well) were coated with 0.1 mg/ml poly-D-lysine (Sigma) before spotting with 300 ng/3 ul AP-Nogo66, or 500 ng/3 µl myelin alone; or with 1 µg/3 µl TAJ-Fc or control-Fc (human IgG1-hinge-CH2CH3 portion of fusion protein) in the presence of AP-Nogo66 (300 ng/3 µl). The slides were dried at room temperature for two hours. CG neurons ($1\times10^5$ cells/8 well) or 5000 DRG/96 well from p7 rats were dissociated and seeded onto the slides, and incubated at 37° C. in 5% $CO_2$ for 24 hr. The slides were fixed in 4% paraformaldehyde/20% sucrose and stained with anti-βIII-tubulin (Covance TUJ1).

Example 6

Neurons Lacking TAJ Show Decreased Responsiveness to Neurite Inhibition

Figure 5A:
Figure 5A:
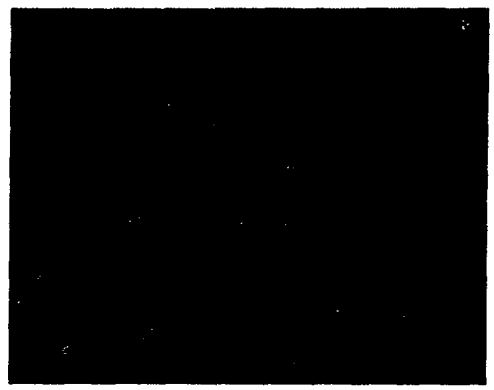
Figure 5A:
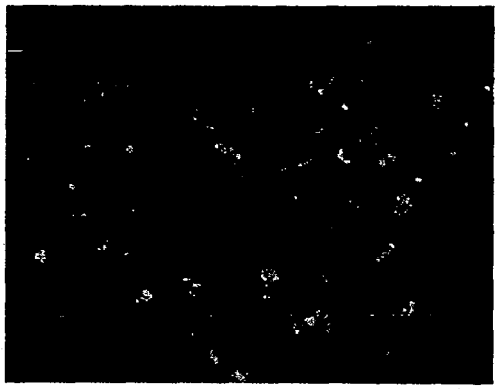
Figure 5A:
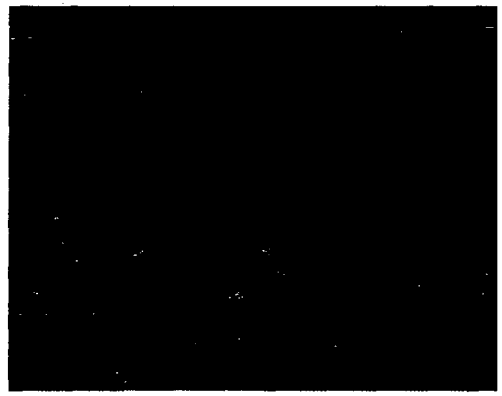
Figure 5B:
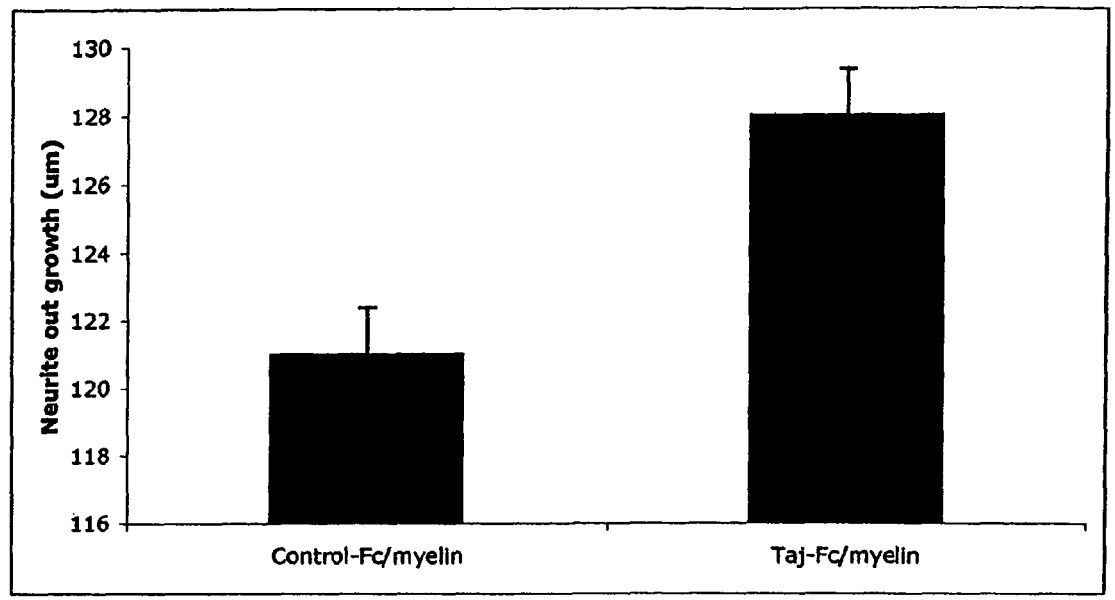
Figure 5C:
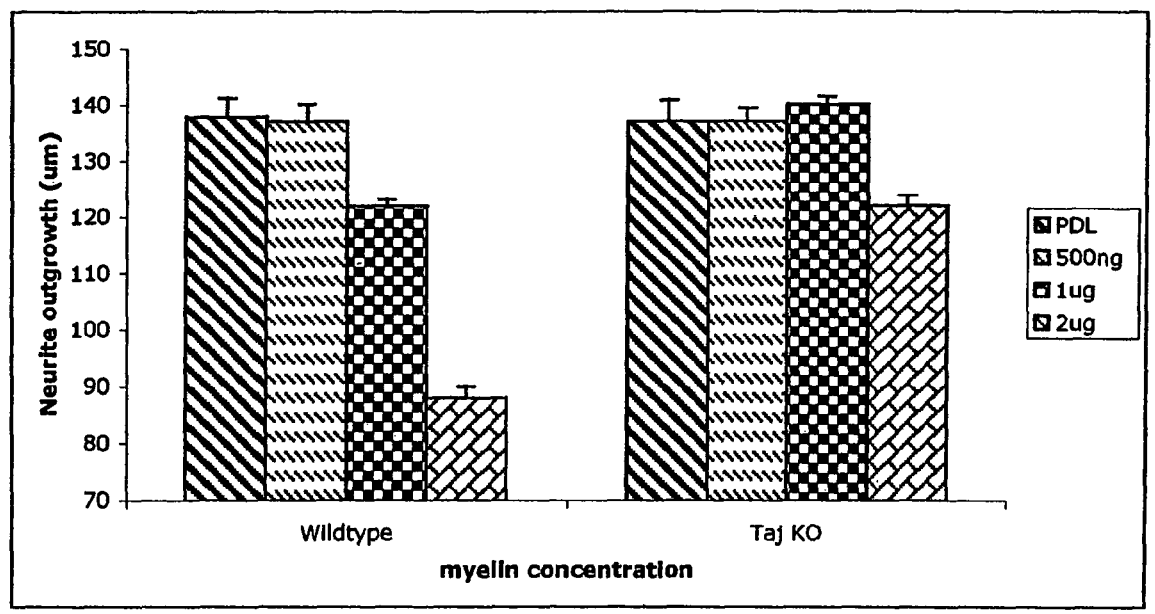
Figure 5:
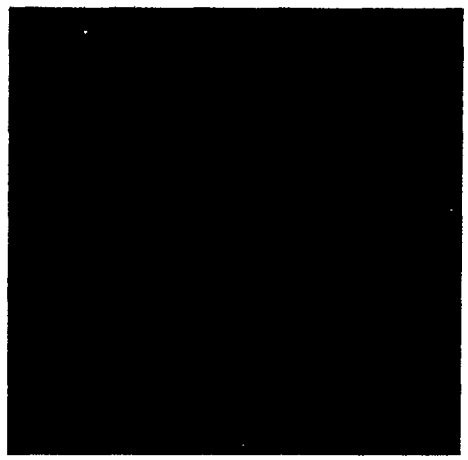
Figure 5:
Figure 5:
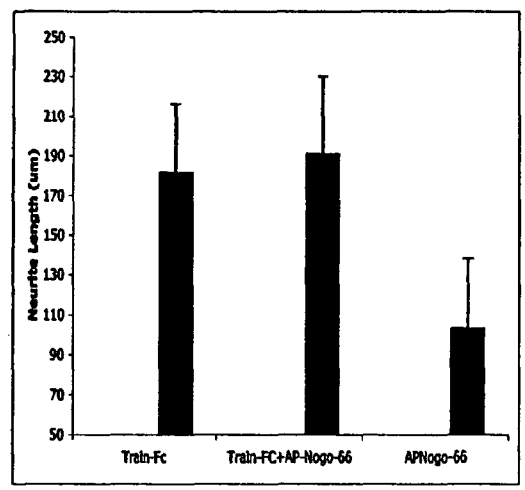

To analyze the effects of TAJ deletion upon the response of neurons to MAIFs, P8 cerebellar granule neurons (CGNs) from TAJ knockout and wild-type mice were plated onto myelin-coated slides and neurite outgrowth was measured 1 day after plating (FIGS. 5A and 5B). Quantitation of neurite length from TAJ knockout CGNs in respective dose-response curves indicates that CGNs lacking TAJ are less responsive to myelin-induced inhibition than wildtype CGNs (FIG. 5C).

The inhibitory response to myelin could be reduced in normal CGNs by disrupting the MAIF receptor complex with a TAJ-Fc fusion protein. Addition of TAJ-Fc led to longer CGN outgrowth, suggesting that the MAIF receptor complex was being compromised (FIG. 5A, 5B).

A dramatic effect of Taj-Fc on the restoration of neurite outgrowth was seen using dissociated DRG neurons from postnatal day 7 rats. When grown on a substrate of poly-D-lysine (PDL) and an AP-Nogo66 substrate, the normally extensive neurite outgrowth seen after 24 hours in vitro is dramatically curtailed compared to growth on PDL alone. However, if TAJ-Fc is also added to the substrate, DRG outgrowth is restored up to near-control levels (FIG. 5D). Other TNFR-Fc family members tested: CD40-Fc, TNFR1-Fc, TNFR2-Fc, Fn14-Fc and LTβR-Fc did not have an effect on rat DRG neurite out growth (data not shown). This result shows that TAJ is specifically involved in regulated axon growth.

What is claimed is:

1. A method of increasing neurite outgrowth, in a CNS neuron, the method comprising contacting the CNS neuron with an effective amount of an agent that reduces TAJ signaling in the neuron, wherein the agent is a soluble TAJ polypeptide, which consists of a polypeptide wherein the N-terminus is between amino acids 20-50 of SEQ ID NO:2 and the C-terminus is between amino acids 130-176 of SEQ ID NO:2.

2. The method of claim 1, wherein the CNS neuron is a human CNS neuron.

3. The method of claim 2, wherein the human CNS neuron is selected from the group consisting of: a CG neuron, a DRG neuron.

4. The method of claim 1, wherein the CNS neuron is in a mammal.

5. The method of claim 4, wherein the CNS neuron is in a human.

6. A method of promoting CNS neurite outgrowth in a subject, the method comprising: identifying a subject in need of increased neurite outgrowth, and administering to the subject an agent that decreases TAJ signaling or complex formation in a CNS neuron of the subject in an amount sufficient to increase neurite outgrowth, wherein the agent is a soluble TAJ polypeptide which consists of a polypeptide wherein the N-terminus is between amino acids 20-50 of SEQ ID NO:2 and the C-terminus is between amino acids 130-176 of SEQ ID NO:2.

7. The method of claim 6, wherein the method further includes evaluating the subject for neuronal function.

8. The method of claim 6, wherein the subject is a human.

9. The method of claim 8, wherein the subject has a CNS neurodegenerative condition.

10. The method of claim 9, wherein the neurodegenerative condition is multiple sclerosis, progressive multifocal leukoencephalopathy (PML), central pontine myelinolysis (CPM), leukodystrophies ALS, Huntington's disease, Alzheimer's disease, Parkinson's disease, or diabetic neuropathy.

11. The method of claim 6, wherein the agent is administered in combination with a second therapeutic agent.

12. The method of claim 11, wherein the second therapeutic agent is an analgesic, an antibiotic or a corticosteroid.

13. A method of increasing neurite outgrowth in a CNS neuron, the method comprising contacting the CNS neuron with an effective amount of an agent that reduces TAJ signaling in the neuron, wherein the agent is a soluble TAJ polypeptide fused to a heterologous amino acid sequence, wherein the N-terminus of the TAJ polypeptide is between amino acids 20-50 of SEQ ID NO:2 and the C-terminus is between amino acids 130-176 of SEQ ID NO:2.

14. The method of claim 13, wherein the heterologous amino acid sequence comprises an Fc region of an immunoglobulin.

15. A method of promoting CNS neurite outgrowth in a subject, the method comprising: identifying a subject in need of increased neurite outgrowth, and administering to the subject an agent that decreases TAJ signaling or complex formation in a CNS neuron of the subject in an amount sufficient to increase neurite outgrowth, wherein the agent is a soluble TAJ polypeptide fused to a heterologous amino acid sequence, wherein the N-terminus of the TAJ polypeptide is between amino acids 20-50 of SEQ ID NO:2 and the C-terminus is between amino acids 130-176 of SEQ ID NO:2.

16. The method of claim 15, wherein the heterologous amino acid sequence comprises an Fc region of an immunoglobulin.

* * * * *